United States Patent
Gehring et al.

(10) Patent No.: US 11,492,610 B2
(45) Date of Patent: Nov. 8, 2022

(54) SAMPLE MULTIPLEXING FOR SINGLE-CELL RNA SEQUENCING

(71) Applicant: California Institute of Technology, Pasadena, CA (US)

(72) Inventors: Jase Gehring, Pasadena, CA (US); Lior S. Pachter, Pasadena, CA (US); Siyu Chen, Los Angles, CA (US); Jong Hwee Park, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 513 days.

(21) Appl. No.: 16/296,075

(22) Filed: Mar. 7, 2019

(65) Prior Publication Data

US 2019/0276818 A1    Sep. 12, 2019

Related U.S. Application Data

(60) Provisional application No. 62/640,399, filed on Mar. 8, 2018.

(51) Int. Cl.
| | | |
|---|---|---|
| *C12N 15/10* | (2006.01) | |
| *C12Q 1/6806* | (2018.01) | |
| *C40B 40/08* | (2006.01) | |
| *C12Q 1/6869* | (2018.01) | |

(52) U.S. Cl.
CPC ....... *C12N 15/1065* (2013.01); *C12Q 1/6806* (2013.01); *C12Q 1/6869* (2013.01); *C40B 40/08* (2013.01); *C12Q 2535/122* (2013.01); *C12Q 2563/185* (2013.01); *C12Q 2600/16* (2013.01)

(58) Field of Classification Search
CPC .............. C12N 15/1065; C12Q 1/6806; C12Q 1/6869; C12Q 2535/122; C12Q 2535/185; C12Q 2600/16; C40B 40/08
See application file for complete search history.

(56) References Cited

U.S. PATENT DOCUMENTS

| | | | |
|---|---|---|---|
| 2019/0111412 A1* | 4/2019 | Yi | ...................... B01J 20/28085 |
| 2020/0140556 A1* | 5/2020 | Kenkel | ............ A61K 39/00117 |
| 2020/0405640 A1* | 12/2020 | Zhang | ................ C07K 16/2809 |

FOREIGN PATENT DOCUMENTS

| | | |
|---|---|---|
| EP | 2714752 | 11/2017 |
| WO | WO2014026032 | 2/2014 |
| WO | WO2015126840 | 8/2015 |
| WO | WO2018002016 | 1/2018 |
| WO | WO2018031247 | 2/2018 |

OTHER PUBLICATIONS

Zhao et al., "Clickable Multifunctional Dumbbell Particles for in Situ Multiplex Single-Cell Cytokine Detection", ACS Appl. Mater. Interfaces 2017, 9, 32482-32488 (Year: 2017).*

(Continued)

*Primary Examiner* — Jeremy C Flinders
(74) *Attorney, Agent, or Firm* — Sheppard, Mullin, Richter & Hampton LLP

(57) ABSTRACT

Disclosed herein include systems, methods, compositions, and kits for multiplexing single-cell RNA-sequencing (scRNA-seq) samples. In some embodiments, the methods comprise chemically tagging cells with identifying sample tags (e.g., barcoded DNA oligonucleotides).

22 Claims, 61 Drawing Sheets

Specification includes a Sequence Listing.

(56) References Cited

OTHER PUBLICATIONS

Devaraj et al., "Fast and Sensitive Pretargeted Labeling of Cancer Cells through a Tetrazine/trans-Cyclooctene Cycloaddition", Angew. Chem. Int. Ed. 2009, 48, 7013-7016 (Year: 2009).*
10X Genomics Support, Single Cell Gene Expression Datasets, https://support.10xgenomics.com/single-cell-gene-expression/datasets, in 4 pages, accessed on Apr. 21, 2020.
Bond et al., "Adult Mammalian Neural Stem Cells and Neurogenesis: Five Decades Later," Cell Stem Cell. 2015, 17(4), 385-395.
Butler et al., "Integrating single-cell transcriptomic data across different conditions, technologies, and species," Nat Biotechnol. 2018, 36(5), 411-420.
Cao et al., "Comprehensive single cell transcriptional profiling of a multicellular organism," Science 2017, 357(6352), 661-667.
Cao et al., "The single-cell transcriptional landscape of mammalian organogenesis," Nature 2019, 566, 496-498.
Datlinger et al., "Pooled CRISPR screening with single-cell transcriptome read-out," Nat Methods. 2017, 14(3), 297-301.
Gehring et al., "Highly Multiplexed Single-Cell RNA-seq for Defining Cell Population and Transcriptional Spaces," bioRxiv 2018, 315333, in 19 pages, https://doi.org/10.1101/315333.
Han et al., "Mapping the Mouse Cell Atlas by Microwell-Seq," Cell 2018, 172, 1091-1107.
Hitoshi et al., "Mammalian Gcm genes induce Hes5 expression by active DNA demethylation and induce neural stem cells," Nature Neuroscience 2011, 14(8), 957-967.
Hsiao et al., "Direct Cell Surface Modification with DNA for the Capture of Primary Cells and the Investigation of Myotube Formation on Defined Patterns," Langmuir 2009, 25(12), 6985-6991.
Imayoshi et al., "Oscillatory Control of Factors Determining Multipotency and Fate in Mouse Neural Progenitors," Science 2013, 342(6163), 1203-1208.
International Search Report and Written Opinion dated Jun. 21, 2019 in PCT Patent Application No. PCT/US2019/021226.
Janes et al., "A Systems Model of Signaling Identifies a Molecular Basis Set for Cytokine-Induced Apoptosis," Science 2005, 310, 1646-1653.
Kang et al., "Multiplexed droplet single-cell RNA-sequencing using natural genetic variation," Nat Biotechnol. 2018, 36(1), 89-94.
Klein et al., "Droplet Barcoding for Single-Cell Transcriptomics Applied to Embryonic Stem Cells," Cell 2015, 161, 1187-1201.
Lamb et al., "The Connectivity Map: Using Gene-Expression Signatures to Connect Small Molecules, Genes, and Disease," Science 2006, 313(5795), 1929-1935.
Macosko et al., "Highly parallel genome-wide expression profiling of individual cells using nanoliter droplets," Cell 2015, 161(5), 1202-1214.
Melsted et al., "The Barcode, UMI, Set format and BUStools," bioRxiv 2018, 472571, in 5 pages. https://doi.org/10.1101/472571.
Nelander et al., "Models from experiments: combinatorial drug perturbations of cancer cells," Molecular Systems Biology 2008, 4(216), 1-11.
Peterson et al., "Multiplexed quantification of proteins and transcripts in single cells," Nat Biotechnol 2017, 35(10), 936-939.
Picelli et al., "Full-length RNA-seq from single cells using Smart-seq2," Nature Protocols 2014, 9(1), 171-181.
Shin et al., "Multiplexed single-cell RNA-seq via transient barcoding for drug screening." bioRxiv 2018, 359851, in 21 pages. https://doi.org/10.1101/359851.
Sims et al., "High-throughput RNA interference screening using pooled shRNA libraries and next generation sequencing," Genome Biology 2011, 12(R104), 1-13.
Stoeckius et al., "Simultaneous epitope and transcriptome measurement in single cells," Nat Methods 2017, 14(9), 865-868.
Stoeckius et al., "Cell "hashing" with barcoded antibodies enables multiplexing and doublet detection for single cell genomics," bioRxiv 2017, 237693, in 16 pages. https://doi.org/10.1101/237693.
Suryawanshi et al., "A single-cell survey of the human first-trimester placenta and decidua," Sci Adv. 2018, 4(eaau4788), 1-12.
Svensson et al., "Exponential scaling of single-cell RNA-seq in the last decade," Nature Protocols 2018, 13(4), 599-604.
Wolf et al., "SCANPY: large-scale single-cell gene expression data analysis," Genome Biology 2018, 19(15), 1-5.
Wolock et al., "Scrublet: computational identification of cell doublets in single-cell transcriptomic data," bioRxiv 2018, 357368, in 18 pages, https://doi.org/10.1101/357368.
Yuzwa et al., "Developmental Emergence of Adult Neural Stem Cells as Revealed by Single-Cell Transcriptional Profiling," Cell Reports 2017, 21, 3970-3986.
Zheng et al., "Massively parallel digital transcriptional profiling of single cells," Nature Communications 2017, 8(14049), 1-12.

* cited by examiner

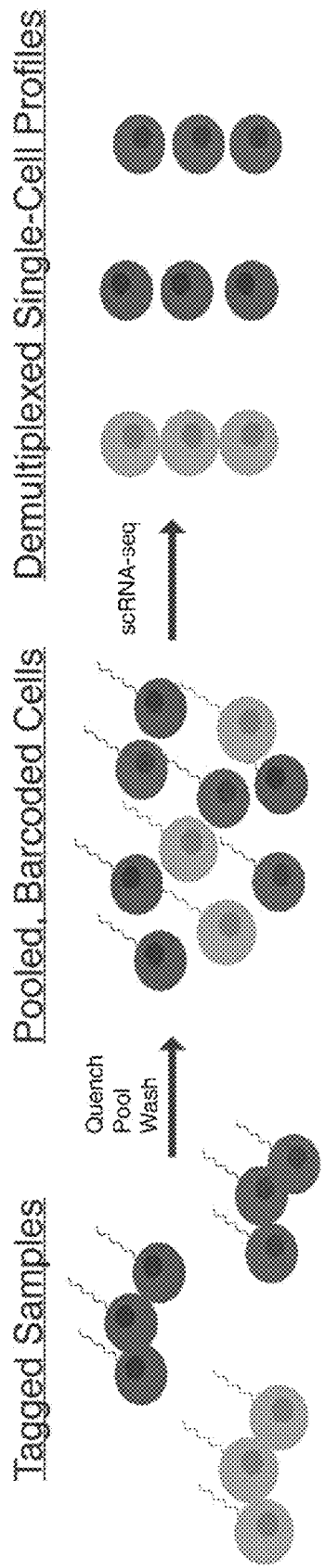
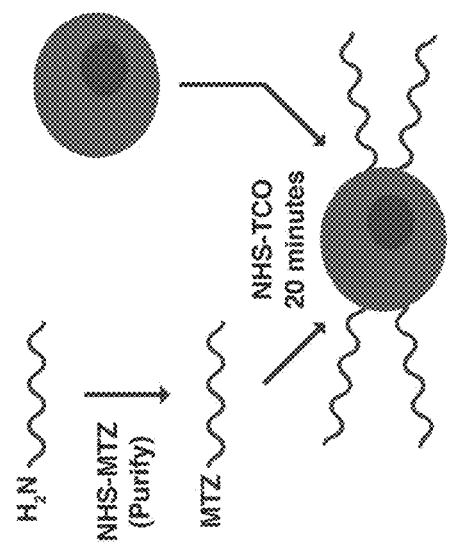
FIG. 1A
FIG. 1B

FIG. 4

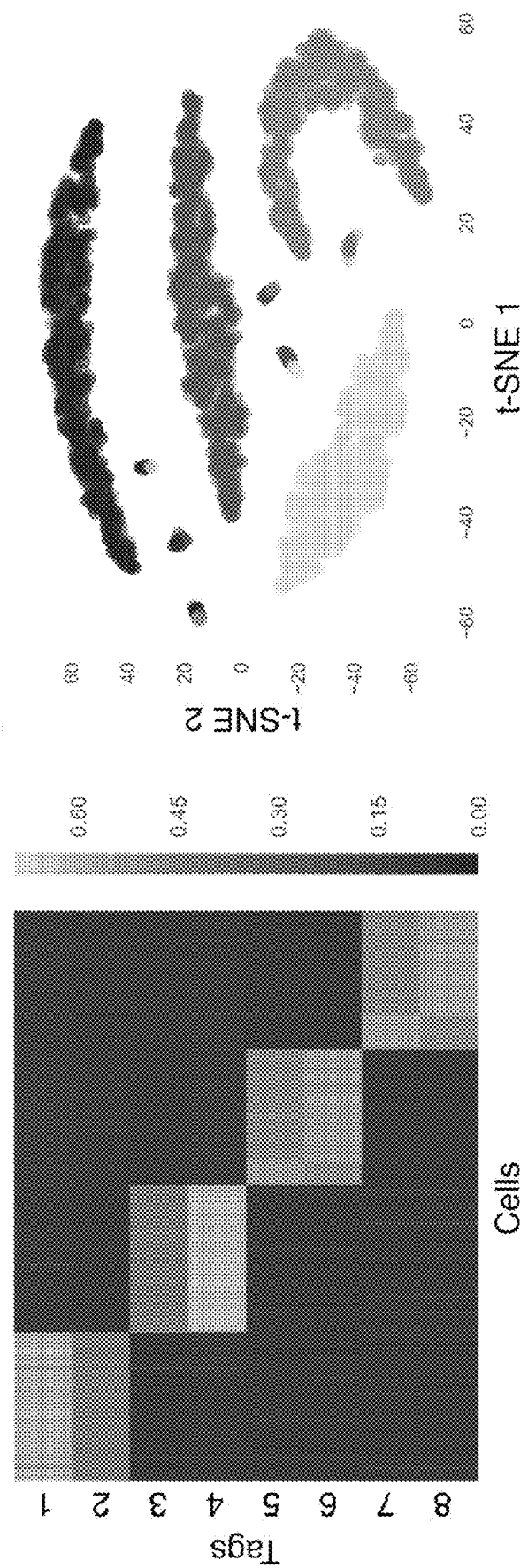

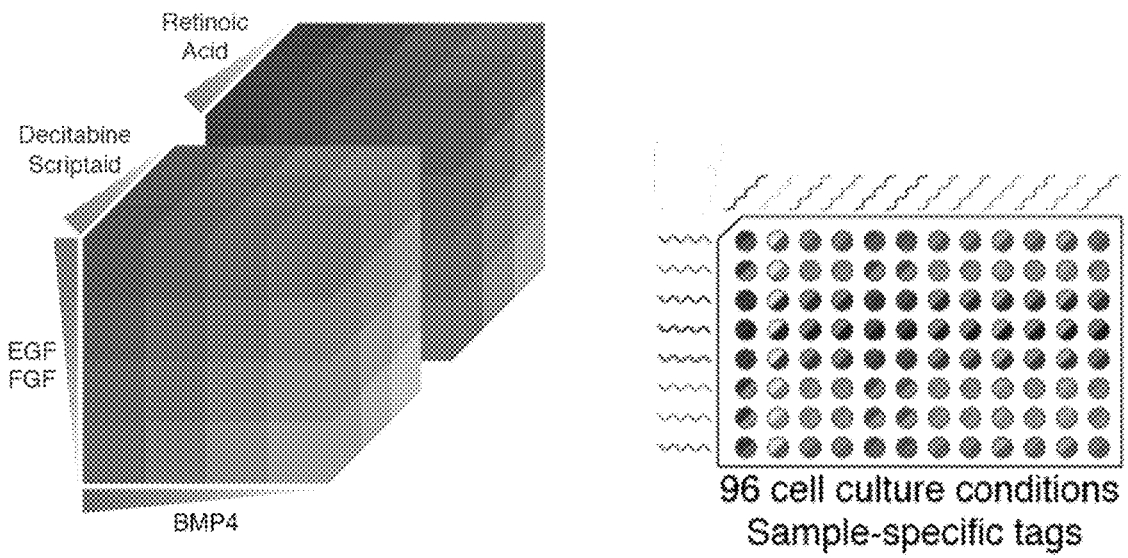
FIG. 9A
FIG. 9C
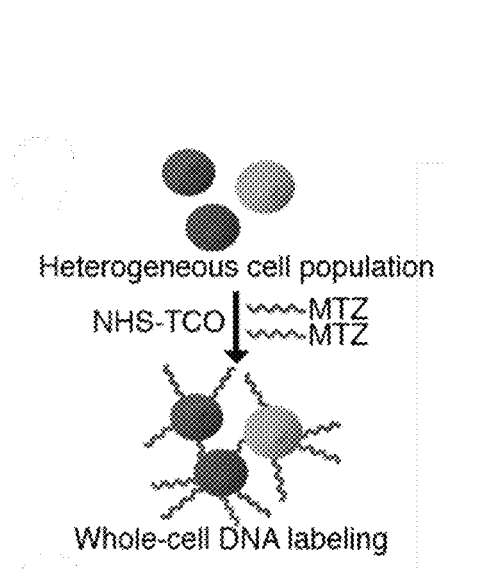
FIG. 9B
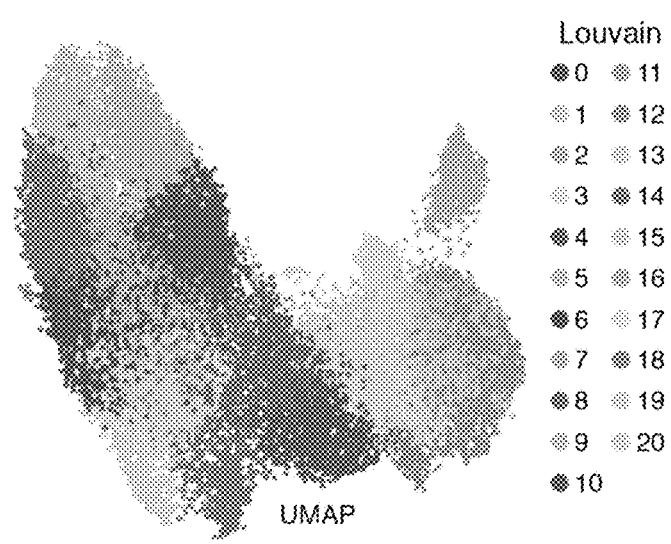
FIG. 9D

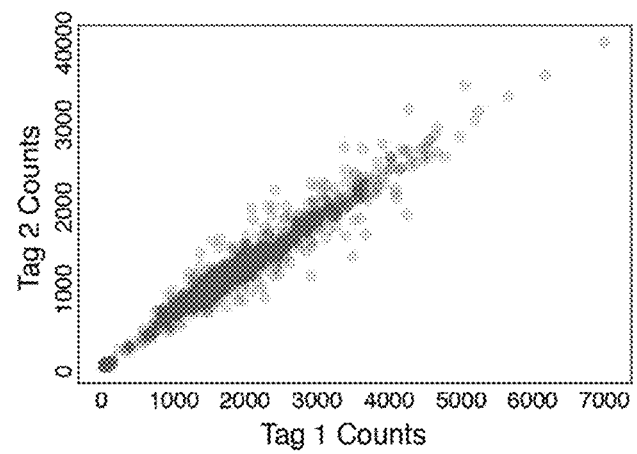
FIG. 12C
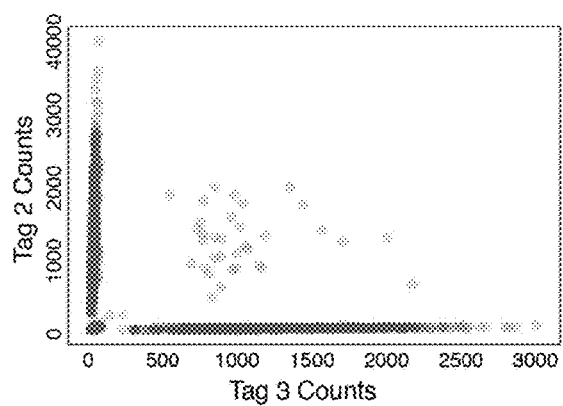 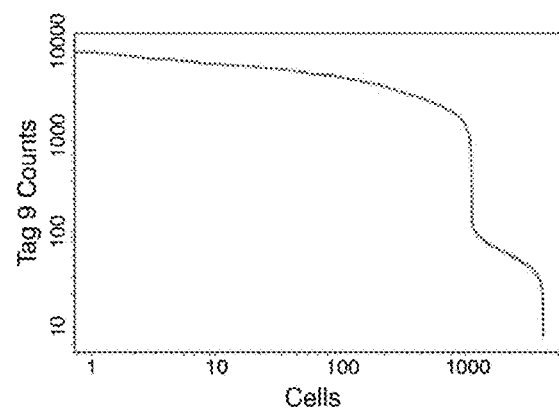
FIG. 12D    FIG. 12E

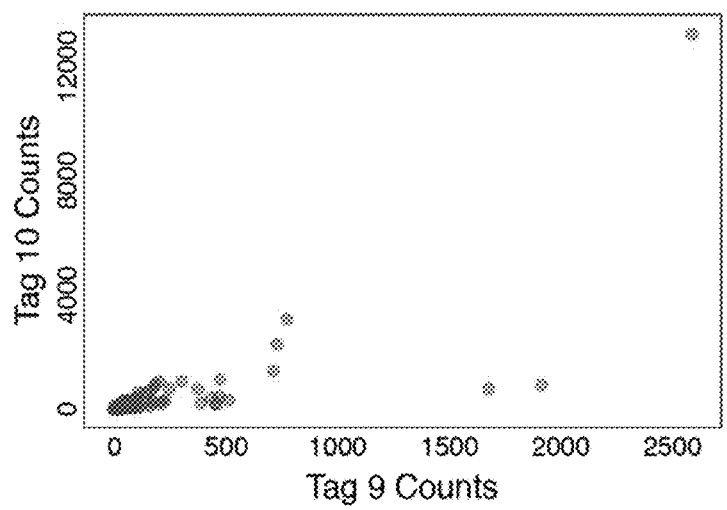
FIG. 12H
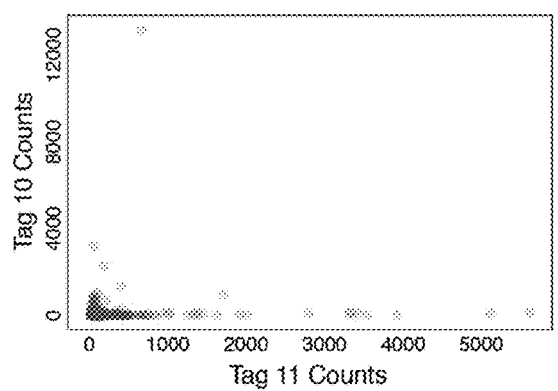 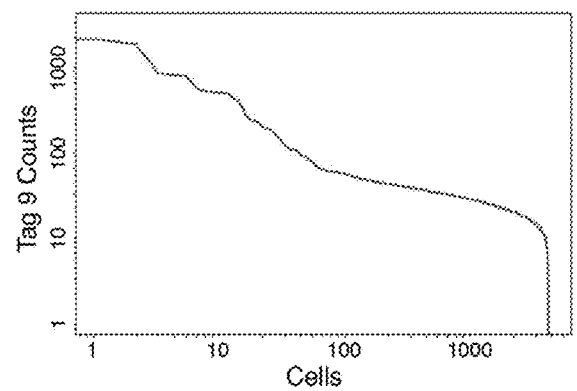
FIG. 12I  FIG. 12J

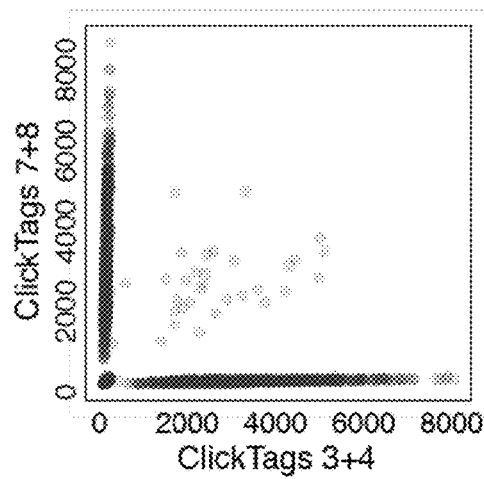 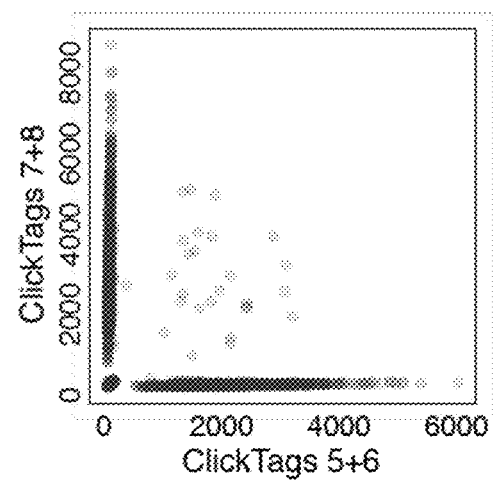
*FIG. 13I*  *FIG. 13J*

FIG. 23C

Mix 3 ClickTags

Mix 4 ClickTags

Mix 5 ClickTags

SEQUENCE LISTING

```
<160> NUMBER OF SEQ ID NOS: 45

<210> SEQ ID NO 1
<211> LENGTH: 60
<212> TYPE: DNA
<213> ORGANISM: Artificial Sequence
<220> FEATURE:
<223> OTHER INFORMATION: Synthetic; BC21; 5' Amino Modifier C6

<400> SEQUENCE: 1
tcgtcggcag cgtcagatgt gtaagcagtt acagbaaaaa aaaaaaaaaa aaaaaaaaaa        60

<210> SEQ ID NO 2
<211> LENGTH: 60
<212> TYPE: DNA
<213> ORGANISM: Artificial Sequence
<220> FEATURE:
<223> OTHER INFORMATION: Synthetic; BC22; 5' Amino Modifier C6

<400> SEQUENCE: 2
tcgtcggcag cgtcagatgt gtacttgtac ccagbaaaaa aaaaaaaaaa aaaaaaaaaa        60

<210> SEQ ID NO 3
<211> LENGTH: 60
<212> TYPE: DNA
<213> ORGANISM: Artificial Sequence
<220> FEATURE:
<223> OTHER INFORMATION: Synthetic; BC23; 5' Amino Modifier C6

<400> SEQUENCE: 3
tcgtcggcag cgtcagatgt gtagaacccg gcagbaaaaa aaaaaaaaaa aaaaaaaaaa        60

<210> SEQ ID NO 4
<211> LENGTH: 60
<212> TYPE: DNA
<213> ORGANISM: Artificial Sequence
<220> FEATURE:
<223> OTHER INFORMATION: Synthetic; BC24; 5' Amino Modifier C6

<400> SEQUENCE: 4
tcgtcggcag cgtcagatgt gtatcgtaga tcagbaaaaa aaaaaaaaaa aaaaaaaaaa        60
```

```
<210> SEQ ID NO 5
<211> LENGTH: 60
<212> TYPE: DNA
<213> ORGANISM: Artificial Sequence
<220> FEATURE:
<223> OTHER INFORMATION: Synthetic; BC25; 5' Amino Modifier C6

<400> SEQUENCE: 5
tcgtcggcag cgtcagatgt gtaacgcgga acagbaaaaa aaaaaaaaaa aaaaaaaaaa      60

<210> SEQ ID NO 6
<211> LENGTH: 60
<212> TYPE: DNA
<213> ORGANISM: Artificial Sequence
<220> FEATURE:
<223> OTHER INFORMATION: Synthetic; BC26; 5' Amino Modifier C6

<400> SEQUENCE: 6
tcgtcggcag cgtcagatgt gtacgctatc ccagbaaaaa aaaaaaaaaa aaaaaaaaaa      60

<210> SEQ ID NO 7
<211> LENGTH: 60
<212> TYPE: DNA
<213> ORGANISM: Artificial Sequence
<220> FEATURE:
<223> OTHER INFORMATION: Synthetic; BC27; 5' Amino Modifier C6

<400> SEQUENCE: 7
tcgtcggcag cgtcagatgt gtagttgcat gcagbaaaaa aaaaaaaaaa aaaaaaaaaa      60

<210> SEQ ID NO 8
<211> LENGTH: 60
<212> TYPE: DNA
<213> ORGANISM: Artificial Sequence
<220> FEATURE:
<223> OTHER INFORMATION: Synthetic; BC28; 5' Amino Modifier C6

<400> SEQUENCE: 8
tcgtcggcag cgtcagatgt gtataaatcg tcagbaaaaa aaaaaaaaaa aaaaaaaaaa      60

<210> SEQ ID NO 9
<211> LENGTH: 60
<212> TYPE: DNA
<213> ORGANISM: Artificial Sequence
<220> FEATURE:
<223> OTHER INFORMATION: Synthetic; BC29; 5' Amino Modifier C6

<400> SEQUENCE: 9
tcgtcggcag cgtcagatgt gtaatcgcca tcagbaaaaa aaaaaaaaaa aaaaaaaaaa      60

<210> SEQ ID NO 10
<211> LENGTH: 60
<212> TYPE: DNA
<213> ORGANISM: Artificial Sequence
<220> FEATURE:
<223> OTHER INFORMATION: Synthetic; BC30; 5' Amino Modifier C6

<400> SEQUENCE: 10
tcgtcggcag cgtcagatgt gtacataaag gcagbaaaaa aaaaaaaaaa aaaaaaaaaa      60

<210> SEQ ID NO 11
<211> LENGTH: 60
<212> TYPE: DNA
<213> ORGANISM: Artificial Sequence
<220> FEATURE:
<223> OTHER INFORMATION: Synthetic; BC31; 5' Amino Modifier C6
```

```
<400> SEQUENCE: 11
tcgtcggcag cgtcagatgt gtatcacggt acagbaaaaa aaaaaaaaaa aaaaaaaaaa        60

<210> SEQ ID NO 12
<211> LENGTH: 60
<212> TYPE: DNA
<213> ORGANISM: Artificial Sequence
<220> FEATURE:
<223> OTHER INFORMATION: Synthetic; BC32; 5' Amino Modifier C6

<400> SEQUENCE: 12
tcgtcggcag cgtcagatgt gtacactcaa ccagbaaaaa aaaaaaaaaa aaaaaaaaaa        60

<210> SEQ ID NO 13
<211> LENGTH: 60
<212> TYPE: DNA
<213> ORGANISM: Artificial Sequence
<220> FEATURE:
<223> OTHER INFORMATION: Synthetic; BC33; 5' Amino Modifier C6

<400> SEQUENCE: 13
tcgtcggcag cgtcagatgt gtagctgtgt acagbaaaaa aaaaaaaaaa aaaaaaaaaa        60

<210> SEQ ID NO 14
<211> LENGTH: 60
<212> TYPE: DNA
<213> ORGANISM: Artificial Sequence
<220> FEATURE:
<223> OTHER INFORMATION: Synthetic; BC34; 5' Amino Modifier C6

<400> SEQUENCE: 14
tcgtcggcag cgtcagatgt gtattgcgtc gcagbaaaaa aaaaaaaaaa aaaaaaaaaa        60

<210> SEQ ID NO 15
<211> LENGTH: 60
<212> TYPE: DNA
<213> ORGANISM: Artificial Sequence
<220> FEATURE:
<223> OTHER INFORMATION: Synthetic; BC35; 5' Amino Modifier C6

<400> SEQUENCE: 15
tcgtcggcag cgtcagatgt gtaatatgag acagbaaaaa aaaaaaaaaa aaaaaaaaaa        60

<210> SEQ ID NO 16
<211> LENGTH: 60
<212> TYPE: DNA
<213> ORGANISM: Artificial Sequence
<220> FEATURE:
<223> OTHER INFORMATION: Synthetic; BC36; 5' Amino Modifier C6

<400> SEQUENCE: 16
tcgtcggcag cgtcagatgt gtacacctca gcagbaaaaa aaaaaaaaaa aaaaaaaaaa        60

<210> SEQ ID NO 17
<211> LENGTH: 60
<212> TYPE: DNA
<213> ORGANISM: Artificial Sequence
<220> FEATURE:
<223> OTHER INFORMATION: Synthetic; BC37; 5' Amino Modifier C6

<400> SEQUENCE: 17
tcgtcggcag cgtcagatgt gtagctactt ccagbaaaaa aaaaaaaaaa aaaaaaaaaa        60

<210> SEQ ID NO 18
<211> LENGTH: 60
```

```
<212> TYPE: DNA
<213> ORGANISM: Artificial Sequence
<220> FEATURE:
<223> OTHER INFORMATION: Synthetic; BC38; 5' Amino Modifier C6

<400> SEQUENCE: 18
tcgtcggcag cgtcagatgt gtatgggagc tcagbaaaaa aaaaaaaaaa aaaaaaaaaa      60

<210> SEQ ID NO 19
<211> LENGTH: 60
<212> TYPE: DNA
<213> ORGANISM: Artificial Sequence
<220> FEATURE:
<223> OTHER INFORMATION: Synthetic; BC39; 5' Amino Modifier C6

<400> SEQUENCE: 19
tcgtcggcag cgtcagatgt gtaatccggc acagbaaaaa aaaaaaaaaa aaaaaaaaaa      60

<210> SEQ ID NO 20
<211> LENGTH: 60
<212> TYPE: DNA
<213> ORGANISM: Artificial Sequence
<220> FEATURE:
<223> OTHER INFORMATION: Synthetic; BC40; 5' Amino Modifier C6

<400> SEQUENCE: 20
tcgtcggcag cgtcagatgt gtaccgttat gcagbaaaaa aaaaaaaaaa aaaaaaaaaa      60

<210> SEQ ID NO 21
<211> LENGTH: 60
<212> TYPE: DNA
<213> ORGANISM: Artificial Sequence
<220> FEATURE:
<223> OTHER INFORMATION: Synthetic; REAP_BC41_v4; 3' Amino Modifier

<400> SEQUENCE: 21
tcgtcggcag cgtcagatgt gtaggtaatg tcagbaaaaa aaaaaaaaaa aaaaaaaaaa      60

<210> SEQ ID NO 22
<211> LENGTH: 60
<212> TYPE: DNA
<213> ORGANISM: Artificial Sequence
<220> FEATURE:
<223> OTHER INFORMATION: Synthetic; REAP_BC42_v4; 3' Amino Modifier

<400> SEQUENCE: 22
tcgtcggcag cgtcagatgt gtataagcca ccagbaaaaa aaaaaaaaaa aaaaaaaaaa      60

<210> SEQ ID NO 23
<211> LENGTH: 60
<212> TYPE: DNA
<213> ORGANISM: Artificial Sequence
<220> FEATURE:
<223> OTHER INFORMATION: Synthetic; REAP_BC43_v4; 3' Amino Modifier

<400> SEQUENCE: 23
tcgtcggcag cgtcagatgt gtaaccgaac acagbaaaaa aaaaaaaaaa aaaaaaaaaa      60

<210> SEQ ID NO 24
<211> LENGTH: 60
<212> TYPE: DNA
<213> ORGANISM: Artificial Sequence
<220> FEATURE:
<223> OTHER INFORMATION: Synthetic; REAP_BC44_v4; 3' Amino Modifier

<400> SEQUENCE: 24
```
tcgtcggcag cgtcagatgt gtacgactct tcagbaaaaa aaaaaaaaaa aaaaaaaaaa    60

<210> SEQ ID NO 25
<211> LENGTH: 60
<212> TYPE: DNA
<213> ORGANISM: Artificial Sequence
<220> FEATURE:
<223> OTHER INFORMATION: Synthetic; REAP_BC45_v4; 3' Amino Modifier

<400> SEQUENCE: 25
tcgtcggcag cgtcagatgt gtagtttgtg gcagbaaaaa aaaaaaaaaa aaaaaaaaaa    60

<210> SEQ ID NO 26
<211> LENGTH: 60
<212> TYPE: DNA
<213> ORGANISM: Artificial Sequence
<220> FEATURE:
<223> OTHER INFORMATION: Synthetic; REAP_BC46_v4; 3' Amino Modifier

<400> SEQUENCE: 26
tcgtcggcag cgtcagatgt gtatagacga ccagbaaaaa aaaaaaaaaa aaaaaaaaaa    60

<210> SEQ ID NO 27
<211> LENGTH: 60
<212> TYPE: DNA
<213> ORGANISM: Artificial Sequence
<220> FEATURE:
<223> OTHER INFORMATION: Synthetic; REAP_BC47_v4; 3' Amino Modifier

<400> SEQUENCE: 27
tcgtcggcag cgtcagatgt gtaacgcttg gcagbaaaaa aaaaaaaaaa aaaaaaaaaa    60

<210> SEQ ID NO 28
<211> LENGTH: 60
<212> TYPE: DNA
<213> ORGANISM: Artificial Sequence
<220> FEATURE:
<223> OTHER INFORMATION: Synthetic; REAP_BC48_v4; 3' Amino Modifier

<400> SEQUENCE: 28
tcgtcggcag cgtcagatgt gtacgctaca tcagbaaaaa aaaaaaaaaa aaaaaaaaaa    60

<210> SEQ ID NO 29
<211> LENGTH: 60
<212> TYPE: DNA
<213> ORGANISM: Artificial Sequence
<220> FEATURE:
<223> OTHER INFORMATION: Synthetic; REAP_BC49_v4; 3' Amino Modifier

<400> SEQUENCE: 29
tcgtcggcag cgtcagatgt gtagaaagac acagbaaaaa aaaaaaaaaa aaaaaaaaaa    60

<210> SEQ ID NO 30
<211> LENGTH: 60
<212> TYPE: DNA
<213> ORGANISM: Artificial Sequence
<220> FEATURE:
<223> OTHER INFORMATION: Synthetic; REAP_BC50_v4; 3' Amino Modifier

<400> SEQUENCE: 30
tcgtcggcag cgtcagatgt gtatttgcgt ccagbaaaaa aaaaaaaaaa aaaaaaaaaa    60

<210> SEQ ID NO 31
<211> LENGTH: 60
<212> TYPE: DNA
<213> ORGANISM: Artificial Sequence

```
<220> FEATURE:
<223> OTHER INFORMATION: Synthetic; REAP_BC51_v4; 3' Amino Modifier

<400> SEQUENCE: 31
tcgtcggcag cgtcagatgt gtaatggtcg ccagbaaaaa aaaaaaaaaa aaaaaaaaaa      60

<210> SEQ ID NO 32
<211> LENGTH: 60
<212> TYPE: DNA
<213> ORGANISM: Artificial Sequence
<220> FEATURE:
<223> OTHER INFORMATION: Synthetic; REAP_BC52_v4; 3' Amino Modifier

<400> SEQUENCE: 32
tcgtcggcag cgtcagatgt gtacgacata gcagbaaaaa aaaaaaaaaa aaaaaaaaaa      60

<210> SEQ ID NO 33
<211> LENGTH: 60
<212> TYPE: DNA
<213> ORGANISM: Artificial Sequence
<220> FEATURE:
<223> OTHER INFORMATION: Synthetic; REAP_BC53_v4; 3' Amino Modifier

<400> SEQUENCE: 33
tcgtcggcag cgtcagatgt gtagattcgc tcagbaaaaa aaaaaaaaaa aaaaaaaaaa      60

<210> SEQ ID NO 34
<211> LENGTH: 60
<212> TYPE: DNA
<213> ORGANISM: Artificial Sequence
<220> FEATURE:
<223> OTHER INFORMATION: Synthetic; REAP_BC54_v4; 3' Amino Modifier

<400> SEQUENCE: 34
tcgtcggcag cgtcagatgt gtatccagat acagbaaaaa aaaaaaaaaa aaaaaaaaaa      60

<210> SEQ ID NO 35
<211> LENGTH: 60
<212> TYPE: DNA
<213> ORGANISM: Artificial Sequence
<220> FEATURE:
<223> OTHER INFORMATION: Synthetic; REAP_BC55_v4; 3' Amino Modifier

<400> SEQUENCE: 35
tcgtcggcag cgtcagatgt gtaactactg tcagbaaaaa aaaaaaaaaa aaaaaaaaaa      60

<210> SEQ ID NO 36
<211> LENGTH: 60
<212> TYPE: DNA
<213> ORGANISM: Artificial Sequence
<220> FEATURE:
<223> OTHER INFORMATION: Synthetic; REAP_BC56_v4; 3' Amino Modifier

<400> SEQUENCE: 36
tcgtcggcag cgtcagatgt gtacgggaac gcagbaaaaa aaaaaaaaaa aaaaaaaaaa      60

<210> SEQ ID NO 37
<211> LENGTH: 60
<212> TYPE: DNA
<213> ORGANISM: Artificial Sequence
<220> FEATURE:
<223> OTHER INFORMATION: Synthetic; REAP_BC57_v4; 3' Amino Modifier

<400> SEQUENCE: 37
tcgtcggcag cgtcagatgt gtagacctct ccagbaaaaa aaaaaaaaaa aaaaaaaaaa      60
```

<210> SEQ ID NO 38
<211> LENGTH: 60
<212> TYPE: DNA
<213> ORGANISM: Artificial Sequence
<220> FEATURE:
<223> OTHER INFORMATION: Synthetic; REAP_BC58_v4; 3' Amino Modifier

<400> SEQUENCE: 38
tcgtcggcag cgtcagatgt gtattatgga acagbaaaaa aaaaaaaaaa aaaaaaaaaa    60

<210> SEQ ID NO 39
<211> LENGTH: 60
<212> TYPE: DNA
<213> ORGANISM: Artificial Sequence
<220> FEATURE:
<223> OTHER INFORMATION: Synthetic; REAP_BC59_v4; 3' Amino Modifier

<400> SEQUENCE: 39
tcgtcggcag cgtcagatgt gtaacagcaa ccagbaaaaa aaaaaaaaaa aaaaaaaaaa    60

<210> SEQ ID NO 40
<211> LENGTH: 60
<212> TYPE: DNA
<213> ORGANISM: Artificial Sequence
<220> FEATURE:
<223> OTHER INFORMATION: Synthetic; REAP_BC60_v4; 3' Amino Modifier

<400> SEQUENCE: 40
tcgtcggcag cgtcagatgt gtacgcaatt tcagbaaaaa aaaaaaaaaa aaaaaaaaaa    60

<210> SEQ ID NO 41
<211> LENGTH: 85
<212> TYPE: DNA
<213> ORGANISM: Artificial Sequence
<220> FEATURE:
<223> OTHER INFORMATION: Synthetic; P7+A1.3_11bpS3v4

<400> SEQUENCE: 41
caagcagaag acggcatacg agattcggcg tcgtgactgg agttcagacg tgtgctcttc    60
cgatctatgg gatgtcgtcg gcagc                                         85

<210> SEQ ID NO 42
<211> LENGTH: 84
<212> TYPE: DNA
<213> ORGANISM: Artificial Sequence
<220> FEATURE:
<223> OTHER INFORMATION: Synthetic; P7+A1.2_11bpS2v4

<400> SEQUENCE: 42
caagcagaag acggcatacg agatctaaac gggtgactgg agttcagacg tgtgctcttc    60
cgatctatgg gattcgtcgg cagc                                          84

<210> SEQ ID NO 43
<211> LENGTH: 83
<212> TYPE: DNA
<213> ORGANISM: Artificial Sequence
<220> FEATURE:
<223> OTHER INFORMATION: Synthetic; P7+A1.1_11bpS1v4

<400> SEQUENCE: 43
caagcagaag acggcatacg agatggttta ctgtgactgg agttcagacg tgtgctcttc    60
cgatctatgg gatcgtcggc agc                                           83

```
<210> SEQ ID NO 44
<211> LENGTH: 82
<212> TYPE: DNA
<213> ORGANISM: Artificial Sequence
<220> FEATURE:
<223> OTHER INFORMATION: Synthetic; P7+A1.4_11bpS0v4

<400> SEQUENCE: 44
caagcagaag acggcatacg agataaccgt aagtgactgg agttcagacg tgtgctcttc    60
cgatctatgg gtcgtcggca gc                                            82

<210> SEQ ID NO 45
<211> LENGTH: 56
<212> TYPE: DNA
<213> ORGANISM: Artificial Sequence
<220> FEATURE:
<223> OTHER INFORMATION: Synthetic; R1-P5

<400> SEQUENCE: 45
aatgatacgg cgaccaccga gatctacact ctttccctac acgacgctct tccgat        56
```

SAMPLE MULTIPLEXING FOR SINGLE-CELL RNA SEQUENCING

INCORPORATION BY REFERENCE TO ANY PRIORITY APPLICATIONS

The present application claims priority to U.S. Provisional Application No. 62/640,399, filed on Mar. 8, 2018. The contents of this related application is hereby expressly incorporated by reference in its entirety.

SEQUENCE LISTING IN ELECTRONIC FORMAT

The present application is being filed along with an Electronic Sequence Listing as an ASCII text file via EFS-Web. The Electronic Sequence Listing is provided as a file entitled CALTE138ASEQLIST.txt, created and last saved on Mar. 6, 2019, which is 10,099 bytes in size. The information in the Electronic Sequence Listing is incorporated herein by reference in its entirety.

BACKGROUND

Field

The present disclosure relates generally to the field of molecular biology, for example methods of tagging cells for use in single-cell RNA-sequencing (scRNA-seq) experiments.

Description of the Related Art

Massively parallelized single-cell RNA-sequencing (scRNA-seq) is transforming our view of complex tissues and yielding new insights into functional states of heterogeneous cell populations. Currently, individual scRNA-seq experiments can routinely probe the transcriptomes of more than ten thousand cells, and in the past year the first datasets approaching and exceeding one million cells have been reported. However, despite numerous technical breakthroughs that have increased cell capacity of many scRNA-seq platforms, researchers are at present limited in the number of samples that can be assayed. Many biological and therapeutic problems rely on finding genes or signals responsible for a phenotype of interest, but the enormous space of possible variables calls for screening hundreds, or even thousands, of conditions. At present, analyzing genetic, signaling, and drug perturbations (and their combinations) at scale with scRNA-seq is impeded by microfluidic device operation, high reagent costs, and batch effect. While a multiplexing method based on epitope expression has been developed, it can only be practically applied to about a dozen samples. The in silico demuxlet algorithm is more scalable but requires samples from distinct genetic backgrounds. There is a need for systems and methods of cell tagging which can enable the massive cell capacity of scRNA-seq to be effectively leveraged to analyze and compare large numbers of cell populations.

SUMMARY

Disclosed herein include methods for tagging a plurality of samples. In some embodiments, the method comprises: for each sample of a plurality of samples: (a) incubating one or more amine-modified sample tags with a first heterobifunctional linker to generate one or more tetrazine-modified sample tags; and (b) incubating the one or more tetrazine-modified sample tags of step (a) with (i) a second heterobifunctional linker, and (ii) a sample comprising one or more particles, to generate particles tagged with one or more sample tags. In some embodiments, the first heterobifunctional linker comprises a first reactive group and a second reactive group, wherein the first reactive group of the first heterobifunctional linker comprises an amine-reactive functional group and wherein the second reactive group of first heterobifunctional linker comprises a tetrazine moiety. In some embodiments, the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety.

Disclosed herein include methods for tagging a plurality of samples. In some embodiments, the method comprises: for each sample of a plurality of samples: (a) providing one or more tetrazine-modified sample tags; and (b) incubating one or more tetrazine-modified sample tags (i) a second heterobifunctional linker, and (ii) a sample comprising one or more particles, to generate particles tagged with one or more sample tags. In some embodiments, the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety.

Disclosed herein include sample multiplexing methods for single-cell RNA sequencing (scRNA-Seq). In some embodiments, the method comprises, prior to performing scRNA-Seq analysis of a plurality of samples, for each sample: (a) incubating one or more amine-modified sample tags with a first heterobifunctional linker to generate one or more tetrazine-modified sample tags; and (b) incubating the one or more tetrazine-modified sample tags of step (a) with (i) a second heterobifunctional linker, and (ii) a sample comprising one or more particles, to generate particles tagged with one or more sample tags. In some embodiments, the first heterobifunctional linker comprises a first reactive group and a second reactive group, wherein the first reactive group of the first heterobifunctional linker comprises an amine-reactive functional group and wherein the second reactive group of first heterobifunctional linker comprises a tetrazine moiety. In some embodiments, the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety.

Disclosed herein include sample multiplexing methods for single-cell RNA sequencing (scRNA-Seq). In some embodiments, the method comprises, prior to performing scRNA-Seq analysis of a plurality of samples, for each sample: (a) providing one or more tetrazine-modified sample tags; and (b) incubating one or more tetrazine-modified sample tags with (i) a second heterobifunctional linker, and (ii) a sample comprising one or more particles, to generate particles tagged with one or more sample tags. In some embodiments, the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety.

Disclosed herein include methods of tagging a plurality of samples. In some embodiments, the method comprises, for each sample of a plurality of samples: (a) incubating one or more sample tags with a reagent to generate one or more functionalized sample tags via a click chemistry reaction; and (b) incubating the one or more functionalized sample tags of step (a) with a sample comprising one or more particles, to generate particles tagged with one or more sample tags.

Disclosed herein include sample multiplexing methods for scRNA-Seq. In some embodiments, the method comprises, prior to performing scRNA-Seq analysis of a plurality of samples, for each sample: (a) incubating one or more sample tags with a reagent to generate one or more functionalized sample tags via a click chemistry reaction; and (b) incubating the one or more functionalized sample tags of step (a) with a sample comprising one or more particles, to generate particles tagged with one or more sample tags.

Disclosed herein include methods of tagging a plurality of samples. In some embodiments, the method comprises, for each sample of a plurality of samples: (a) incubating anchor sample tags with a reagent to generate functionalized anchor sample tags via a click chemistry reaction; and (b) incubating the functionalized anchor sample tags of step (a) with a sample comprising one or more particles, to generate particles tagged with anchor sample tags; wherein said anchor sample tags comprise a component that can bind to one or more sample tags. Disclosed herein include sample multiplexing methods for scRNA-Seq. In some embodiments, the method comprises, prior to performing scRNA-Seq analysis of a plurality of samples, for each sample: (a) incubating anchor sample tags with a reagent to generate functionalized anchor sample tags via a click chemistry reaction; and (b) incubating the functionalized anchor sample tags of step (a) with a sample comprising one or more particles, to generate particles tagged with anchor sample tags; wherein said anchor sample tags comprise a component that can bind to one or more sample tags. In some embodiments, step (b) further comprises incubating the particles tagged with the anchor sample tags with one or more sample tags to generate particles tagged with one or more sample tags.

Disclosed herein include methods of tagging a plurality of samples. In some embodiments, the method comprises, for each sample of a plurality of samples: (a) incubating one or more amine-modified sample tags with a first heterobifunctional linker to generate one or more DBCO-modified sample tags; and (b) incubating the one or more DBCO-modified sample tags of step (a) with (i) a second heterobifunctional linker, and (ii) a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety; and wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a DBCO-reactive moiety.

Disclosed herein include sample multiplexing methods for scRNA-Seq. In some embodiments, the method comprises, prior to performing scRNA-Seq analysis of a plurality of samples, for each sample: (a) incubating one or more amine-modified sample tags with a first heterobifunctional linker to generate one or more DBCO-modified sample tags; and (b) incubating the one or more DBCO-modified sample tags of step (a) with (i) a second heterobifunctional linker, and (ii) a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety; and wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a DBCO-reactive moiety.

Disclosed herein include methods of tagging a plurality of samples. In some embodiments, the method comprises, for each sample of a plurality of samples: (a) incubating one or more amine-modified sample tags with a first heterobifunctional linker to generate one or more DBCO-modified sample tags; and (b) incubating the one or more DBCO-modified sample tags of step (a) with a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety.

Disclosed herein include sample multiplexing methods for scRNA-Seq. In some embodiments, the method comprises, prior to performing scRNA-Seq analysis of a plurality of samples, for each sample: (a) incubating one or more amine-modified sample tags with a first heterobifunctional linker to generate one or more DBCO-modified sample tags; and (b) incubating the one or more DBCO-modified sample tags of step (a) with a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety.

In some embodiments, the DBCO-reactive moiety is an azide group. In some embodiments, the amine-reactive functional group is selected from the group comprising an isothiocyanate, isocyanate, acyl azide, N-hydroxysuccinimide (NHS) ester, sulfonyl chloride, aldehyde, glyoxal, epoxide, carbonate, arylating agent, imidoester, carbodimide, and derivatives thereof. In some embodiments, the amine-reactive functional group is N-hydroxysuccinimide (NHS) ester. In some embodiments, the first heterobifunctional linker is DBCO-NHS. In some embodiments, the second heterobifunctional linker is azide-NHS.

In some embodiments, the amine-reactive functional group is selected from the group comprising an isothiocyanate, isocyanate, acyl azide, N-hydroxysuccinimide (NHS) ester, sulfonyl chloride, aldehyde, glyoxal, epoxide, carbonate, arylating agent, imidoester, carbodimide, and derivatives thereof. In some embodiments, the tetrazine-reactive moiety is selected from the group comprising trans-cyclooctene (TCO), dibenzocyclooctyne (DBCO), difluorinated cyclooctyne (DIFO), bicyclononyne (BCN), dibenzocyclooctyne (DICO) and derivatives thereof. In some embodiments, the tetrazine moiety is selected from the group comprising 1,2,3,4-tetrazine, 1,2,3,5-tetrazine, 1,2,4,5-tetrazine, and derivatives thereof. In some embodiments, the tetrazine moiety is methyltetrazine (MTZ). In some embodiments, the amine-reactive functional group is N-hydroxysuccinimide (NHS) ester. In some embodiments, the tetrazine-reactive moiety is trans-cyclooctene (TCO). In some embodiments, the first heterobifunctional linker is NHS-MTZ. In some embodiments, the second heterobifunctional linker is NHS-TCO.

In some embodiments, the one or more amine-modified sample tags comprises an oligonucleotide, wherein the oligonucleotide comprises a 3' amine, a 5' amine, or combination thereof. In some embodiments, the sample tag comprises a DNA oligonucleotide. In some embodiments, the sample tag comprises an RNA oligonucleotide. In some embodiments, the sample tag is single-stranded oligonucleotide. In some embodiments, the sample tag is double-stranded oligonucleotide. In some embodiments, the sample tag is about 10 nucleotides to about 500 nucleotides in length. In some embodiments, the sample tag comprises a capture sequence. In some embodiments, the capture sequence is a poly(dA) region at the 5' end of the oligonucleotide. In some embodiments, the capture sequence is a poly(dA) region at the 3'end of the oligonucleotide. In some embodiments, the poly(dA) region is about 10 nucleotides to about 100 nucleotides in length. In some embodiments, the capture sequence binds the capture-binding sequence of a component of a library preparation kit, wherein a library preparation kit comprises a cDNA library preparation kit, a genomic library preparation kit, a sequencing library preparation kit, and any combination thereof. In some embodiments, the sample tag comprises a constant region. In some embodiments, the constant region comprises a sequence bound by a library preparation reagent, by a sequencing platform reagent, and any combination thereof. In some embodiments, the constant region comprises a PCR primer region. In some embodiments, the PCR primer region comprises all or a portion of a binding site for a sequencing primer. In some embodiments, the PCR primer region comprises all or a portion of a Read 1 sequencing primer annealing site. In some embodiments, the sample tag comprises a barcode sequence. In some embodiments, the barcode sequence is about 1 nucleotide to about 200 nucleotides in length. In some embodiments, the barcode sequence is about 10 nucleotides in length.

In some embodiments, the one or more sample tags comprise a sample tag set. In some embodiments, the sample tag set comprises a single sample tag. In some embodiments, the sample tag set comprises a plurality of sample tags with distinct barcode sequences. In some embodiments, the sample tag set comprises 2 sample tags with distinct barcode sequences. In some embodiments, the sample tag set comprises 3 sample tags with distinct barcode sequences. In some embodiments, the sample tag set comprises 4 sample tags with distinct barcode sequences. In some embodiments, the sample tag set comprises 5 sample tags with distinct barcode sequences. In some embodiments, the sample tag set comprises 6 sample tags with distinct barcode sequences. In some embodiments, the sample tag set comprises 7 sample tags with distinct barcode sequences. In some embodiments, the sample tag set comprises 8 or more sample tags with distinct barcode sequences. In some embodiments, one or more particles of each sample of the plurality of samples is labeled with a unique sample tag set.

In some embodiments, each of a plurality of samples is labeled with a wholly unique sample tag set. In some embodiments, each of a plurality of samples is labeled with a partially unique sample tag set. In some embodiments, the combined barcode sequence(s) of all sample tag(s) within a unique sample tag set are distinct from the combined barcode sequence(s) of all sample tag(s) of every other sample tag set in a plurality of sample tag sets. In some embodiments, the one or more sample tags is selected from a sample tag pool. In some embodiments, the sample tag pool comprises all of the sample tags with distinct barcode sequences. In some embodiments, the number of unique sample tag sets within a plurality of sample tag sets is represented by the binomial coefficient $$\binom{n}{k},$$

wherein n is the number of sample tags in the sample tag pool and k is the number of sample tags in a unique sample tag set.

In some embodiments, the plurality of samples comprises 2 or more samples. In some embodiments, the plurality of samples comprises more than 10 samples. In some embodiments, the plurality of samples comprises more than 50 samples. In some embodiments, the plurality of samples comprises more than 100 samples. In some embodiments, the plurality of samples comprises more than 500 samples. In some embodiments, the plurality of samples comprises more than 1,000 samples. In some embodiments, the plurality of samples comprises more than 2,000 samples. In some embodiments, the plurality of samples comprises more than 5,000 samples. In some embodiments, the plurality of samples comprises more than 10,000 samples. In some embodiments, the sample comprises about 1 cell to about 100,000 cells. In some embodiments, the sample comprises about 1 cell to about 1,000,000 cells. In some embodiments, one or more of the samples is a patient sample. In some embodiments, the one or more particles comprise one or more synthetic particles. In some embodiments, the one or more synthetic particles comprise beads, synthetic cells, lipid droplets, and any combination thereof. In some embodiments, the beads comprise magnetic beads, glass beads, cellulose beads, epichlorohydrin-cross-linked-dextran beads, polyacrylamide beads, agarose beads, polystyrene beads, gel-based beads, and any combination thereof. In some embodiments, the beads are chemically functionalized. In some embodiments, the one or more particles comprise one or more biological particles. In some embodiments, the one or more biological particles comprise one or more of prokaryotic cells, eukaryotic cells, viral particles, exosomes, protoplasts, microvesicles, and any combination thereof. In some embodiments, the one or more biological particles comprise one or more cells. In some embodiments, the one or more cells are live immediately prior to step (a). In some embodiments, the one or more cells have undergone fixation prior to step (a). In some embodiments, the one or more cells are prokaryotic cells. In some embodiments, the one or more cells are eukaryotic cells. In some embodiments, the one or more cells are selected from the group comprising fungal cells, plant cells, insect cells, and any combination thereof. In some embodiments, the one or more cells are mammalian cells.

In some embodiments, one or more samples of the plurality of samples are exposed to one or more perturbations prior to step (a). In some embodiments, the one or more perturbations comprises an environmental condition, a small molecule, an agent, or any combination thereof. In some embodiments, two or more samples of the plurality of samples are exposed to different concentrations of the same agent or the same small molecule prior to step (a). In some embodiments, the environmental condition is physical, temporal, chemical, biological, or any combination thereof. In some embodiments, the agent comprises one or more of cytokines, hormones, growth factors, toxins, inflammatory molecules, oncogene products, signal transduction molecules, or any combination thereof. In some embodiments, the agent is an agent capable of modulating expression of a gene. In some embodiments, the agent capable of modulating expression of a gene is a CRISPR system, RNAi, TALE, or zinc finger protein, or any combination thereof. In some embodiments, the agent capable of modulating expression of a gene is inducible.

In some embodiments, step (a) is performed for a period of about 10 minutes to about 240 minutes. In some embodiments, step (a) is performed for a period of about 180 minutes. In some embodiments, step (a) is performed for a period of about 90 minutes. In some embodiments, step (a) comprises the addition of one or more further aliquots of the first heterobifunctional linker during the incubation. In some embodiments, step (a) is performed at a temperature of about 20° C. In some embodiments step (a) is performed at a temperature of about 37° C. to about 45° C. In some embodiments, step (a) is performed in the presence of dimethyl sulfoxide (DMSO). In some embodiments, step (a) comprises ethanol precipitation of the one or more tetrazine-modified sample tags at the end of the incubation. In some embodiments, step (a) is performed immediately prior to step (b). In some embodiments, the one or more tetrazine-modified sample tags of step (a) were frozen prior to step (b).

In some embodiments, step (b) is a one-pot, two-step reaction. In some embodiments, step (b) comprises the in situ generation of amine-reactive sample tags via inverse-electron demand diels-alder (IEDDA) chemistry. In some embodiments, the amine-reactive sample tags comprise an amine-reactive functional group. In some embodiments, nucleophilic attack of exposed primary amines on the one or more particles by the amine-reactive sample tags generates particles tagged with one or more sample tags. In some embodiments, step (b) is performed in the dark. In some embodiments, step (b) is performed under physiological aqueous conditions. In some embodiments, step (b) is performed under methanol fixation conditions. In some embodiments, step (b) is performed in a buffer devoid of buffer components containing primary amines. In some embodiments, step (b) is performed in a buffer compatible with NHS-ester conjugation. In some embodiments, step (b) is performed for a period of about 10 minutes to about 180 minutes. In some embodiments, step (b) is performed for a period of about 30 minutes. In some embodiments, step (b) is performed for a period of about 20 minutes. In some embodiments, step (b) is performed at a temperature of about 20° C. In some embodiments, step (b) is performed at a temperature of about 4° C. In some embodiments, step (b) comprises: i) preincubation of the one or more tetrazine-modified sample tags and the second heterobifunctional linker; and ii) addition of the a sample comprising one or more molecules to the one or more tetrazine-modified sample tags and the second heterobifunctional linker from (i) to generate particles tagged with one or more sample tags. In some embodiments, the (i) preincubation is performed for a period of about 5 minutes. In some embodiments, step (b) further comprises the sub step of: iii) quenching the reaction. In some embodiments, the (iii) quenching comprises the addition of methyltetrazine-DBCO. In some embodiments, the (iii) quenching comprises the addition of a primary amine. In some embodiments, the primary amine comprises Tris-HCl. In some embodiments, the (iii) quenching comprises the addition of a methyltetrazine-derivatized molecule. In some embodiments, the methyltetrazine-derivatized molecule comprises MTZ-DBCO, a MTZ-amine, a MTZ-carboxylic acid, and any combination thereof. In some embodiments, the (iii) quenching comprises the addition of a DBCO-derivatized molecule. In some embodiments, the DBCO-derivatized molecule comprises MTZ-DBCO, DBCO-amine, DBCO-carboxylic acid, and any combination thereof. In some embodiments, the (iii) quenching is performed for a period of about 5 minutes. In some embodiments, step (b) further comprises the sub step of: iv) pooling the particles tagged with one or more sample tags of the plurality of samples.

In some embodiments, the one or more particles tagged with one or more sample tags comprise nucleic acids. In some embodiments, the method further comprises the step of: (c) sequence analysis for each sample of the plurality of samples. In some embodiments, (c) sequence analysis comprises i) sequence analysis of the one or more sample tags, and (ii) sequence analysis of nucleic acids of the one or more particles tagged with said one or more sample tags. In some embodiments, the sequence analysis comprises single cell sequence analysis. In some embodiments, the sequence analysis comprises epitope density profiling. In some embodiments, the sequence analysis comprises RNA sequence analysis. In some embodiments, the RNA sequence analysis comprises whole transcriptome sequencing. In some embodiments, the RNA sequence analysis comprises single-cell RNA sequencing (scRNA-Seq). In some embodiments, the RNA sequence analysis comprises targeted RNA sequencing. In some embodiments, targeted RNA sequencing comprises targeted mRNA sequencing. In some embodiments, targeted RNA sequencing comprises targeted non-coding RNA sequencing. In some embodiments, the RNA sequence analysis comprises ultra-low-input scRNA-seq. In some embodiments, the sequence analysis comprises DNA sequence analysis. In some embodiments, the DNA sequence analysis comprises whole genome sequencing, whole exome sequencing, targeted gene sequencing, whole regulome sequencing, sequencing-based methylation analysis, sequencing-based breakpoint detection, ChIP sequencing, or any combination thereof.

In some embodiments, sequence analysis comprises sample demultiplexing, wherein sample demultiplexing comprises associating the results of sequence analysis of the one or more particles with the sample of origin based on a sequence analysis of the one or more sample tags. In some embodiments, the sequence analysis of the one or more sample tags comprises the determining the sequences of the one or more sample tags. In some embodiments, determining the sequences of the one or more sample tags comprises determining the barcode sequences of the one or more sample tags, thereby identifying the sample tag set. In some embodiments, the sequence analysis comprises single cell sequence analysis, wherein sequence analysis of the one or more sample tags comprises determining a sum of sample tag counts for a tagged cell, wherein the sum of sample tag counts correlates with the size of a cell tagged with the sample tags. In some embodiments, the sequence analysis comprises single cell sequence analysis, wherein the presence of barcode sequences of two or more sample tag sets for a single sample and/or a single cell indicates a doublet event. In some embodiments, the sequence analysis comprises single cell sequence analysis, wherein the sum of sample tag counts for a tagged cell correlates with the size of the tagged cell. In some embodiments, the cost of sequence analysis is reduced by at least 5% as compared to a sequence analysis performed in the absence of said or more sample tags. In some embodiments, the sequence analysis yields reduced batch effects as compared to a sequence analysis performed in the absence of said or more sample tags. In some embodiments, the method does not comprise epitope labeling and/or genetic manipulation prior to step (a).

Disclosed herein are kits for tagging a plurality of samples. In some embodiments, the kit comprises: one or more amine-modified sample tags, a first heterobifunctional linker, and a second heterobifunctional linker; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a tetrazine moiety; and wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety. Disclosed herein are kits for tagging a plurality of samples. In some embodiments, the kit comprises: one or more tetrazine-modified sample tags, and a second heterobifunctional linker; wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety. In some embodiments, the tetrazine moiety is methyltetrazine (MTZ). In some embodiments, the amine-reactive functional group is N-hydroxysuccinimide (NHS) ester. In some embodiments, the tetrazine-reactive moiety is trans-cyclooctene (TCO). In some embodiments, the first heterobifunctional linker is NHS-MTZ. In some embodiments, the second heterobifunctional linker is NHS-TCO. Disclosed herein are strain-promoted alkyne-azide cycloaddition (SPAAC) kits for tagging a plurality of samples, comprising: one or more amine-modified sample tags; NHS-Azide; and NHS-DBCO. Disclosed herein are kits for tagging a plurality of samples, comprising: one or more amine-modified sample tags; and NHS-DBCO. Also disclosed herein are kits for tagging a plurality of samples, comprising: one or more DBCO-modified sample tags. In some embodiments, the one or more amine-modified sample tags comprises an oligonucleotide, wherein the oligonucleotide comprises a 3' amine, a 5' amine, or combination thereof. In some embodiments, the sample tag comprises a DNA oligonucleotide. In some embodiments, the sample tag comprises an RNA oligonucleotide. In some embodiments, the sample tag is single-stranded oligonucleotide. In some embodiments, the sample tag is double-stranded oligonucleotide. In some embodiments, the sample tag is about 10 nucleotides to about 500 nucleotides in length. In some embodiments, the sample tag comprises a capture sequence. In some embodiments, the capture sequence binds the capture-binding sequence of a component of a library preparation kit, wherein a library preparation kit comprises a cDNA library preparation kit, a genomic library preparation kit, a sequencing library preparation kit, and any combination thereof. In some embodiments, the capture sequence is a poly(dA) region at the 5' end of the oligonucleotide. In some embodiments, the capture sequence is a poly(dA) region at the 3'end of the oligonucleotide. In some embodiments, the poly(dA) region is about 10 nucleotides to about 100 nucleotides in length. In some embodiments, the sample tag comprises a constant region. In some embodiments, the constant region comprises a sequence bound by a library preparation reagent, by a sequencing platform reagent, and any combination thereof. In some embodiments, the constant region comprises a PCR primer region. In some embodiments, the PCR primer region comprises all or a portion of the binding site for a sequencing primer. In some embodiments, the PCR primer region comprises all or a portion of a Read 1 sequencing primer annealing site. In some embodiments, the sample tag comprises a barcode sequence. In some embodiments, the barcode sequence is about 1 nucleotide to about 200 nucleotides in length. In some embodiments, the barcode sequence is about 10 nucleotides in length.

BRIEF DESCRIPTION OF THE DRAWINGS

FIGS. 1A-1B show schematic illustrations of non-limiting exemplary embodiments of the sample tagging method of the disclosure.

FIG. 3A depicts a schematic illustration of the experimental factors titrated against one another in a 96-Plex scRNA-Seq experiment. Four experimental factors (EGF/bFGF, BMP-4, Decitabine/Scriptaid, and Retinoic acid) were titrated against one another to produce an array of 96 unique perturbations. FIG. 3B depicts a schematic illustration of the one-pot, two-step reaction with MTZ-DNA and NHS-TCO labeled cells with sample-specific tags. FIG. 3C depicts a schematic illustration of neural stem cells subjected to a 96-plex array of growth conditions that were dual-labeled with a unique pair of sample tags. FIG. 3D depicts a t-SNE projection plot of 21,232 cells from the 96-plex perturbation experiment. FIG. 3E depicts a visualization of cell populations produced by each experimental condition. Each t-SNE projection plot corresponds to a given EGF/bFGF concentration against a series of retinoic acid or Scriptaid/Decitabine concentrations and displays eight samples colored by BMP-4 concentration.

FIG. 4 shows a schematic illustration of the organization of the 96-plex perturbation experiment Matrix entries correspond to the number of cells recovered from each sample FIG. 5A depicts cluster occupancy (below) versus experimental condition (above), shown as number of cells detected (top panel) or the relative abundance of cells assigned to each cluster in each sample (bottom panel). FIG. 5B depicts principal component analysis (PCA) of the relative cluster abundance matrix from FIG.

5A. Each point represents a cell population from one of 96 experimental conditions, revealing patterns of influence for each experimental factor (highlighted). FIG. 5C depicts t-SNE projection plots showing that five conditions map specifically to cluster 15, characterized by Hes5 expression.

FIG. 7A depicts a heatmap showing 3,768 detected cells originating from four methanol-fixed samples each labeled by a pair of sample-specific tags. FIG. 7B depicts a t-SNE visualization of sample tag data colored by k-means clustering (k=4).

FIGS. 9A-9E depict data related to the 96-plex scRNA-seq experiment FIG. 9A depicts four cellular perturbants (EGF/bFGF, BMP4, Decitabine/Scriptaid, and retinoic acid) were titrated against one another to produce an array of 96 unique growth conditions. FIG. 9B depicts Prior to scRNA-seq, a one-pot, two-step reaction with MTZ-DNA and NHS-TCO labeled cells with sample-specific ClickTags. FIG. 9C depicts Neural stem cells subjected to a 96-plex array of growth conditions were dual-labeled with a unique pair of ClickTags FIG. 9D depicts UMAP embedding of 21,191 cells from the 96-plex perturbation. Cluster assignments parallel population behavior driven by experimental conditions. FIG. 9E depicts Visualization of cell populations produced by each experimental condition. Each embedding corresponds to a given EGF/bFGF concentration against a series of BMP4 concentrations and displays six samples colored by retinoic acid or Scriptaid/Decitabine concentration.

FIG. 10A depicts yeast cells were fluorescently labeled in a one-pot, two-step reaction with NHS-TCO and MTZ-Cy5. Control reactions omitted NHS-TCO. FIG. 10B depicts fluorescence microscopy of yeast cells labeled with NHS-TCO and MTZ-Cy5 show labeling only in the presence of NHS-TCO cross-linker. FIG. 10C depicts activity assay for panels of methyltetrazine-activated ClickTags. MTZ-DNAs were reacted with TCO-Cy5 and the products separated by polyacrylamide gel electrophoresis. Lanes 1-12 are 3'-amine modified, while lanes 13 and 14 are 5'-amine modified.

FIGS. 12A-12J show data related to a proof-of-concept ClickTag labeling experiment. FIG. 12A depicts a heatmap showing 3,800 detected cells originating from four methanol-fixed samples, each labeled with a pair of sample-specific ClickTags. FIG. 12B depicts a UMAP visualization of ClickTag data colored by Louvain community detection. Four main clusters are observed, corresponding to the four individual samples as well as 4/2=6 small clusters corresponding to each possible combination of cell doublet originating from two different samples. FIG. 12C depicts a Scatter plot of counts for ClickTags 1 and 2, which were used to label the same sample. The low-count population (bottom-left) is background from droplets not containing cells from the sample, while the high-count population corresponds to positive cells from the sample, and displays a strong correlation between the two ClickTag counts (Pearson's correlation coefficient r=0.96). FIG. 12D depicts a "Barnyard plot" showing two ClickTags from separate samples. ClickTag labeling is orthogonal, with doublets identifiable as points away from the axes. FIG. 12E depicts Counts for ClickTag 1 from each cell in the experiment, ordered from highest to lowest and showing an inflection point between ClickTag 1 (+) and ClickTag 1 (−) cells. FIGS. 12F-12J show similar analysis for four samples of live cells labeled using the same procedure.

FIGS. 13A-13J depict data related to analysis of ClickTag "expression" from the four-sample multiplexing experiment shown in FIGS. 12A-12E. FIGS. 13A-13D show the sum of normalized, log-transformed ClickTag counts for each of the four samples. Each pair of unique ClickTags labels one cluster and exactly three sub-clusters (doublets). FIGS. 13E-13J show barnyard plots for pairs of ClickTags corresponding to the experimental design.

FIG. 14D shows a Scrublet algorithm was used to computationally identify 168 cell multiplets based on ClickTags. The doublets identified by scrublet were extracted and clustered. Violin plots for all six clusters are shown in FIG. 14E.

FIG. 15A depicts a barnyard plot depicting cDNA counts, colored by species as determined by CellRanger. FIG. 15B depicts correlation of gene expression for methanol-fixed mouse NSCs treated with ClickTags versus untreated, methanol-fixed cells. cDNA from live NSCs was also used for comparison against methanol-fixed, ClickTagged cells (FIG. 15C) or untagged, methanol-fixed cells (FIG. 15D). Gene expression is shown as average counts per cell for each mouse gene.

FIGS. 16A-16B depict violin plots for UMI and gene counts from cells identified as "human" by Cell Ranger, grouped according to sample identification shown in FIG. 20A. FIG. 16C depicts pairwise correlation of gene expression from all samples containing human cells. Gene expression is shown as average counts per cell for each human gene.

FIGS. 17A-17B depict violin plots for UMI and gene counts from cells identified as "mouse" by Cell Ranger, grouped according to sample identification shown in FIG. 20A. FIG. 17C depicts pairwise correlation of gene expression from all samples containing mouse cells. Gene expression is shown as average counts per cell for each mouse gene.

FIG. 18A depicts embedding of cDNA from all "human" singlet cells showing mixing of cells from samples with one/two ClickTags or three/four/five ClickTags, but separation of the two groups. FIG. 18B depicts clustering of the cells shown in FIG. 18A. FIG. 18C depicts correlation of gene expression for clusters shown in FIG. 18B, with each gene shown as the average counts per cell in each group. FIG. 18D depicts top differentially expressed genes for cluster 0, cells labeled with ½ ClickTags, colored as in FIG. 18A. FIG. 18E depicts top differentially expressed genes for cluster 1, cells labeled with three/four/five ClickTags, colored as in FIG. 18A.

FIG. 19A shows embedding of cDNA from all "mouse" singlet cells showing mixing of cells from samples with one/two ClickTags or three/four/five ClickTags, but separation of the two groups. FIG. 19B shows Clustering of the cells shown in FIG. 19A. FIG. 19C shows correlation of gene expression for clusters shown in FIG. 19B, with each gene shown as the average counts per cell in each group. FIG. 19D shows top differentially expressed genes for cluster 0, cells labeled with one/two ClickTags, colored as in FIG. 19A. FIG. 19E shows top differentially expressed genes for cluster 1, cells labeled with three/four/five Click-Tags, colored as in FIG. 19A.

FIG. 20A shows clustering and embedding of ClickTag data after filtering low-quality cells. FIG. 20B shows ClickTag embedding colored according to summed, normalized, and log-transformed ClickTag counts from each sample. FIG. 20C shows doublets as detected by Cell Ranger or Scrublet are found to predominantly label the same small sub-clusters on the ClickTag embedding. FIG. 20E shows suspected cell doublet sub-clusters were manually selected from t-SNE embedding using FlowJo cytometry analysis software, identifying 26 sub-clusters that appeared to arise from inter-sample doublets. FIG. 20F shows a Venn diagram showing agreement between all three doublet identification methods. FIG. 20G shows a human/mouse cDNA barnyard plot for all high-quality cells, colored according to Cell Ranger detection. Cell Ranger can only identify doublets between cells of different species, while ClickTag data can identify doublets between experimental samples regardless of species identity.

FIG. 21A depicts Violin plots generated from doublet sub-clusters manually isolated from a t-SNE embedding of ClickTag data shown in FIG. 20E. For comparison, singlet clusters are shown on the diagonal. Each of the 26 sub-clusters could be assigned to a specific doublet event between two well-defined samples, with the two remaining inter-sample doublet types (*) found to be filtered out during the quality control step described in FIG. 25. FIG. 21B depicts all ClickTag counts across all cells. In each sample, a distinct group of positively labeled cells can be distinguished from negative cells originating from other samples.

FIGS. 23A-23C depict data related to sample assignment for the 96-sample perturbation experiment. Thresholds were set using the maximum slope of the rank-UMI plot for each ClickTag across all cells as determined by the numpy gradient function. 21,223 cells (92%) were assigned to exactly two ClickTags (FIG. 23B), with 99.8% of those corresponding to a valid barcode combination from the experimental design. Only these cells were used for downstream analysis. Distribution of cells recovered across the experimental conditions are shown in FIG. 23C.

FIG. 24A shows Cluster occupancy versus experimental condition shown as number of cells (top) or relative abundance of cells assigned to each cluster for each sample (bottom). FIG. 24B shows PCA of relative cluster abundance matrix from FIG. 24A. Each point represents a cell population from one of 96 experimental conditions, revealing patterns of influence for each experimental factor (highlighted). FIGS. 24C-24D depict the dissection of heterogeneous cell populations by cluster and condition. Seven samples from conditions with low retinoic acid and lacking BMP4 yielded cell populations predominantly mapping to clusters 14 and 15, which are distinguished by unique marker genes including the neural differentiation markers Hes5 and Gadd45g (FIG. 24C). In FIG. 24D, similar segmentation is achieved for the highly proliferative cell states arising from samples treated with low BMP4 and high retinoic acid concentrations.

DETAILED DESCRIPTION

Figure 2A:
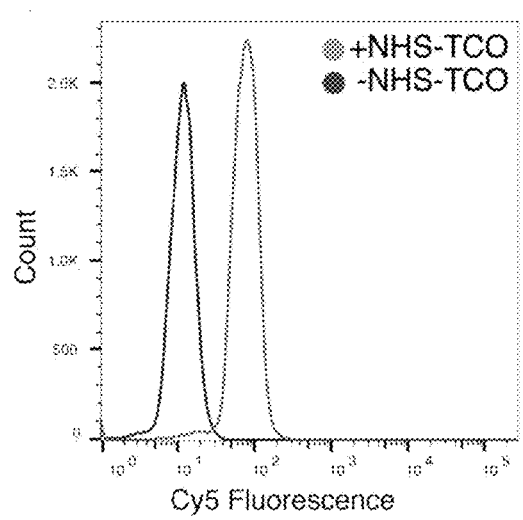
FIGS. 2A and 2B depicts exemplary direct yeast cell labeling with Inverse Electron-Demand Diels-Alder (IEDDA) chemistry. The fluorescent labeling of yeast cells was performed with NHS-TCO and MTZ-Cy5 (or in the absence of NHS-TCO as a control).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include methods for tagging a plurality of samples. In some embodiments, the method comprises: for each sample of a plurality of samples: (a) incubating one or more amine-modified sample tags with a first heterobifunctional linker to generate one or more tetrazine-modified sample tags; and (b) incubating the one or more tetrazine-modified sample tags of step (a) with (i) a second heterobifunctional linker, and (ii) a sample comprising one or more particles, to generate particles tagged with one or more sample tags. In some embodiments, the first heterobifunctional linker comprises a first reactive group and a second reactive group, wherein the first reactive group of the first heterobifunctional linker comprises an amine-reactive functional group and wherein the second reactive group of first heterobifunctional linker comprises a tetrazine moiety. In some embodiments, the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety.

Disclosed herein include methods for tagging a plurality of samples. In some embodiments, the method comprises: for each sample of a plurality of samples: (a) providing one or more tetrazine-modified sample tags; and (b) incubating one or more tetrazine-modified sample tags (i) a second heterobifunctional linker, and (ii) a sample comprising one or more particles, to generate particles tagged with one or more sample tags. In some embodiments, the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety.

Disclosed herein include sample multiplexing methods for single-cell RNA sequencing (scRNA-Seq). In some embodiments, the method comprises, prior to performing scRNA-Seq analysis of a plurality of samples, for each sample: (a) incubating one or more amine-modified sample tags with a first heterobifunctional linker to generate one or more tetrazine-modified sample tags; and (b) incubating the one or more tetrazine-modified sample tags of step (a) with (i) a second heterobifunctional linker, and (ii) a sample comprising one or more particles, to generate particles tagged with one or more sample tags. In some embodiments, the first heterobifunctional linker comprises a first reactive group and a second reactive group, wherein the first reactive group of the first heterobifunctional linker comprises an amine-reactive functional group and wherein the second reactive group of first heterobifunctional linker comprises a tetrazine moiety. In some embodiments, the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety.

Disclosed herein include sample multiplexing methods for single-cell RNA sequencing (scRNA-Seq). In some embodiments, the method comprises, prior to performing scRNA-Seq analysis of a plurality of samples, for each sample: (a) providing one or more tetrazine-modified sample tags; and (b) incubating one or more tetrazine-modified sample tags with (i) a second heterobifunctional linker, and (ii) a sample comprising one or more particles, to generate particles tagged with one or more sample tags. In some embodiments, the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety.

Disclosed herein are kits for tagging a plurality of samples. In some embodiments, the kit comprises: one or more amine-modified sample tags, a first heterobifunctional linker, and a second heterobifunctional linker; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a tetrazine moiety; and wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety.

Disclosed herein include methods of tagging a plurality of samples. In some embodiments, the method comprises, for each sample of a plurality of samples: (a) incubating one or more sample tags with a reagent to generate one or more functionalized sample tags via a click chemistry reaction; and (b) incubating the one or more functionalized sample tags of step (a) with a sample comprising one or more particles, to generate particles tagged with one or more sample tags.

Disclosed herein include sample multiplexing methods for scRNA-Seq. In some embodiments, the method comprises, prior to performing scRNA-Seq analysis of a plurality of samples, for each sample: (a) incubating one or more sample tags with a reagent to generate one or more functionalized sample tags via a click chemistry reaction; and (b) incubating the one or more functionalized sample tags of step (a) with a sample comprising one or more particles, to generate particles tagged with one or more sample tags.

Disclosed herein include methods of tagging a plurality of samples. In some embodiments, the method comprises, for each sample of a plurality of samples: (a) incubating anchor sample tags with a reagent to generate functionalized anchor sample tags via a click chemistry reaction; and (b) incubating the functionalized anchor sample tags of step (a) with a sample comprising one or more particles, to generate particles tagged with anchor sample tags; wherein said anchor sample tags comprise a component that can bind to one or more sample tags. Disclosed herein include sample multiplexing methods for scRNA-Seq. In some embodiments, the method comprises, prior to performing scRNA-Seq analysis of a plurality of samples, for each sample: (a) incubating anchor sample tags with a reagent to generate functionalized anchor sample tags via a click chemistry reaction; and (b) incubating the functionalized anchor sample tags of step (a) with a sample comprising one or more particles, to generate particles tagged with anchor sample tags; wherein said anchor sample tags comprise a component that can bind to one or more sample tags. In some embodiments, step (b) further comprises incubating the particles tagged with the anchor sample tags with one or more sample tags to generate particles tagged with one or more sample tags.

Disclosed herein include methods of tagging a plurality of samples. In some embodiments, the method comprises, for each sample of a plurality of samples: (a) incubating one or more amine-modified sample tags with a first heterobifunctional linker to generate one or more DBCO-modified sample tags; and (b) incubating the one or more DBCO-modified sample tags of step (a) with (i) a second heterobifunctional linker, and (ii) a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety; and wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a DBCO-reactive moiety.

Disclosed herein include sample multiplexing methods for scRNA-Seq. In some embodiments, the method comprises, prior to performing scRNA-Seq analysis of a plurality of samples, for each sample: (a) incubating one or more amine-modified sample tags with a first heterobifunctional linker to generate one or more DBCO-modified sample tags; and (b) incubating the one or more DBCO-modified sample tags of step (a) with (i) a second heterobifunctional linker, and (ii) a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety; and wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a DBCO-reactive moiety.

Disclosed herein include methods of tagging a plurality of samples. In some embodiments, the method comprises, for each sample of a plurality of samples: (a) incubating one or more amine-modified sample tags with a first heterobifunctional linker to generate one or more DBCO-modified sample tags; and (b) incubating the one or more DBCO-modified sample tags of step (a) with a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety.

Disclosed herein include sample multiplexing methods for scRNA-Seq. In some embodiments, the method comprises, prior to performing scRNA-Seq analysis of a plurality of samples, for each sample: (a) incubating one or more amine-modified sample tags with a first heterobifunctional linker to generate one or more DBCO-modified sample tags; and (b) incubating the one or more DBCO-modified sample tags of step (a) with a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety.

Disclosed herein are kits for tagging a plurality of samples. In some embodiments, the kit comprises: one or more tetrazine-modified sample tags, and a second heterobifunctional linker; wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety.

Methods for Multiplexing scRNA-Seq Samples

The fusion of microfluidics with chemical and molecular biology is reshaping biological research. Thousands to millions of cells can now be processed simultaneously on a single microfluidic chip, meaning experiments typically performed on whole tissues in bulk are now done in parallel on isolated cells. The choreographed interplay between individual cells of diverse types, which underlies the daunting complexity of multicellular behavior, is finally being unraveled one cell at a time. At the center of this revolution sits single-cell RNA-sequencing (scRNA-seq), which partitions rich, functional RNA-seq data into highly multiplexed libraries with unique DNA barcodes for each cell of origin. Our understanding of such complex systems as tumors, the blood, and the brain is in the midst of a transformation due to rapid advances in scRNA-Seq, as this enables profiling the transcriptomes of many cells in parallel. Today, a typical scRNA-seq experiment can sparsely profile $10^4$ cells, with some platforms now able to process $10^5$ cells and the release of the first million-cell dataset in 2017. As tens of thousands of cells can be analyzed at once, this paves the way for scRNA-seq analysis of complex experiments yielding many diverse populations of cells. Despite continued, explosive growth in the scale of scRNA-seq libraries, practical device operation limits most studies to only a few samples. Paradoxically, this disconnect arises from the fact that single-cell experiments are still performed 'in bulk', where all cells in a library, although barcoded individually, are treated as a single sample. Under this paradigm, scRNA-seq is used to deeply interrogate complex samples but cannot be readily applied to more complex studies involving many samples or experimental conditions. Thus, as scRNA-seq provides increasingly detailed characterization of numerous tissues, relatively little progress has been made in leveraging its scale and throughput to examine tissue dynamics as the result of experimental perturbations. Without the ability to analyze many samples simultaneously, scRNA-seq is ill-fitted as a clinical diagnostic or experimental readout.

To address the above-mentioned needs, there are provided, in some embodiments, methods and compositions for scRNA-seq parallel analysis of samples. In some embodiments, the methods comprise an additional layer of barcoding at the sample level, distributing the high cell capacity of scRNA-seq platforms across numerous samples. The scRNA-seq sample multiplexing methods provided herein allow for cells from individual samples to be rapidly chemically labeled with identifying sample tags (e.g., DNA oligonucleotides). In some embodiments, the multiplexing methods disclosed comprise the direct chemical labeling of samples of cells (e.g., live cells, fixed cells) with identifying sample tags (e.g., barcoded DNA sequences) such that each cell in a scRNA-seq experiment can be mapped back to its sample of origin. Additionally, the multiplexing methods disclosed herein can be compatible with any scRNA-seq protocol based on poly(A) capture. The provided methods of sample multiplexing can be applied in a variety of high-interest contexts, such as, but not limited to, large chemical screens, clinical analysis, ultra-low-input scRNA-seq and/or epitope density profiling. In some embodiments, sample labeling performed as disclosed herein also clarifies previously difficult problems regarding cell doublets and/or low-capture cells. In some embodiments, the chemical labeling methods disclosed herein are particularly advantageous because, unlike existing methods for multiplexing scRNA-seq samples, this procedure uses inexpensive, readily available reagents and can be applied to any cell of interest without the need for specific epitopes, sequence markers, or genetic manipulation. The chemical tagging reactions disclosed herein can, in some embodiments, be quenched and pooled before washing away excess oligonucleotides, thereby greatly increasing the speed and throughput of cell labeling as compared to antibody-based approaches. As multiplexing of DNA libraries has vastly improved the utility and adoption of high-throughput DNA sequencing, the sample multiplexing methods disclosed herein for scRNA-seq will similarly reduce costs, drive increases in cell capacity, and extend the scope of scRNA-seq beyond bulk tissue profiling. Furthermore, the increasing throughput of scRNA-seq will facilitate even higher multiplexing, and the sample multiplexing methods provided herein can be readily applied to thousands of samples. For diagnostic purposes, the cost savings associated with multiplex scRNA-seq also have the potential to accelerate the adoption of single-cell genomics in the clinic.

Methods of Sample Tagging

FIGS. 1A-1B show schematic illustrations of non-limiting exemplary embodiments of the sample tagging method of the disclosure. FIG. 1A illustrates the sample tagging concept. In multiplex scRNA-seq, samples of cells are individually tagged with identifying DNA oligonucleotides, sequenced as a pool, and computationally demultiplexed. FIG. 1B illustrates the chemoprecipitation of barcoded oligonucleotides onto target cells. Amine-modified oligonucleotides are activated with NHS-methyltetrazine (NHS-MTZ), then combined with target cells and the heterobifunctional cross-linker NHS-trans-cyclooctene (NHS-TCO) in a one-pot, two-step reaction to produce DNA-functionalized cells. In some embodiments, sample tagging is achieved in a one-pot, two-step reaction. In some embodiments, the methods comprise exposing cell samples to methyltetrazine-activated DNA oligonucleotides and the amine-reactive cross-linker NHS-trans-cyclooctene. NHS-functionalized oligonucleotides can be formed in situ via inverse-electron demand diels-alder (IEDDA) chemistry, and nucleophilic attack by accessible cellular amines can chemoprecipitate the oligonucleotides directly onto the cells. In some embodiments, the use of NHS-ester and inverse-electron demand Diels-Alder (IEDDA) chemistry enables the tagging reaction to be performed immediately prior to single-cell library preparation in a rapid (e.g., twenty-minute) reaction under physiological conditions. Library preparation can be derived from—and compatible with—current methods for multi-modal scRNA-seq (e.g., epitope profiling). In some embodiments, the samples tags comprise capture sequences (e.g., poly-A tails) that are captured by barcoded reverse transcription primers, separated from the cDNA library by size, and specifically amplified.

Disclosed herein include methods of tagging a plurality of samples. In some embodiments, the method comprises, for each sample of a plurality of samples: (a) incubating one or more sample tags with a reagent to generate one or more functionalized sample tags via a click chemistry reaction; and (b) incubating the one or more functionalized sample tags of step (a) with a sample comprising one or more particles, to generate particles tagged with one or more sample tags. Disclosed herein include sample multiplexing methods for scRNA-Seq. In some embodiments, the method comprises, prior to performing scRNA-Seq analysis of a plurality of samples, for each sample: (a) incubating one or more sample tags with a reagent to generate one or more functionalized sample tags via a click chemistry reaction; and (b) incubating the one or more functionalized sample tags of step (a) with a sample comprising one or more particles, to generate particles tagged with one or more sample tags. In some embodiments, the click chemistry reaction is strain-promoted azide/alkyne cycloaddition (SPAAC) reaction, inverse-electron demand diels-alder (IEDDA) reaction, copper catalyzed azide-alkyne cycloaddition (CuAAC) reaction, and any combination thereof.

Disclosed herein include methods for tagging a plurality of samples. In some embodiments, the method comprises: for each sample of a plurality of samples: (a) incubating one or more amine-modified sample tags with a first heterobifunctional linker to generate one or more tetrazine-modified sample tags; and (b) incubating the one or more tetrazine-modified sample tags of step (a) with (i) a second heterobifunctional linker, and (ii) a sample comprising one or more particles, to generate particles tagged with one or more sample tags. In other embodiments, the method can comprise: for each sample of a plurality of samples: (a) providing one or more tetrazine-modified sample tags; and (b) incubating one or more tetrazine-modified sample tags (i) a second heterobifunctional linker, and (ii) a sample comprising one or more particles, to generate particles tagged with one or more sample tags. Also disclosed herein include sample multiplexing methods for single-cell RNA sequencing (scRNA-Seq). In some embodiments, the method comprises, prior to performing scRNA-Seq analysis of a plurality of samples, for each sample: (a) incubating one or more amine-modified sample tags with a first heterobifunctional linker to generate one or more tetrazine-modified sample tags; and (b) incubating the one or more tetrazine-modified sample tags of step (a) with (i) a second heterobifunctional linker, and (ii) a sample comprising one or more particles, to generate particles tagged with one or more sample tags. Alternatively, the method can comprise, prior to performing scRNA-Seq analysis of a plurality of samples, for each sample: (a) providing one or more tetrazine-modified sample tags; and (b) incubating one or more tetrazine-modified sample tags with (i) a second heterobifunctional linker, and (ii) a sample comprising one or more particles, to generate particles tagged with one or more sample tags.

The first heterobifunctional linker can comprise a first reactive group and a second reactive group. The first reactive group of the first heterobifunctional linker can comprise an amine-reactive functional group and the second reactive group of first heterobifunctional linker can comprise a tetrazine moiety. The second heterobifunctional linker can comprise a first reactive group and a second reactive group. The first reactive group of the second heterobifunctional linker can comprise an amine-reactive functional group and the second reactive group of the second heterobifunctional linker can comprise a tetrazine-reactive moiety. In some embodiments, the amine-reactive functional group is selected from the group comprising an isothiocyanate, isocyanate, acyl azide, N-hydroxysuccinimide (NHS) ester, sulfonyl chloride, aldehyde, glyoxal, epoxide, carbonate, arylating agent, imidoester, carbodimide, and derivatives thereof. In some embodiments, the tetrazine-reactive moiety is selected from the group comprising trans-cyclooctene (TCO), dibenzocyclooctyne (DBCO), difluorinated cyclooctyne (DIFO), bicyclononyne (BCN), dibenzocyclooctyne (DICO) and derivatives thereof. In some embodiments, the tetrazine moiety is selected from the group comprising 1,2,3,4-tetrazine, 1,2,3,5-tetrazine, 1,2,4,5-tetrazine, and derivatives thereof. In some embodiments, the tetrazine moiety is methyltetrazine (MTZ). In some embodiments, the amine-reactive functional group is N-hydroxysuccinimide (NHS) ester. In some embodiments, the tetrazine-reactive moiety is trans-cyclooctene (TCO). In some embodiments, the first heterobifunctional linker is NHS-MTZ. In some embodiments, the second heterobifunctional linker is NHS-TCO.

In some embodiments, the click chemistry reaction is a strain-promoted azide/alkyne cycloaddition (SPAAC) reaction. In some embodiments, the methods provided herein comprise anchor sample tags. In some embodiments, said anchor sample tags comprise a component that can bind to one or more sample tags. In some embodiments, the component that can bind to one or more sample tags is invariant across all anchor sample tags. In some embodiments, the one or more sample tags comprise a component that binds the anchor sample tag. In some embodiments, the component of the one or more sample tags that binds the anchor sample tag is invariant across all sample tags. In some embodiments, the component that can bind to one or more sample tags and the component that can bind to one or more anchor sample tags are complementary oligonucleotide sequences that hybridize to each other. Disclosed herein include methods of tagging a plurality of samples. In some embodiments, the method comprises, for each sample of a plurality of samples:
(a) incubating anchor sample tags with a reagent to generate functionalized anchor sample tags via a click chemistry reaction; and (b) incubating the functionalized anchor sample tags of step (a) with a sample comprising one or more particles, to generate particles tagged with anchor sample tags; wherein said anchor sample tags comprise a component that can bind to one or more sample tags. Disclosed herein include sample multiplexing methods for scRNA-Seq. In some embodiments, the method comprises, prior to performing scRNA-Seq analysis of a plurality of samples, for each sample: (a) incubating anchor sample tags with a reagent to generate functionalized anchor sample tags via a click chemistry reaction; and (b) incubating the functionalized anchor sample tags of step (a) with a sample comprising one or more particles, to generate particles tagged with anchor sample tags; wherein said anchor sample tags comprise a component that can bind to one or more sample tags. In some embodiments, step (b) further comprises incubating the particles tagged with the anchor sample tags with one or more sample tags to generate particles tagged with one or more sample tags.

Disclosed herein include methods of tagging a plurality of samples. In some embodiments, the method comprises, for each sample of a plurality of samples: (a) incubating one or more amine-modified sample tags with a first heterobifunctional linker to generate one or more DBCO-modified sample tags; and (b) incubating the one or more DBCO-modified sample tags of step (a) with (i) a second heterobifunctional linker, and (ii) a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety; and wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a DBCO-reactive moiety. Disclosed herein include sample multiplexing methods for scRNA-Seq. In some embodiments, the method comprises, prior to performing scRNA-Seq analysis of a plurality of samples, for each sample: (a) incubating one or more amine-modified sample tags with a first heterobifunctional linker to generate one or more DBCO-modified sample tags; and (b) incubating the one or more DBCO-modified sample tags of step (a) with (i) a second heterobifunctional linker, and (ii) a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety; and wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a DBCO-reactive moiety.

Disclosed herein include methods of tagging a plurality of samples. In some embodiments, the method comprises, for each sample of a plurality of samples: (a) incubating one or more amine-modified sample tags with a first heterobifunctional linker to generate one or more DBCO-modified sample tags; and (b) incubating the one or more DBCO-modified sample tags of step (a) with a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety. Disclosed herein include sample multiplexing methods for scRNA-Seq. In some embodiments, the method comprises, prior to performing scRNA-Seq analysis of a plurality of samples, for each sample: (a) incubating one or more amine-modified sample tags with a first heterobifunctional linker to generate one or more DBCO-modified sample tags; and (b) incubating the one or more DBCO-modified sample tags of step (a) with a sample comprising one or more particles, to generate particles tagged with one or more sample tags; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a DBCO moiety. The sample tag activation step (e.g., step (a), preparation of tetrazine-functionalized sample tags, formation of tetrazine-modified oligonucleotides) can be performed for a period of about 10 minutes to about 240 minutes. The sample tag activation reaction time can be different in different implementations. In some embodiments, the sample tag activation step can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 minutes, or a number or a range between any two of these values. In some embodiments, the sample tag activation step can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000 minutes. In some embodiments, step (a) is performed for a period of about 10 minutes to about 240 minutes. In some embodiments, step (a) is performed for a period of about 180 minutes. In some embodiments, step (a) is performed for a period of about 90 minutes. Step (a) can comprise the addition of one or more (e.g., 1, 2, 3, 4, 5, 6, 7, or more) further aliquots of the first heterobifunctional linker during the incubation. In some embodiments, step (a) is performed at a temperature between about 15° C. to 50° C., (e.g., 15° C., 20° C., 25° C., 30° C., 35° C., 40° C., 45° C., 50° C., and ranges in between any two of these values). In some embodiments step (a) is performed at a temperature of about 37° C. to about 45° C. In some embodiments, step (a) is performed at a temperature of about 20° C. The sample tag activation step can be performed in the presence of a polar solvent (e.g., dimethyl sulfoxide (DMSO)). Step (a) can comprise ethanol precipitation of the one or more tetrazine-modified sample tags at the end of the incubation. Sample tag activation can be performed immediately prior to sample tag chemoprecipitation by inverse-electron demand Diels-Alder (IEDDA) chemistry. Alternatively, activated sample tags (e.g., tetrazine-modified sample tags) are frozen prior to the sample tag chemoprecipitation reaction.

The sample tag chemoprecipitation step (e.g., step (b), conjugation of sample tags onto particles, tagging of particles) can be a one-pot, two-step reaction. In some embodiments, step (b) comprises the in situ generation of amine-reactive sample tags (e.g., barcoded oligonucleotides comprising an amine-reactive functional group) via inverse-electron demand diels-alder (IEDDA) chemistry. In some embodiments, nucleophilic attack of exposed primary amines on the one or more particles by the amine-reactive sample tags generates particles tagged with one or more sample tags. The sample tag chemoprecipitation step can be performed for a period of about 10 minutes to about 180 minutes. The sample tag chemoprecipitation reaction time can be different in different implementations. In some embodiments, the sample tag chemoprecipitation step can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 minutes, or a number or a range between any two of these values. In some embodiments, the sample tag chemoprecipitation step can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000 minutes. In some embodiments, step (b) is performed for a period of about 30 minutes. In some embodiments, step (b) is performed for a period of about 20 minutes. In some embodiments, step (b) is performed at a temperature between about 4° C. to 50° C., (e.g., 4° C., 10° C., 15° C., 20° C., 25° C., 30° C., 35° C., 40° C., 45° C., 50° C., and ranges in between any two of these values). In some embodiments, step (b) is performed at a temperature of about 20° C. In some embodiments, step (b) is performed at a temperature of about 4° C. Depending on the embodiment, step (b) can be performed in the dark or in the light. Step (b) can be performed under physiological aqueous conditions and/or under methanol fixation conditions. In some embodiments, step (b) is performed in a buffer devoid of buffer components containing primary amines. The sample tag chemoprecipitation step can performed in a buffer compatible with NHS-ester conjugation. Step (b) can comprise, in some embodiments: i) preincubation of the one or more tetrazine-modified sample tags and the second heterobifunctional linker; and ii) addition of the a sample comprising one or more particles to the one or more tetrazine-modified sample tags and the second heterobifunctional linker from (i) to generate particles tagged with one or more sample tags. The preincubation can performed for a period of about 5 minutes to about 120 minutes. Step (b) can further comprise the sub step of quenching the reaction (e.g., by addition of methyltetrazine-DBCO). In some embodiments, the quenching comprises the addition of a primary amine. In some embodiments, the primary amine comprises Tris-HCl. In some embodiments, the quenching comprises the addition of a methyltetrazine-derivatized molecule. In some embodiments, the methyltetrazine-derivatized molecule comprises MTZ-DBCO, a MTZ-amine, a MTZ-carboxylic acid, and any combination thereof. In some embodiments, the quenching comprises the addition of a DBCO-derivatized molecule. In some embodiments, the DBCO-derivatized molecule comprises MTZ-DBCO, DBCO-amine, DBCO-carboxylic acid, and any combination thereof. The quenching can performed for a period of about 5 minutes to about 120 minutes. The particles tagged with one or more sample tags of the plurality of samples can be pooled following the completion of sample tag chemoprecipitation.

Sample Tags

There are provided, in some embodiments, identifying sample tags. In some embodiments, amine-modified sample tags are provided. In some embodiments, the sample tag comprises a nucleic acid. The nucleic acid can comprise deoxyribonucleic acid (DNA), a ribonucleic acid (RNA), a modified RNA (such as those with 2'-fluoro and/or 2'-O-methyl riboses), a locked nucleic acid (LNA), a peptide nucleic acid (PNA) and/or a morpholino. A sample tag can comprise modified nucleotides, such as methylated nucleotides and nucleotide analogs ("analogous" forms of purines and pyrimidines are well known in the art). If present, modifications to the nucleotide structure may be imparted before or after assembly of the polymer. A sample tag can be a single-stranded, double-stranded, partially single-stranded, or partially double-stranded DNA or RNA. In some embodiments, the one or more amine-modified sample tags comprises an oligonucleotide, wherein the oligonucleotide comprises a 3' amine, a 5' amine, or combination thereof. In some embodiments, the sample tag comprises a DNA oligonucleotide. In some embodiments, the sample tag comprises an RNA oligonucleotide. The sample tag can have different lengths in different implementations. In some embodiments, sample tag is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, sample tag is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

The sample tag can comprise a capture sequence (e.g., a sequence bound and/or reversed transcribed by scRNA-seq protocol reagents). In some embodiments, the capture sequence binds the capture-binding sequence of a component of a library preparation kit, wherein a library preparation kit comprises a cDNA library preparation kit, a genomic library preparation kit, a sequencing library preparation kit, and any combination thereof. In some embodiments, the capture sequence is a poly(dA) region at the 5' end and/or 3'end of the oligonucleotide. In some embodiments, the poly(dA) region is about 10 nucleotides to about 100 nucleotides in length. In some embodiments, the sample tag comprises a constant region. In some embodiments, the constant region comprises a sequence bound by a library preparation reagent, by a sequencing platform reagent, and any combination thereof. In some embodiments, the constant region comprises a PCR primer region. In some embodiments, the PCR primer region comprises all or a portion of a binding site for a sequencing primer (e.g., an Illumina sequencing primer). The PCR primer region can comprise a primer binding site shared with most or all other target molecules during cDNA library preparation and/or sequencing library preparation and/or sequencing library amplification (e.g., a "universal priming site" or "universal primer binding site"). In some embodiments, the PCR primer region comprises all or a portion of a Read 1 sequencing primer annealing site. The sample tag can comprise a barcode sequence. The barcode sequence can have different lengths in different implementations. In some embodiments, barcode sequence is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, barcode sequence is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length. In some embodiments, the barcode sequence is about 10 nucleotides in length.

Sample Tag Sets

The one or more sample tags can comprise a sample tag set. In some embodiments, the sample tag set comprises a single sample tag. A sample tag set can comprise a plurality of sample tags with distinct barcode sequences. In some embodiments, the sample tag set comprises 2 sample tags with distinct barcode sequences. In some embodiments, the sample tag set comprises 3 sample tags with distinct barcode sequences. In some embodiments, the sample tag set comprises 4 sample tags with distinct barcode sequences. In some embodiments, the sample tag set comprises 5 sample tags with distinct barcode sequences. In some embodiments, the sample tag set comprises 6 sample tags with distinct barcode sequences. In some embodiments, the sample tag set comprises 7 sample tags with distinct barcode sequences. In some embodiments, the sample tag set comprises 8 or more sample tags with distinct barcode sequences. In some embodiments, distinct barcode sequences differ with regard to the identity of at least one, two, three, four, five, six, seven, or more nucleotides. In some embodiments, the sequence identity between distinct barcode sequences can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a number or a range between any two of these values. In some embodiments, the sequence identity between distinct barcode sequences can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. One or more particles of each sample of the plurality of samples can labeled with a unique sample tag set according to the methods of the disclosure. In some embodiments, each of a plurality of samples is labeled with a wholly unique sample tag set. In some embodiments, each of a plurality of samples is labeled with a partially unique sample tag set. In some embodiments, the combined barcode sequence(s) of all sample tag(s) within a unique sample tag set are distinct from the combined barcode sequence(s) of all sample tag(s) of every other sample tag set in a plurality of sample tag sets. In some embodiments, the one or more sample tags is selected from a sample tag pool. The size of the sample tag pool can be different in different implementations. In some embodiments, the size of the sample tag pool can be, or be about, 2, 3, 4, 5, 6, 7, 8, 9, 10, 20, 30, 40, 50, 60, 70, 80, 90, 100, 200, 300, 400, 500, 600, 700, 800, 900, 1000, 10000, 20000, 30000, 40000, 50000, 60000, 70000, 80000, 90000, 100000, $10^6$, $10^7$, $10^8$ or a number or a range between any two of these values, sample tags with distinct barcode sequences. In some embodiments, the size of the sample tag pool can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000, 10000, 20000, 30000, 40000, 50000, 60000, 70000, 80000, 90000, 100000, $10^6$, $10^7$, or $10^8$, sample tags with distinct barcode sequences. In some embodiments, the sample tag pool comprises all of the sample tags with distinct barcode sequences. The number of unique sample tag sets within a plurality of sample tag sets can be represented by the binomial coefficient $$\binom{n}{k},$$

wherein n is the number of sample tags in the sample tag pool and k is the number of sample tags in a unique sample tag set. The number of unique sample tag sets can be different in different implementations. In some embodiments, the number of unique sample tag sets can be, or be about, 2, 3, 4, 5, 6, 7, 8, 9, 10, 20, 30, 40, 50, 60, 70, 80, 90, 100, 200, 300, 400, 500, 600, 700, 800, 900, 1000, 10000, 20000, 30000, 40000, 50000, 60000, 70000, 80000, 90000, 100000, $10^6$, $10^7$, $10^8$ or a number or a range between any two of these values. In some embodiments, the number of unique sample tag sets can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000, 10000, 20000, 30000, 40000, 50000, 60000, 70000, 80000, 90000, 100000, $10^6$, $10^7$, or $10^8$.

Samples

The number of samples tagged according to methods provided herein can be different in different implementations. The plurality of samples can comprise 2 or more samples. In some embodiments, the number of tagged samples can be, or be about, 2, 3, 4, 5, 6, 7, 8, 9, 10, 20, 30, 40, 50, 60, 70, 80, 90, 100, 200, 300, 400, 500, 600, 700, 800, 900, 1000, 10000, 20000, 30000, 40000, 50000, 60000, 70000, 80000, 90000, 100000, $10^6$, $10^7$, $10^8$ or a number or a range between any two of these values. In some embodiments, the number of tagged samples can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000, 10000, 20000, 30000, 40000, 50000, 60000, 70000, 80000, 90000, 100000, $10^6$, $10^7$, or $10^8$. In some embodiments, the one or more biological particles tagged according the methods provided herein comprise one or more of prokaryotic cells, eukaryotic cells, viral particles, exosomes, protoplasts, microvesicles, and any combination thereof. In some embodiments, the one or more cells are prokaryotic cells. In some embodiments, the one or more cells are eukaryotic cells. In some embodiments, the one or more cells are selected from the group comprising fungal cells, plant cells, insect cells, and any combination thereof. In some embodiments, the one or more cells are mammalian cells. In some embodiments, a sample comprises all or a portion of one or more mammalian tissues. In some embodiments, the sample comprises about 1 cell to about 100,000 cells. In some embodiments, the sample comprises about 1 cell to about 100,000 cells. In some embodiments, the number of cells within a sample can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 20000, 30000, 40000, 50000, 60000, 70000, 80000, 90000, 100000, $10^6$, $10^7$, $10^8$ or a number or a range between any two of these values. In some embodiments, the number of cells within a sample can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000, 10000, 20000, 30000, 40000, 50000, 60000, 70000, 80000, 90000, 100000, $10^6$, $10^7$, or $10^8$. In some embodiments, one or more of the samples is a patient sample. In some embodiments, the one or more particles comprise one or more synthetic particles. In some embodiments, the one or more synthetic particles comprise beads, synthetic cells, lipid droplets, and any combination thereof. In some embodiments, the beads comprise magnetic beads, glass beads, cellulose beads, epichlorohydrin-cross-linked-dextran beads, polyacrylamide beads, agarose beads, polystyrene beads, gel-based beads, and any combination thereof. In some embodiments, the beads are chemically functionalized. In some embodiments, the one or more particles comprise one or more biological particles. The cells can be live cells, fixed cells (e.g., methanol-fixed cells, or any combination thereof. The "plex" of a given multiplex scRNA-seq experiment (e.g., the number of different samples that are processed in parallel) can vary depending on the embodiment of the methods of the disclosure. In some embodiments, the plex can be about 12-plex, 24-plex, 48-plex, 96-plex, 192-plex, 384-plex, 768-plex, 1536-plex, 3072-plex, 6144-plex, 12288-plex, 24576-plex, 49152-plex, 98304-plex, or higher, or a number or a range between any two of these values.

In some embodiments, the one or more samples of the plurality of samples are exposed to one or more perturbations prior to tagging according the methods provided herein. The one or more perturbations can comprise an environmental condition (e.g., a physical condition, chemical condition, a temporal condition, a biological condition, or any combination thereof), a small molecule, an agent, or any combination thereof. In some embodiments, two or more samples of the plurality of samples are exposed to different concentrations of the same agent or the same small molecule prior to tagging. The agent can comprise one or more of cytokines, hormones, growth factors, toxins, inflammatory molecules, oncogene products, signal transduction molecules, or any combination thereof. In other embodiments, the agent is an agent capable of modulating expression of a gene (e.g., a CRISPR system, RNAi, TALE, or zinc finger protein, or any combination thereof). In some embodiments, the agent capable of modulating expression of a gene is inducible. In some embodiments, the one or more samples of the plurality of samples are subjected to drug and/or screening prior to tagging according the methods provided herein.

Sequence Analysis

In some embodiments, the one or more particles tagged with one or more sample tags comprise nucleic acids. The nucleic acids can comprise genomic DNA, mitochondria DNA, mitochondrial RNA, mRNAs, non-coding RNAs, micro RNAs (miRNAs), Piwi-interacting RNAs (piRNAs), snoRNAs, snRNAs, moRNAs, PARs, sdRNAs, tel-sRNAs, crasiRNAs, long non-coding RNAs (long ncRNAs), tRNAs, ribosomal RNA (rRNA), and any combination thereof. The multiplexing methods disclosed herein are compatible with any single cell sequencing platform, including, but not limited to, the 10× Chromium system, Drop-Seq, inDrops, sciRNA-seq, ddSEQ (Bio-Rad), full-length scRNA-seq and other single-cell genomic assays. In some embodiments, multiplexing methods disclosed herein are compatible with any scRNA-seq protocol based on poly(A) capture. In some embodiments, the method further comprises performing the step of sequence analysis for each sample of the plurality of samples. Sequence analysis can comprise i) sequence analysis of the one or more sample tags and/or (ii) sequence analysis of nucleic acids of the one or more particles tagged with said one or more sample tags. In some embodiments, the sequence analysis comprises single cell sequence analysis. In some embodiments, the capture sequences of sample tags (e.g., poly-A tails) are captured by barcoded reverse transcription primers, separated from the cDNA library by size, and/or specifically amplified.

In some embodiments, the sequence analysis comprises epitope density profiling. In some embodiments, the sequence analysis comprises RNA sequence analysis. In some embodiments, the RNA sequence analysis comprises whole transcriptome sequencing. RNA sequence analysis can comprise single-cell RNA sequencing (scRNA-Seq), targeted RNA sequencing, ultra-low-input scRNA-seq, or any combination thereof. In some embodiments, targeted RNA sequencing comprises targeted mRNA sequencing. In some embodiments, targeted RNA sequencing comprises targeted non-coding RNA sequencing. In some embodiments, the sequence analysis comprises DNA sequence analysis. DNA sequence analysis can comprise whole genome sequencing, whole exome sequencing, targeted gene sequencing, whole regulome sequencing, sequencing-based methylation analysis, sequencing-based breakpoint detection, ChIP sequencing, or any combination thereof. In some embodiments, the sequencing may include using high-throughput sequencing platforms such as, for example, Roche 454 (e.g., Roche 454 GS FLX); Applied Biosystems' SOLiD® system (e.g., SOLiD®v4); Ulumina's GAIIx, HiSeq® 2000 and MiSeq® sequencers; Life Technologies' Ion Torrent® semiconductor sequencing platform, Pacific Biosciences' PacBio RS and Sanger's 3730xl.

In some embodiments, sequence analysis comprises sample demultiplexing. Sample demultiplexing can comprise associating the results of sequence analysis of the one or more particles with the sample of origin based on a sequence analysis of the one or more sample tags. In some embodiments, the sequence analysis of the one or more sample tags comprises the determining the sequences of the one or more sample tags. Determining the sequences of the one or more sample tags can comprise determining the barcode sequences of the one or more sample tags, thereby identifying the sample tag set. Sequence analysis can comprise single cell sequence analysis, wherein sequence analysis of the one or more sample tags comprises determining a sum of sample tag counts for a tagged cell, wherein the sum of sample tag counts correlates with the size of a cell tagged with the sample tags. In some embodiments, the presence of barcode sequences of two or more sample tag sets for a single sample and/or a single cell indicates a doublet event. In some embodiments, the sum of sample tag counts for a tagged cell correlates with the size of the tagged cell. In some embodiments, the cost of sequence analysis is reduced by at least 5% as compared to a sequence analysis performed in the absence of said or more sample tags. In some embodiments, the sequence analysis yields reduced batch effects as compared to a sequence analysis performed in the absence of said or more sample tags. In some embodiments, the method does not comprise epitope labeling and/or genetic manipulation of the one or more samples prior to sample tagging.

Kits

Disclosed herein are kits for tagging a plurality of samples. In some embodiments, the kit comprises: one or more amine-modified sample tags, a first heterobifunctional linker, and a second heterobifunctional linker; wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a tetrazine moiety; and wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety. Disclosed herein are kits for tagging a plurality of samples. In some embodiments, the kit comprises: one or more tetrazine-modified sample tags, and a second heterobifunctional linker; wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety. In several embodiments, a kit comprising the components as described herein is provided along with instructions for use.

Disclosed herein are strain-promoted alkyne-azide cycloaddition (SPAAC) kits for tagging a plurality of samples, comprising: one or more amine-modified sample tags; NHS-Azide; and NHS-DBCO. Disclosed herein are kits for tagging a plurality of samples, comprising: one or more amine-modified sample tags; and NHS-DBCO. Also disclosed herein are kits for tagging a plurality of samples, comprising: one or more DBCO-modified sample tags.

EXAMPLES

Some aspects of the embodiments discussed above are disclosed in further detail in the following examples, which are not in any way intended to limit the scope of the present disclosure.

Experimental Materials and Methods

The following experimental materials and methods were used for Examples 1-4 described below.

Overview of Cell Tagging Procedure

Barcoded DNA oligonucleotides ("tags") are attached to exposed NHS-reactive amines on the cells of interest. Sample tagging is achieved in a one-pot, two-step reaction by exposing cell samples to methyltetrazine-activated DNA (MTZ-DNA) oligonucleotides and the amine-reactive cross-linker NHS-transcyclooctene (NHS-TCO) (depicted in FIG. 3B). NHS-functionalized oligonucleotides are formed in situ via inverse-electron demand Diels-Alder (IEDDA) chemistry, and nucleophilic attack by accessible cellular amines chemoprecipitates the oligonucleotides directly onto the cells. The one-pot reaction based on the IEDDA reaction improves on a previous cell surface modification scheme that requires far higher DNA concentrations and isolation of unstable activated DNAs immediately before use. A library of methyltetrazine-modified sample tags can be prepared in advance, stored frozen for long periods, and applied to many cell samples in parallel. Sequencing library preparation was derived from recently published methods for multi-modal scRNA-seq.

Oligo Activation

Sample tags were prepared with either 5'- or 3'-amine modified oligonucleotides (250 nmol scale for 5'-amine modified oligonucleotides, 100 nmol scale for 3'-amine modified oligonucleotides Integrated DNA Technologies). The sequences of the 5'- and 3'-amine modified oligonucleotides are depicted in Table 1. In some embodiments, HPLC purification can be employed to obtain highly reactive preparations of 5'-modified oligonucleotides. In some embodiments, 3'-modified oligonucleotides can be purchased without HPLC purification (e.g., standard desalting). In either case, oligonucleotides were resuspended to a concentration of 500 μM in 50 mM sodium borate buffer pH 8.5 (Thermo). Activation reactions were performed by combining 25 μL oligo solution with 41.8 μL DMSO (Sigma) and 8.2 μL of 10 mM NHS-methyltetrazine (Click Chemistry Tools). The reaction was allowed to proceed for 30 minutes at room temperature on a rotating platform. After 30 and 60 minutes, additional 8.2 μL aliquots of 10 mM NHS-methyltetrazine were added. After 90 minutes total reaction time, ethanol precipitation was performed by addition of 180 μL 50 mM sodium borate buffer and 30 μL 3 M NaCl. After mixing, 750 μL ice-cold ethanol was added and the mixture precipitated at −80° C. overnight. The precipitate was pelleted at 20,000×g for 30 minutes, washed twice with 1 mL ice-cold 70% ethanol, then resuspended in 100 μL 10 mM HEPES pH 7.2. Yield was determined by absorbance at 260 nm. Typical final concentrations ranged between 40 and 80 μM. Relative oligo activity was determined by electrophoretic mobility shift assay using Cy5-trans-cyclooctene (Click Chemistry Tools). Methyltetrazine-derivatized oligonucleotides were diluted 100-fold in 10 mM HEPES pH 7.2, then 4 μL of this solution was added to 1 μL of a 500 nM solution of TCO-Cy5 in DMSO. All tetrazine reactions in this work were protected from light to reduce degradation of trans-cyclooctene. The reaction was allowed to proceed at room temperature for 20-120 minutes and analyzed on a 12% SDS-PAGE gel. Oligo activity varied within a 2-fold range across preparations. Oligonucleotides were stored at −20° C. and used without further normalization.

TABLE 1

SAMPLE TAGS

| Name | SEQ ID NO: | Sequence |
|---|---|---|
| BC21 | 1 | /5AmMC6/TCGTCGGCAGCGTCAGATGTGTAAGCAGTTACAGBAAAAAAAAAAAAAAAAAAAAAAAAA |
| BC22 | 2 | /5AmMC6/TCGTCGGCAGCGTCAGATGTGTACTTGTACCCAGBAAAAAAAAAAAAAAAAAAAAAAAAA |
| BC23 | 3 | /5AmMC6/TCGTCGGCAGCGTCAGATGTGTAGAACCCGGCAGBAAAAAAAAAAAAAAAAAAAAAAAAA |
| BC24 | 4 | /5AmMC6/TCGTCGGCAGCGTCAGATGTGTATCGTAGATCAGBAAAAAAAAAAAAAAAAAAAAAAAAA |
| BC25 | 5 | /5AmMC6/TCGTCGGCAGCGTCAGATGTGTAACGCGGAACAGBAAAAAAAAAAAAAAAAAAAAAAAAA |
| BC26 | 6 | /5AmMC6/TCGTCGGCAGCGTCAGATGTGTACGCTATCCCAGBAAAAAAAAAAAAAAAAAAAAAAAAA |
| BC27 | 7 | /5AmMC6/TCGTCGGCAGCGTCAGATGTGTAGTTGCATGCAGBAAAAAAAAAAAAAAAAAAAAAAAAA |
| BC28 | 8 | /5AmMC6/TCGTCGGCAGCGTCAGATGTGTATAAATCGTCAGBAAAAAAAAAAAAAAAAAAAAAAAAA |
| BC29 | 9 | /5AmMC6/TCGTCGGCAGCGTCAGATGTGTAATCGCCATCAGBAAAAAAAAAAAAAAAAAAAAAAAAA |
| BC30 | 10 | /5AmMC6/TCGTCGGCAGCGTCAGATGTGTACATAAAGGCAGBAAAAAAAAAAAAAAAAAAAAAAAAA |
| BC31 | 11 | /5AmMC6/TCGTCGGCAGCGTCAGATGTGTATCACGGTACAGBAAAAAAAAAAAAAAAAAAAAAAAAA |
| BC32 | 12 | /5AmMC6/TCGTCGGCAGCGTCAGATGTGTACACTCAACCAGBAAAAAAAAAAAAAAAAAAAAAAAAA |
| BC33 | 13 | /5AmMC6/TCGTCGGCAGCGTCAGATGTGTAGCTGTGTACAGBAAAAAAAAAAAAAAAAAAAAAAAAA |

TABLE 1-continued

SAMPLE TAGS

| Name | SEQ ID NO: | Sequence |
|---|---|---|
| BC34 | 14 | /5AmMC6/TCGTCGGCAGCGTCAGATGTGTATTGCGTCGCAG<br>BAAAAAAAAAAAAAAAAAAAAAAAA |
| BC35 | 15 | /5AmMC6/TCGTCGGCAGCGTCAGATGTGTAATATGAGACAG<br>BAAAAAAAAAAAAAAAAAAAAAAAA |
| BC36 | 16 | /5AmMC6/TCGTCGGCAGCGTCAGATGTGTACACCTCAGCAG<br>BAAAAAAAAAAAAAAAAAAAAAAAA |
| BC37 | 17 | /5AmMC6/TCGTCGGCAGCGTCAGATGTGTAGCTACTTCCAG<br>BAAAAAAAAAAAAAAAAAAAAAAAA |
| BC38 | 18 | /5AmMC6/TCGTCGGCAGCGTCAGATGTGTATGGGAGCTCAG<br>BAAAAAAAAAAAAAAAAAAAAAAAA |
| BC39 | 19 | /5AmMC6/TCGTCGGCAGCGTCAGATGTGTAATCCGGCACAG<br>BAAAAAAAAAAAAAAAAAAAAAAAA |
| BC40 | 20 | /5AmMC6/TCGTCGGCAGCGTCAGATGTGTACCGTTATGCAG<br>BAAAAAAAAAAAAAAAAAAAAAAAA |
| REAP_BC41_v4 | 21 | TCGTCGGCAGCGTCAGATGTGTAGGTAATGTCAGBAAAAA<br>AAAAAAAAAAAAAAAAAAAA/3AmMO/ |
| REAP_BC42_v4 | 22 | TCGTCGGCAGCGTCAGATGTGTATAAGCCACCAGBAAAAA<br>AAAAAAAAAAAAAAAAAAAA/3AmMO/ |
| REAP_BC43_v4 | 23 | TCGTCGGCAGCGTCAGATGTGTAACCGAACACAGBAAAAA<br>AAAAAAAAAAAAAAAAAAAA/3AmMO/ |
| REAP_BC44_v4 | 24 | TCGTCGGCAGCGTCAGATGTGTACGACTCTTCAGBAAAAA<br>AAAAAAAAAAAAAAAAAAAA/3AmMO/ |
| REAP_BC45_v4 | 25 | TCGTCGGCAGCGTCAGATGTGTAGTTTGTGGCAGBAAAAA<br>AAAAAAAAAAAAAAAAAAAA/3AmMO/ |
| REAP_BC46_v4 | 26 | TCGTCGGCAGCGTCAGATGTGTATAGACGACCAGBAAAAA<br>AAAAAAAAAAAAAAAAAAAA/3AmMO/ |
| REAP_BC47_v4 | 27 | TCGTCGGCAGCGTCAGATGTGTAACGCTTGGCAGBAAAAA<br>AAAAAAAAAAAAAAAAAAAA/3AmMO/ |
| REAP_BC48_v4 | 28 | TCGTCGGCAGCGTCAGATGTGTACGCTACATCAGBAAAAA<br>AAAAAAAAAAAAAAAAAAAA/3AmMO/ |
| REAP_BC49_v4 | 29 | TCGTCGGCAGCGTCAGATGTGTAGAAAGACACAGBAAAAA<br>AAAAAAAAAAAAAAAAAAAA/3AmMO/ |
| REAP_BC50_v4 | 30 | TCGTCGGCAGCGTCAGATGTGTATTTGCGTCCAGBAAAAA<br>AAAAAAAAAAAAAAAAAAAA/3AmMO/ |
| REAP_BC51_v4 | 31 | TCGTCGGCAGCGTCAGATGTGTAATGGTCGCCAGBAAAAA<br>AAAAAAAAAAAAAAAAAAAA/3AmMO/ |
| REAP_BC52_v4 | 32 | TCGTCGGCAGCGTCAGATGTGTACGACATAGCAGBAAAAA<br>AAAAAAAAAAAAAAAAAAAA/3AmMO/ |
| REAP_BC53_v4 | 33 | TCGTCGGCAGCGTCAGATGTGTAGATTCGCTCAGBAAAAA<br>AAAAAAAAAAAAAAAAAAAA/3AmMO/ |
| REAP_BC54_v4 | 34 | TCGTCGGCAGCGTCAGATGTGTATCCAGATACAGBAAAAA<br>AAAAAAAAAAAAAAAAAAAA/3AmMO/ |
| REAP_BC55_v4 | 35 | TCGTCGGCAGCGTCAGATGTGTAACTACTGTCAGBAAAAA<br>AAAAAAAAAAAAAAAAAAAA/3AmMO/ |
| REAP_BC56_v4 | 36 | TCGTCGGCAGCGTCAGATGTGTACGGGAACGCAGBAAAAA<br>AAAAAAAAAAAAAAAAAAAA/3AmMO/ |
| REAP_BC57_v4 | 37 | TCGTCGGCAGCGTCAGATGTGTAGACCTCTCCAGBAAAAA<br>AAAAAAAAAAAAAAAAAAAA/3AmMO/ |
| REAP_BC58_v4 | 38 | TCGTCGGCAGCGTCAGATGTGTATTATGGAACAGBAAAAA<br>AAAAAAAAAAAAAAAAAAAA/3AmMO/ |

TABLE 1-continued

SAMPLE TAGS

| Name | SEQ ID NO: | Sequence |
|---|---|---|
| REAP_BC59_v4 | 39 | TCGTCGGCAGCGTCAGATGTGTAACAGCAACCAGBAAAAAAAAAAAAAAAAAAAAAAAAA/3AmMO/ |
| REAP_BC60_v4 | 40 | TCGTCGGCAGCGTCAGATGTGTACGCAATTTCAGBAAAAAAAAAAAAAAAAAAAAAAAAAA/3AmMO/ |

Cell Culture and Fixation

Neural stem cells were cultured according to the following protocol.

Cryopreserved mouse neural stem cells (NSCs) were thawed for 2 minutes at 37° C. then transferred to a 15 mL conical tube. Pre-warmed Neural Stem Cell Basal Medium (SCM003, Millipore) was slowly added to a total volume of 10 mL, and the resulting cell suspension centrifuged at room temperature for 2.5 minutes at 200×g. The supernatant was removed and the cell pellet was resuspended in 2 mL pre-warmed Neural Stem Cell Basal Medium and counted on the Countess II Automated Cell Counter (Thermo). Cells were seeded on poly-L-ornithine (Millipore) and laminin (Thermo) coated 100 mm culture plates at 700,000 cells per plate in 10 mL of pre-warmed Neural Stem Cell Basal Medium supplemented with EGF (Millipore) and bFGF (Millipore) at 20 ng/mL each, heparin (Sigma) at 2 µg/mL, and 1% Penicillin-Streptomycin (Thermo). Supplemented medium was changed the next day and every other day thereafter until confluent.

Neural stem cells for 96-sample growth factor screen were cultured according to the following protocol after previously described cell culture plate reached ~80% confluence: Stock solutions (10×) were prepared in Neural Stem Cell Basal Medium for every factor and at every concentration used: EGF+bFGF at 200 ng/mL, 40 ng/mL, 8 ng/mL, 1.6 ng/mL; BMP4 (Peprotech) at 200 ng/mL, 40 ng/mL, 8 ng/mL, 0 ng/mL; Retinoic Acid (Sigma) at 10 µM, 2 µM, 0 µM; Scriptaid (Selleckchem)/Decitabine (Selleckchem) at 1 µM/5 µM, 0.2 µM/1 µM, 0 µM/0 µM; Heparin at 20 µg/mL+Penicillin-Streptomycin at 10%. 20 µL each of EGF/bFGF, BMP4, Retinoic acid or Scriptaid/Decitabine, and Heparin/Penicillin-Streptomycin were added to each well of a poly-L-ornithine and laminin coated 96-well plate for a total of 80 µL.

NSCs previously plated on 100 mm culture plates until ~80% confluent were dissociated by incubation in 4 mL of ESGRO Complete Accutase (Millipore) for 2 minutes at 37° C. After incubation, the Accutase and NSCs were transferred to a 15 mL conical tube and centrifuged at room temperature for 2.5 minutes at 200×g. Supernatant was removed and the cell pellet was resuspended in 2 mL Neural Stem Cell Basal Medium. Centrifugation and medium replacement were repeated one more time and cell concentration was counted on the Countess II Automated Cell Counter. The cell suspension was then diluted with additional Neural Stem Cell Basal Medium to a concentration of 18.3 cells/µL. From this stock 120 µL was added to each well of the 96-well plate for a total of ~2,200 cells/well. Supplemented media for every well in the 96-well plate was replaced every other day during the 5-day incubation.

Before NSC dissociation and fixation, 80 µL of ice-cold methanol was added to each well of twelve 8-well PCR strips on an ice block. After 5 days in culture, all media in the 96-well plate were removed and the cells washed three times with 150 µL of Neural Stem Cell Basal Medium. Any remaining media were removed and replaced with 20 µL of Accutase and incubated at 37° C. for 2 minutes with gentle pipetting to help break cell clumps. Next, 20 µL of dissociated NSCs in Accutase were transferred to the 8-well strip tubes containing 80 µL of 100% methanol, and the entire volume was pipetted to mix. After fixation, the NSCs were stored at −20° C. until sample labeling.

For 4-sample NSC labeling and species-mixing experiments (below), NSCs were cultured on a 100 mm poly-L-ornithine and laminin coated culture plate according to the protocol previously described until ~80% confluent. NSCs were dissociated by removing culture medium followed by incubation with 4 mL Accutase for 2 minutes. NSCs in Accutase were transferred to a 15 mL conical tube and centrifuged at room temperature for 2.5 minutes at 200×g. The supernatant was removed and the cell pellet was resuspended in 2 mL Hank's Balanced Salt Solution (HBSS, Thermo) with 0.04% BSA (Sigma). Centrifugation and medium replacement were repeated once and cell concentration was determined on a Countess II Automated Cell Counter. Cells were then fixed by addition of 4 volumes ice-cold methanol added slowly with constant mixing. Fixed cells were stored at −20° C. until sample labeling and scRNA-seq.

Frozen stocks of HEK293T cells (ATCC) were thawed for 2 minutes at 37° C. with gentle agitation. Thawed cells (500 µL) were added to 5 mL pre-warmed media (DMEM (Corning)+10% FBS (Gemini Bio-Products)+1% Penicillin-Streptomycin (Corning) and centrifuged at 1,500×g for 5 minutes. The cells were resuspended in 5 mL media and transferred to a T-25 cell culture flask. Cells were grown at 37° C. with 5% CO2 following standard practices. HEK293T cells were dissociated by incubation with TrypLE Select (Thermo) for 5 minutes at 37° C., washed twice with HBSS, and resuspended in 1 mL at a concentration of ~6 M cells/mL. Cell number and viability were measured using a Countess II Automated Cell Counter (ThermoFisher). Four mL ice-cold methanol was added slowly with constant mixing, and the resulting cell suspension incubated at −20° C. for at least 20 minutes. Cells were stored at −20° C. until sample labeling and scRNA-seq.

Flow Cytometry and Fluorescence Microscopy

Yeast cells (Fleischmann's Rapid Rise) were used as an abundant cellular substrate to test cell labeling reactions. Approximately 5 g of dehydrated cells were rehydrated in 4 mL PBS+0.1% Tween-20 (Sigma) for 10 minutes at room temperature with rotation. One mL of the resulting cell suspension was diluted with 7 mL PBS-Tween and fixed by slow addition of 32 mL ice-cold methanol with constant mixing. Cells were incubated at −20° C. for at least 20 minutes before further use.

Methanol-fixed cells were rehydrated by combining 700 µL HBSS with 500 µL fixed cells in 80% methanol. This suspension was centrifuged at 3,000×g for 5 minutes, then washed twice more with HBSS. Cells were resuspended in 1 mL HBSS, and 50 µL of this cell suspension was used for cell labeling. Methyltetrazine-Cy5 (Click Chemistry Tools) was added to 2 µM final concentration, NHS-TCO to 5 µM, and DAPI to 1 µg/mL. Cell labeling reactions were incubated for 30 minutes at room temperature with rotation then quenched by addition of Tris-HCl to 10 mM and methyltetrazine-DBCO (Click Chemistry Tools) to 50 µM. Samples were diluted 20-fold in HBSS and analyzed on a MACSQuant VYB flow cytometer.

Fluorescence microscopy samples were prepared as above except NHS-TCO was used at 1 µM and MTZCy5 was used at 62.5 µM. Samples were imaged on a Zeiss LSM 800 laser scanning confocal microscope.

Sample Labeling Proof of Concept

Fixed NSCs were split into four aliquots with ~400,000 cells in 100 µL 80% methanol. Live NSCs were prepared as described above, washed into HBSS, and similarly aliquoted to four samples with 400,000 cells in 100 µL. Prior to cell labeling, 8 labeling combinations were made by combing 6 µL each of two different sample tags. A 5-minute pre-incubation reaction was performed in the dark at room temperature by addition of 4 µL 1 mM NHS-TCO. After pre-incubation, cell suspensions were thoroughly mixed with the entire volume of a single sample label mix. Cell labeling proceeded for 30 minutes at room temperature on a rotating platform. Reactions were quenched by addition of Tris-HCl to 10 mM final concentration and methyltetrazine-DBCO (Click Chemistry Tools) to 50 µM final concentration. After quenching for 5 minutes, cells were pooled to create a single sample for fixed cells and a single sample for live cells. The two samples were combined with two volumes PBS-BSA and pelleted by centrifugation at 500×g for 5 minutes. Cells were washed three times with PBS-BSA and vigorously resuspended in a final volume of 150 µL. Cells were analyzed and counted, then fixed and live samples were combined at equal concentration and loaded onto a single lane of the Chromium Controller (10x Genomics, Inc.) targeting 10,000 cells. Library preparation was adapted from the REAP-Seq protocol. The 10x Genomics v2 Single Cell 3' seq Reagent kit protocol (10x Genomics) was used to process samples according to the manufacturer's procedure with modifications as follows. After initial amplification of cDNA and sample tags, the two libraries were separated during SPRI size-selection. The manufacturer's instructions were used to complete cDNA library preparation. For sample tags, rather than discarding 80 µL SPRI supernatant, this fraction was added to 45 µL SPRI beads and incubated at room temperature for 5 min. The SPRI beads were washed twice with 80% EtOH and sample tags eluted in 20 µL nuclease-free water. Table 2 depicts the reverse primers (SEQ ID NOs: 41-44) and forward primer (SEQ ID NO: 45) used to amplify sample tag libraries. The reverse primers, in some embodiments, are staggered oligonucleotides designed to improve sequencing quality for low-complexity barcode libraries. Sample tags were quantified by Qubit High-Sensitivity DNA Assay (Invitrogen) and amplified using primer R1-P5 and indexed reverse primers as appropriate. PCR was performed in a 25 µL volume including 2.5 µL sample tag library, 1.5 uL of 10 uM forward and reverse primer, 7 µL nuclease-free water, and 12.5 µL KAPA 2×HIFI PCR master mix (Kapa Biosystems). The samples were cycled as follows: 98° C. 3 min, 16 cycles of: 98° C. 20 sec, 58° C. 30 sec, and 72° C. 20 sec; and then a final extension step of 72° C. for 4 min. Final sample tag libraries were obtained using a PippinPrep automated size selection system with a 3% agarose gel set for a broad purification range from 200-250 bp (target library size is 225 bp). A Qubit assay was again used to determine library concentration for sequencing. Sample tag and cDNA libraries were analyzed on a BioAnalyzer High Sensitivity DNA kit (Agilent). Example traces are depicted in FIG. 6 for reference. Sample tag libraries were sequenced on an Illumina MiSeq using a MiSeq V3 150 cycle kit (26×98 bp reads), and cDNA libraries were sequenced on an Illumina HiSeq 4000 using a HiSeq SBS 3000/4000 SBS 300 cycle kit (2×150 bp reads).

TABLE 2

PRIMERS TO AMPLIFY SAMPLE TAG LIBRARIES

| Name | SEQ ID NO: | Sequence |
|---|---|---|
| P7 + A1.3_11 bpS3v4 | 41 | CAAGCAGAAGACGGCATACGAGATTCGGCGT CGATGCTGGAGTTCAGACGTGTGCTCTTCCG ATCTATGGGATGTCGTCGGCAGC |
| P7 + A1.2_11 bpS2v4 | 42 | CAAGCAGAAGACGGCATACGAGATCTAAACG GGTGACTGGAGTTCAGACGTGTGCTCTTCCG ATCTATGGGATTCGTCGGCAGC |
| P7 + A1.1_11 bpS1v4 | 43 | CAAGCAGAAGACGGCATACGAGATGGTTTAC TGTGACTGGAGTTCAGACGTGTGCTCTTCCG ATCTATGGGATCGTCGGCAGC |
| P7 + A1.4_11 bpS0v4 | 44 | CAAGCAGAAGACGGCATACGAGATAACCGTA AGTGACTGGAGTTCAGACGTGTGCTCTTCCG ATCTATGGGTCGTCGGCAGC |
| R1-P5 | 45 | AATGATACGGCGACCACCGAGATCTACACTC TTTCCCTACACGACGCTCTTCCGAT |

Species Mixing and Sample Label Multiplexing

Methanol-fixed human HEK293T and mouse NSCs were prepared as described above. As depicted in Table 3, samples were labeled with non-overlapping tags sets of increasing size. Suspensions of both cell types were prepared at 700,000 cells/mL in 80% methanol. Samples of 100 uL were prepared for each condition, with species mixing conditions comprising 50 µL of cell suspension from each species. For this experiment, 3'-modified oligonucleotides isolated by standard desalting were used as opposed to the 5'-modified, HPLC-purified oligonucleotides used in all other experiments presented. Tag sets were prepared by reacting 6 µL of each oligo along with 2 µL of 1 mM NHS-TCO per oligo at room temperature. After 5 minutes, the entire volume of each tag set was added to the appropriate cell suspension. Cell labeling was performed for 30 minutes at room temperature on a rotating platform. Reactions were quenched as above, pooled, and added to 2 mL PBS+1% BSA. Samples were split across two Eppendorf tubes and centrifuged at 500×g for 5 minutes. Cell pellets were resuspended in 500 µL PBS-BSA, combined, and centrifuged once more. The cell pellet was washed twice more with 1 mL PBS-BSA. Finally, the cells were resuspended in 150 µL PBS-BSA, counted, and diluted to $1\times10^6$ cells/mL and loaded on a single lane of the Chromium Controller targeting 12,000 cells. Sample tag and cDNA libraries were prepared as described. Libraries were submitted as part of an Illumina NovaSeq library, targeting 500 M reads total (2×150 bp reads), with sample tags submitted at 10% of the total library concentration.

TABLE 3

NON-OVERLAPPING TAGS SETS OF INCREASING SIZE

| Sample Number | Species | Number of Tags | Sample Tag(s) |
|---|---|---|---|
| 1 | Mouse | 1 | BC41 |
| 2 | Human | 1 | BC42 |
| 3 | Mouse | 2 | BC43, BC44 |
| 4 | Human | 2 | BC45, BC46 |
| 5 | Mixture | 2 | BC47, BC48 |
| 6 | Mixture | 3 | BC49, BC50, BC51 |
| 7 | Mixture | 4 | BC52, BC53, BC54, BC55 |
| 8 | Mixture | 5 | BC56, BC57, BC58, BC59, BC60 |

96-Sample Growth Factor Screen

Figure 4:
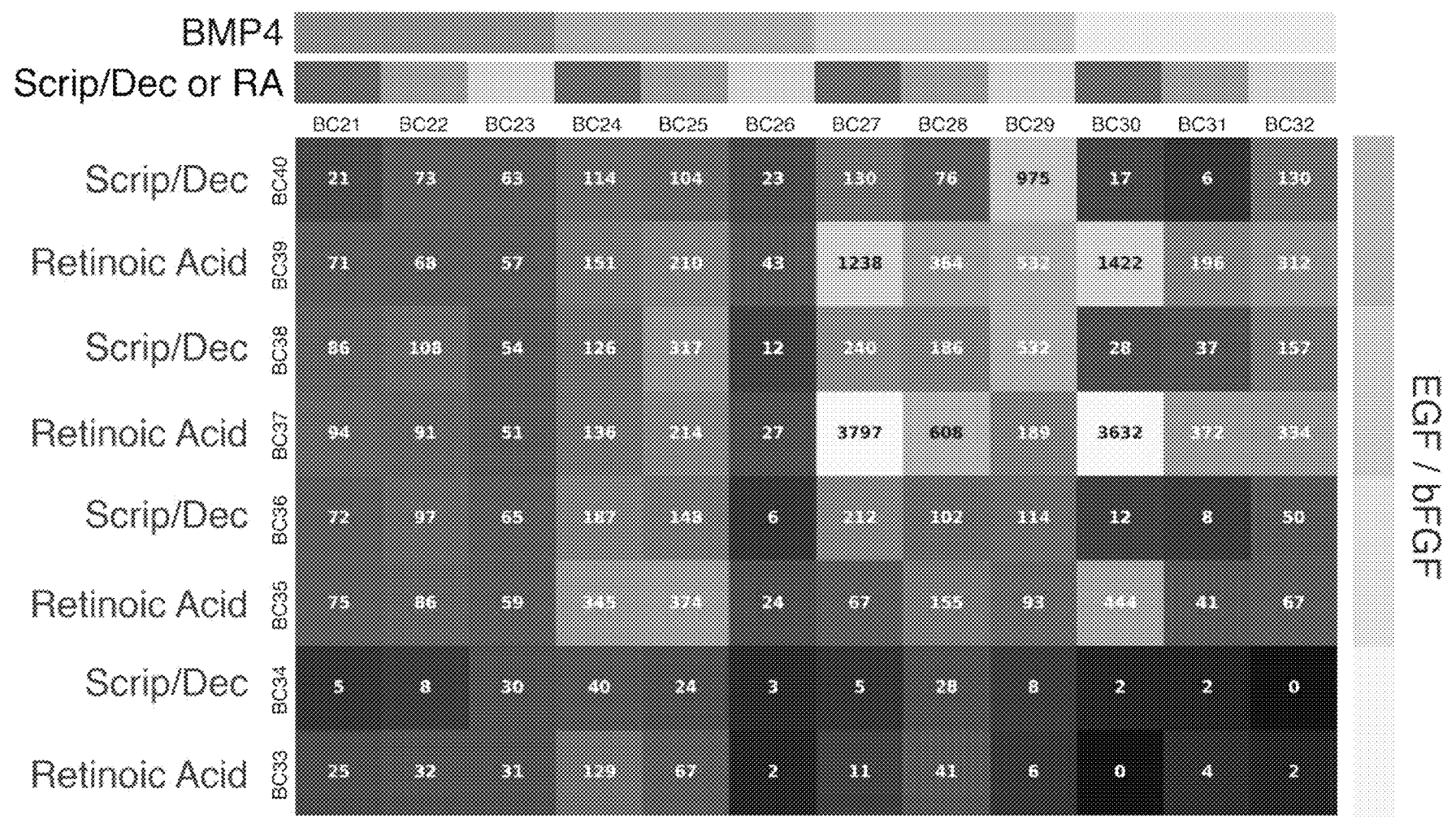

Cells for the 96-sample perturbation experiment were prepared as described above. For each sample, two sample tags (6 µL each) were combined with 4 uL 1 mM NHS-TCO according an 8×12 matrix. As shown in FIG. 4, columns 1-12 of the 96-well plate correspond to tags BC21-BC32, while rows A-H correspond to tags BC33-BC40. Fixed cells from each experimental condition (100 µL) were labeled with the entire volume of the corresponding sample tag mix for 30 minutes at room temperature on a rotating platform. Samples were quenched as described above, pooled, and combined with 15 mL PBS-BSA. Samples were split across two 15-mL conical tubes and spun at 500×g for 5 minutes. Cell pellets were resuspended in 3 mL PBS-BSA each and centrifuged again. The pellets were washed twice with one mL PBS-BSA and resuspended in a final combined volume of 200 uL. Cells were loaded on two lanes of the 10× Chromium Controller targeting 10,000 cells per lane. Sequencing libraries were prepared as described, with sample tag libraries sequenced on two lanes of Illumina MiSeq using MiSeq v3 150 cycle kits (26×98 bp reads), and cDNA libraries pooled and sequenced on Illumina HiSeq 4000 using two HiSeq 3000/4000 SBS 300 cycle kits (2×150 bp reads).

cDNA Data Processing

Standard bioinformatics tools were used to process and analyze DNA sequencing information. Raw sequencing data were processed using the 10× Genomics Cell Ranger pipeline (version 2.0). Cellranger mkfastq was used to demultiplex libraries based on sample indices and convert the barcode and read data to FASTQ files. Cellranger count was used to identify cell barcodes and align reads to mouse or human transcriptomes (mm10 and hg19) as appropriate. For the 96-sample perturbation experiment, cellranger aggr was used to combine and normalize sequencing data from the two 10× lanes split across two HiSeq lanes. Cells were selected by cellranger using the inflection point of detected cell numbers as a function of ordered read counts as a cutoff. For the sample labeling proof of concept and species mixing experiments, no further analysis of the cDNA data was performed.

Sample Tag Data Processing and Assignment

Sequencing reads from sample tag libraries were processed using cellranger and synthetic 'transcriptomes' corresponding to the sequences of the tags used in a given experiment. Cellranger count outputs a postsorted genome BAM file containing error-corrected cell barcodes and UMIs as well as read2 sequence containing sample tag information. The post-sorted genome BAM file was used to generate a digital count matrix for the sample tags corresponding to each cell barcode. A modified version of CITE-Seq Count was used to count sample tag data. Briefly, a fuzzy matching package, "fuzzywuzzy" (github.com/seatgeek/fuzzywuzzy), was implemented to find the sample barcode region in staggered sample tag libraries that were synthesized to improve sequencing quality. Tag reads were summed according to the combinations used in a given experiment, and sample calling was based simply on the sample with the highest number of reads. Sample assignment was performed by querying the sample tag matrix with cell barcodes identified from cDNA data, generating a vector of sample assignments that can be input into standard scRNA-seq analysis packages. For Example 4, in which up to five tags were used for each cell, t-SNE was performed on the sample tags x cells count matrix while k-means clustering was performed on a normalized count matrix in which the counts corresponding to each cell were first (1) collapsed and normalized according to the tag sets used (Table 3) by adding the tag counts corresponding to each sample and dividing by the size of the tag set then (2) dividing each normalized sample count by the sum of all normalized samples for that cell.

Data Analysis

Figure 5A:
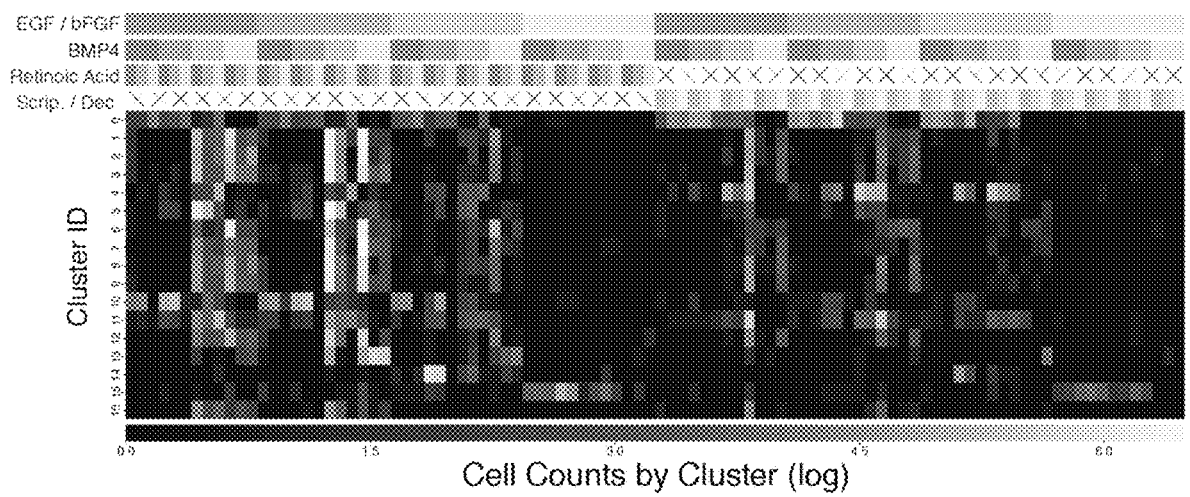
FIGS. 5A-C depict data related to the cellular response to 96 unique combinations of growth factors in the 96-plex perturbation experiment.
Figure 5A:
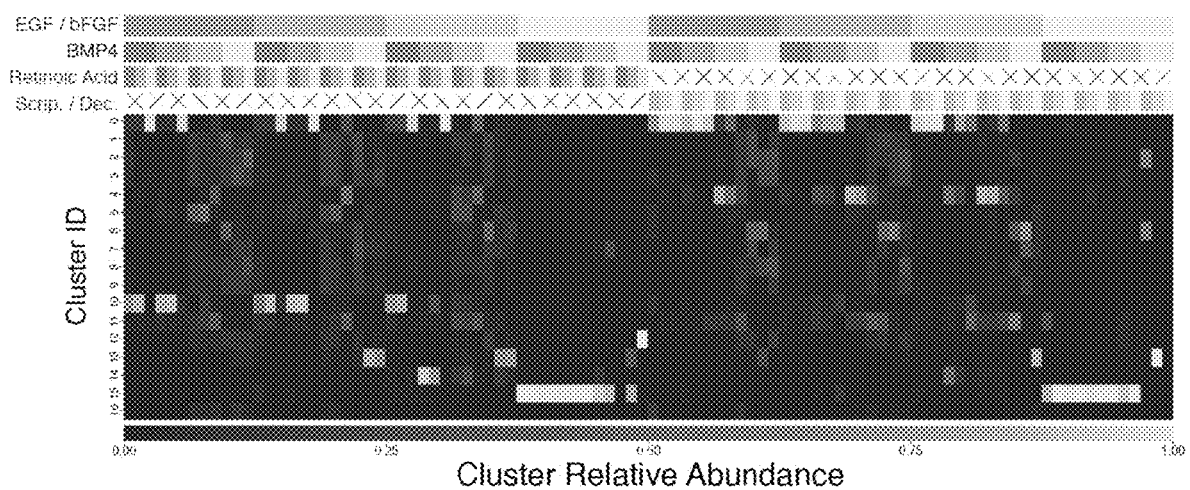
Figure 5B:
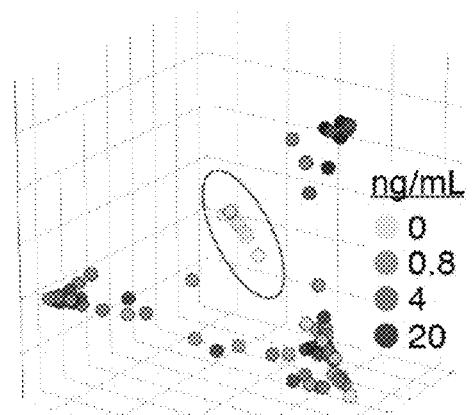
Figure 5B:
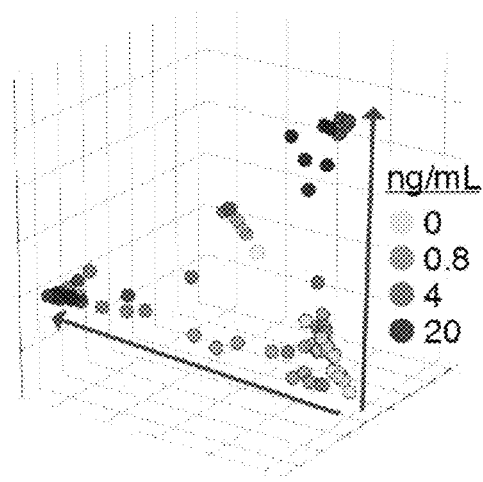
Figure 5B:
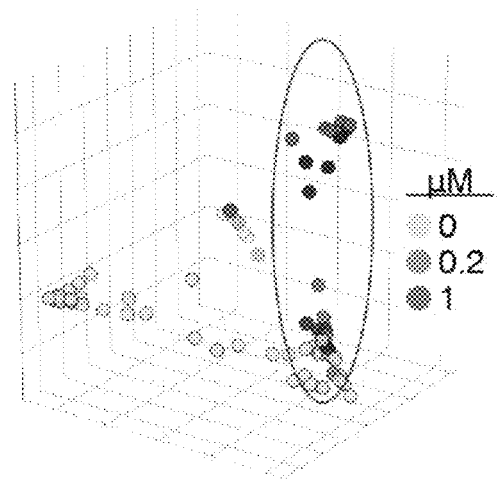
Figure 5B:
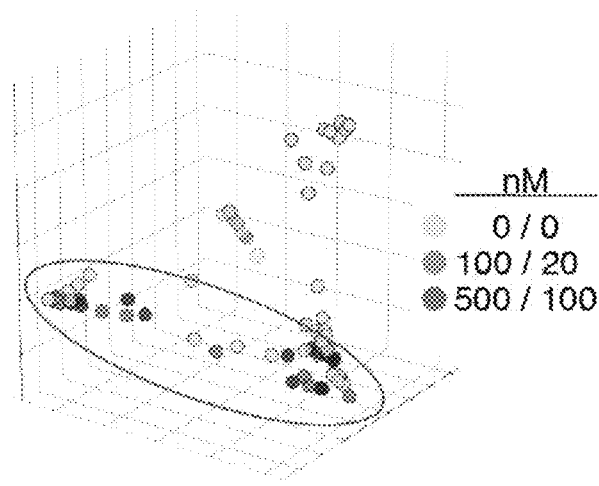
Figures 5C, 5D:
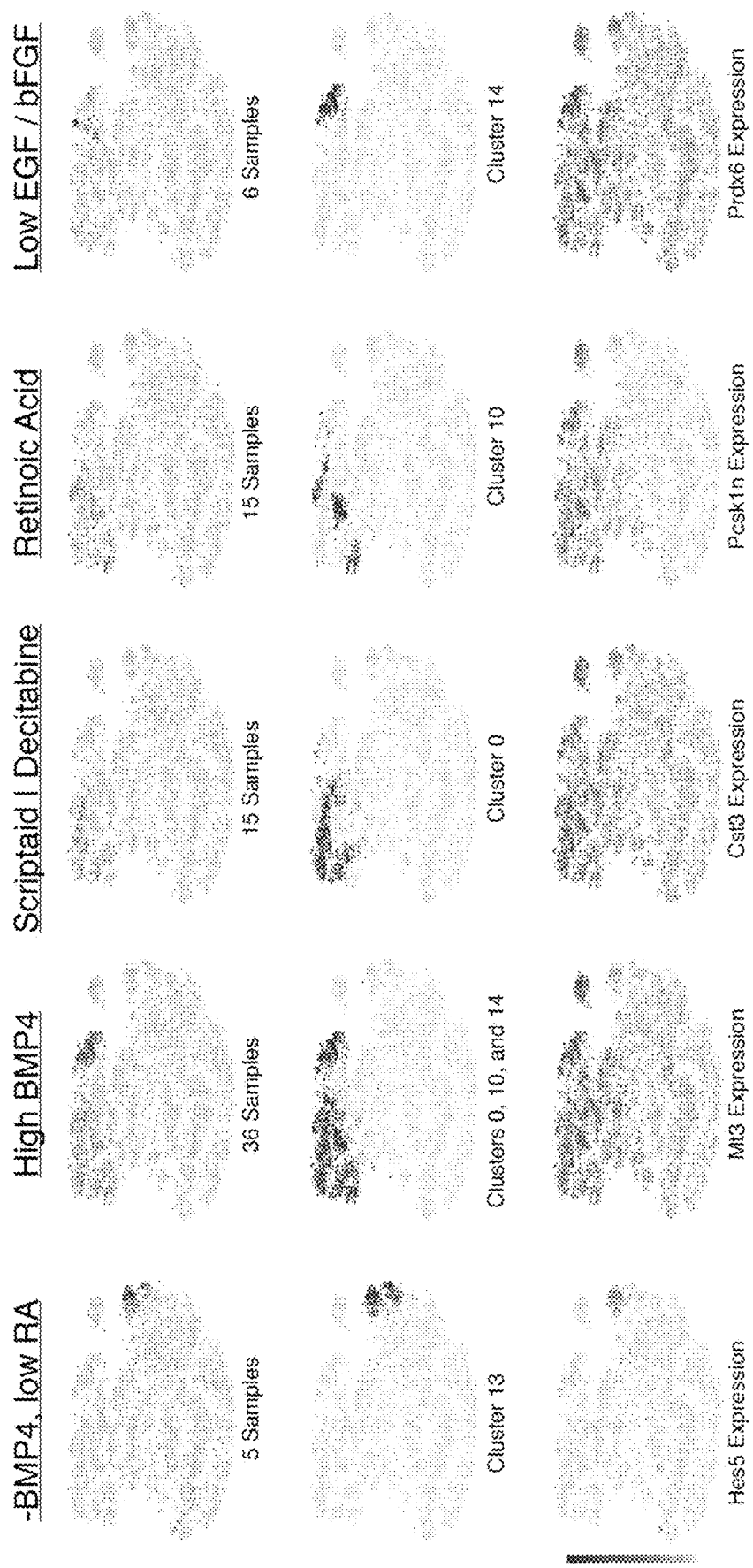
FIG. 5D depicts t-SNE projection plots showing that 36 samples from high BMP4 conditions map to clusters 0, 10, and 14, each specific to localized regions of the perturbation space. Expression of top differentially expressed genes for each selected group is shown.

For the 96-sample perturbation experiment, the ScanPy Python package (version 1.0.4) was used to process the filtered genes×cells matrix produced by cellranger. The data was log transformed, normalized per cell, and highly variable genes were selected as those with mean normalized counts>0.0125 and <3 and with dispersion>0.5, giving 1,221 highly variable genes. The per-cell read counts were regressed out and the data scaled to unit variance. PCA was performed on this matrix, followed by t-SNE visualization based on the top 20 principal components. Clustering was performed using the neighbors and louvain tools in ScanPy with the size of the local neighborhood set to 30. For clustering based on Louvain community detection, the resolution parameter was adjusted to agree well with subpopulations produced by the perturbation experiment. It was reasoned that these natural groupings represent reproducible, quantitatively distinct biological states under the conditions of the experiment and would thus hold the most information relevant to the changing experimental parameters. In practice, a resolution setting of 2 yielded clusters that agreed quite well with the sample-specific subpopulations produced by the perturbation experiment. Sample assignments were combined with cluster assignments from each cell to produce a matrix of cluster occupancy×experimental condition as well as a normalized version of the same matrix showing cluster relative abundance for each sample (FIG. 5A). Principal component analysis (PCA) was performed on the cluster relative abundance matrix to visualize relationships between the experimental conditions used in the perturbation (FIG. 5B). Differential expression analysis was performed with the rank_genes_groups function in ScanPy. The top differential genes between the cluster(s) of interest and the rest of the dataset are shown (FIGS. 5C-5D).

Example 1

Optimization of the Sample Tagging Method

Figure 2B:
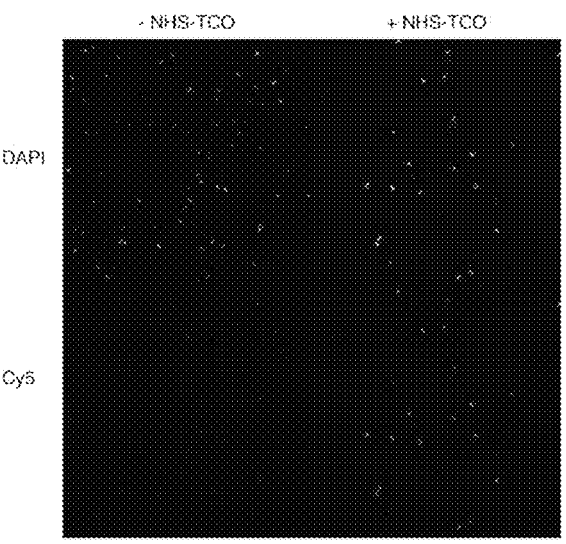
Figure 2C:
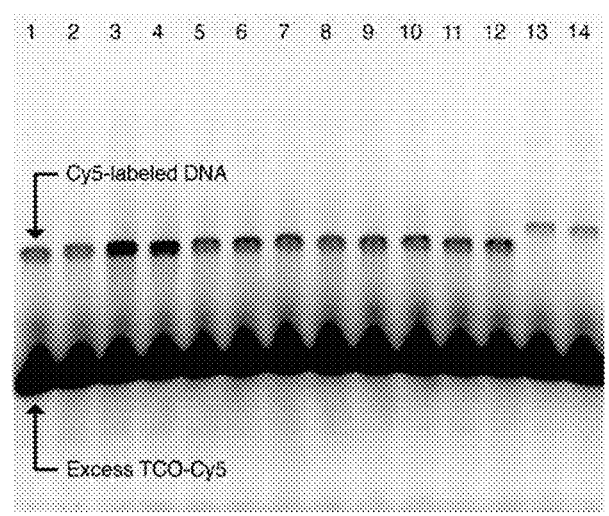
FIG. 2C depicts a polyacrylamide gel of the separated products of MTZ-DNAs reacted with TCO-Cy5. Lanes 1-12 are 3'-amine modified oligonucleotides, while lanes 13 and 14 are 5'-amine modified oligonucleotides.

The sample tagging approach was evaluated and optimized using microscopy and flow cytometry. Fluorescent chemical probes were used to screen reaction conditions, and promising reaction conditions were confirmed by fluorescence in situ hybridization (FISH). It was found that a large number of oligonucleotides could be immobilized onto the target cells in less than 20 minutes under both physiological aqueous and methanol fixation conditions. FIGS. 2A-2B depict the results of direct yeast cell labeling with Inverse Electron-Demand Diels-Alder (IEDDA) chemistry. As depicted in FIG. 2A, yeast cells were fluorescently labeled in a one-pot, two-step reaction with NHS-TCO and MTZ-Cy5 (while control reactions omitting NHS-TCO failed to generated Cy5-fluorescent cells). Further, fluorescence microscopy of yeast cells labeled with NHS-TCO and MTZ-Cy5 showed labeling only in the presence of NHS-TCO cross-linker (FIG. 2B). MTZ-DNAs were reacted with TCO-Cy5 and the products were separated by polyacrylamide gel electrophoresis. FIG. 2C depicts an activity assay for the panels of methyltetrazine-activated DNA sample tags, with lanes 1-12 depicting the results for 3'-amine modified oligonucleotides, while lanes 13 and 14 depict the results for 5'-amine modified oligonucleotides.

With a viable chemical labeling scheme developed, optimized library prep procedures were then developed to produce separate sequencing libraries for cDNAs and sample tags. Mock library preps with and without sample tags were used to optimize sample tag amplification and isolation. Various PCR amplification designs were tested, and a matrix of cell tag concentration×PCR cycle number was produced and evaluated by sequencing, providing a general cell tagging protocol.

Next, the utility of multiplex scRNA-seq in the context of an experimental screen was investigated. Correlations between pooled or unpooled matched samples were compared. As evidenced by the higher correlation between pooled samples, significant batch effects were present in unpooled samples even when attempting to produce exactly matched datasets in parallel.

Example 2

96-Plex scRNA-Seq Perturbation Experiment

To showcase the power of the method of performing multiplex scRNA-seq provided herein, the differentiation response of neural stem cells to a large array of growth factor concentrations and combinations was explored. Such an experiment, which produces a unique cell population in each condition, would be technically and financially inaccessible without a cost-effective means of sample pooling.

Figure 3A:
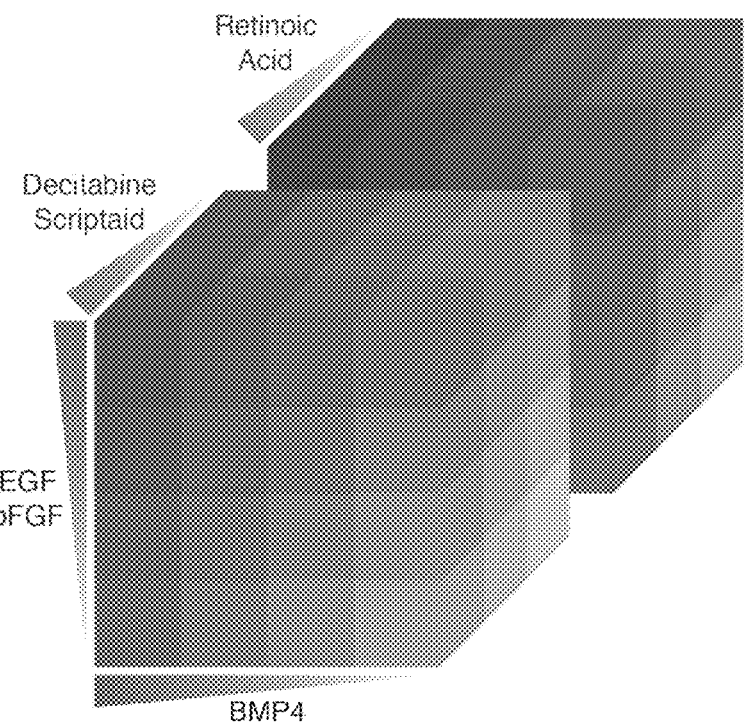
FIGS. 3A-E depict the results of a 96-Plex scRNA-Seq experiment performed using the sample tagging method of the disclosure.
Figure 3B:
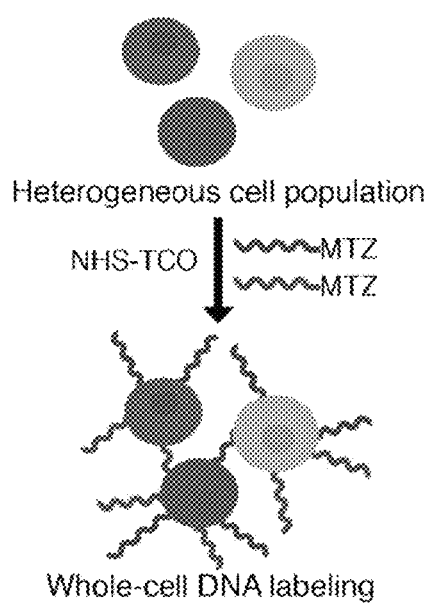
Figure 3C:
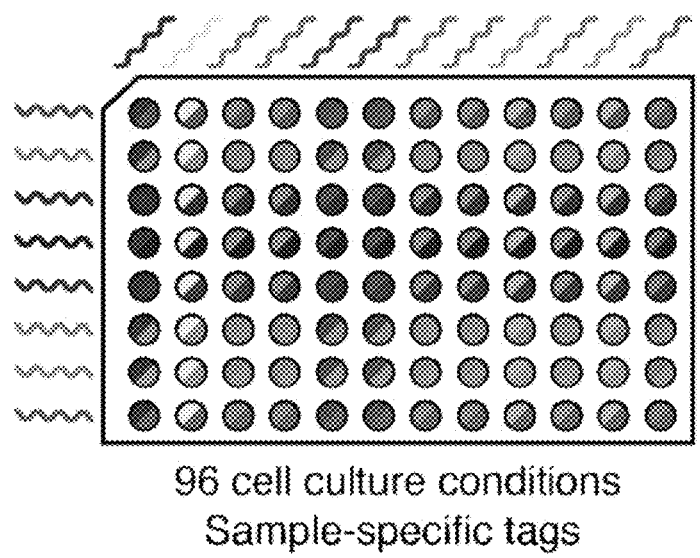

Neural stem cells (NSCs) are known to differentiate into many unique cell types in vivo, primarily neurons, astrocytes, and oligodendrocytes. In vitro, NSCs can be forced into different differentiation trajectories by exposing the cells to a variety of synthetic chemicals, hormones, and growth factors. The response of NSCs to varying concentrations of Scriptaid/Decitabine, epidermal growth factor (EGF)/basic fibroblast growth factor (bFGF), retinoic acid, and bone morphogenic protein 4 (BMP4), was investigated by producing a 4×4×6 perturbation array representing a large space of experimental conditions (FIG. 3A). NSCs were cultured in a single 96-well plate with each sample corresponding to a unique combination of factors (FIG. 3C and FIG. 4). After chemical DNA labeling (depicted in FIG. 3B), the samples were pooled and subjected to a modified version of the 10× Genomics Single-Cell Expression protocol. A total of 21,232 cells were detected based on cDNA counts, and sample assignment was performed for the detected cells based on the sample tags with the highest UMI counts. FIG. 4 shows the non-limiting exemplary organization of a 96-plex perturbation experiment (matrix entries correspond to the number of cells recovered from each sample).

Figure 3D:
Figure 3E:
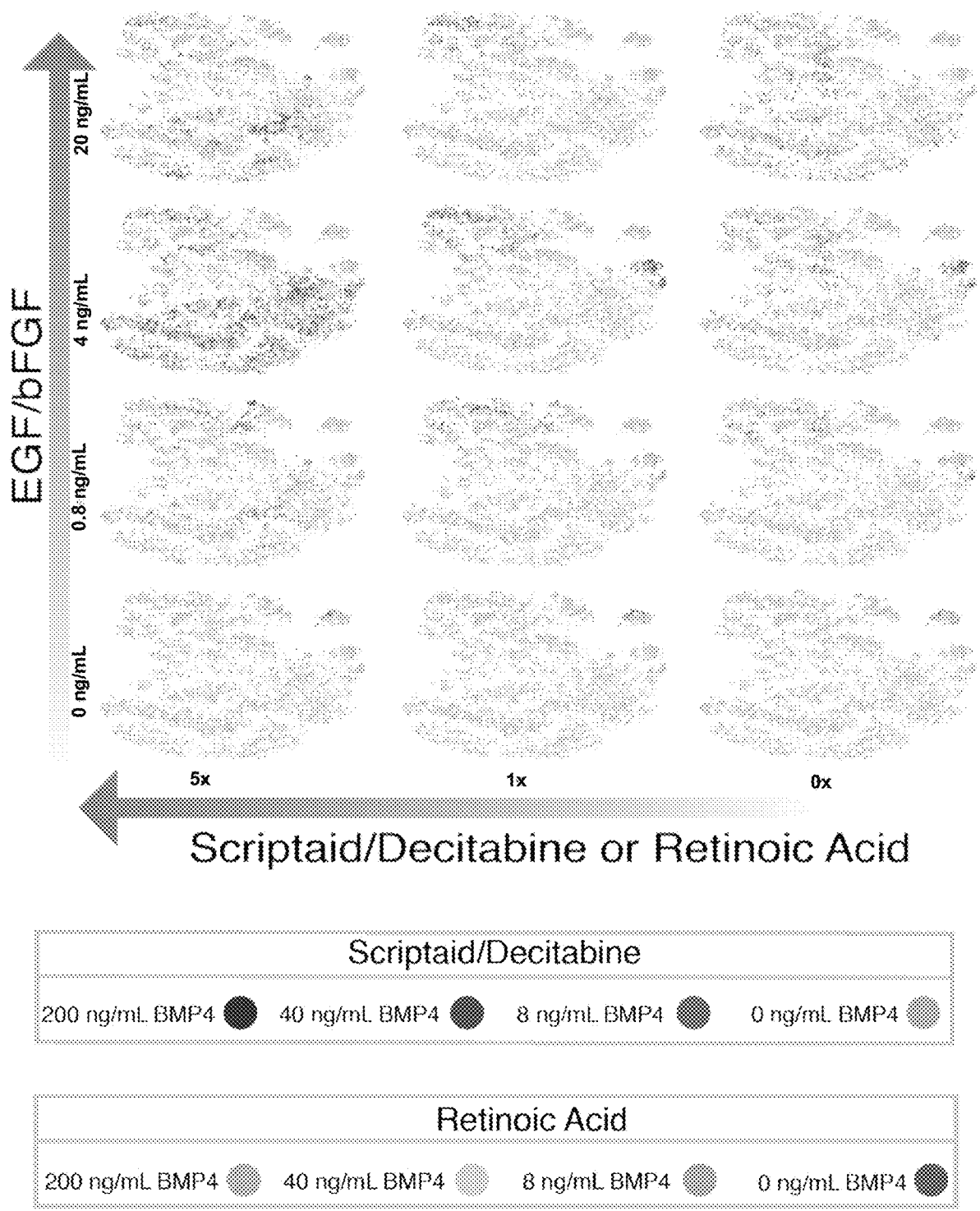

Visualization of the cell populations produced by each experimental condition revealed a complex interplay between the perturbations used in this 96-plex experimental space (FIG. 3E). On a global level, cell proliferation varied widely across the experiment, revealing growth rates specific not just to each condition but also to each cell state across the experiment. Highly proliferative states (clusters 1, 2, 3, 6, 7, 8, 9, 12, and 16), which account for large regions of the cell state space when plotted according to t-SNE, differentially express various genes associated with cell growth and the cell cycle, including ribosomal, cytoskeletal, and cyclin-dependent proteins. Conversely, samples deprived of EGF/bFGF exhibited apoptotic phenotypes including low cell counts and expression of stress response genes such as Cryab, Mt1, and Gpx4. A goal of this experiment was to define the cell states produced by the array of experimental conditions, a frequently challenging procedure in scRNA-seq analysis and a potential roadblock to perturbation experiments where the presence of classical marker genes may depend on experimental conditions. Identification of functional cell states was greatly aided by the large number of samples in this experimental perturbation. Various distinct regions of transcriptome space were repeatedly populated by cells originating from multiple samples in localized regions of perturbation space, forming natural groupings of cells that were validated and assigned by clustering using Louvain community detection (FIG. 3D). As seen in FIG. 3D, cluster assignments closely match population behavior driven by experimental parameters.

Plotting the cluster occupancy of each sample revealed the structure of the cell populations produced across the experiment (FIG. 5A). Overall trends, such as high proliferation under low BMP4 conditions and high cluster specificity under high BMP4 conditions, are readily observed. Principal component analysis of the relative cluster abundance×sample matrix was used to identify relationships between the experimental inputs (FIG. 5B). The experimental perturbations associate directly with the cell populations observed in the scRNA-seq samples. The absence of EGF/bFGF has a drastic effect, yielding an isolated group of samples, while BMP4 concentration has a graded effect and a strong interaction with either Scriptaid/Decitabine or retinoic acid, each of which produces a separate branch of samples when combined with the two highest BMP4 concentrations. This analysis demonstrates that multiplexed scRNA-seq can be used to classify cell populations and interpret the conditions that produced them. In the context of a perturbation experiment, relevant features of the experimental space can be learned, e.g. the strong effect of BMP4 concentration shown here. Additionally, also of great interest is extension of this proof-of-principle to biomedical diagnostics: by applying Bayes Rule to the relative cluster abundance×samples matrix, it will be possible to infer disease conditions from high-resolution cell population observations.

After evaluating the high-level information that can be gleaned from a large perturbation array, two regions of this experimental space were closed examined to illustrate the depth of analysis afforded by multiplexed scRNA-seq. First, an isolated portion of cell state space was explored, cluster 13, which was populated under a strict range of conditions with intermediate EGF/bFGF concentrations, no BMP4, and moderate to no retinoic acid. Cells from just five samples accounted for practically all the cells in cluster 13 and little across the rest of cell state space, exhibiting strong condition dependence (FIG. 5C). Differential expression analysis showed that this cluster is strongly enriched for Hes5, a gene with important roles in cell fate determination.

A more complex cellular response was observed under high BMP4 conditions, where numerous cell states were identified, many populated only within a small region of experimental space. Cells from conditions with ≥0.8 ng/mL EGF/bFGF and BMP4≥4 ng/mL, 36 samples in total, mapped to just three clusters (0, 10, and 14) which were further subdivided by orthogonal experimental factors (FIG. 5D). The cell state defined by cluster 14 was not observed in samples with high EGF/bFGF, high BMP4, or high Scriptaid/Decitabine or retinoic acid concentrations. Instead, cells from those conditions were found in clusters 0 and 10, with cells treated with Scriptaid/Decitabine appearing almost exclusively in cluster 0, while those treated with retinoic acid mapped strongly to cluster 10 with secondary populations mapping to cluster 0.

Such a dissection of cellular response to perturbations has been a long-standing goal in cell biology. It has been hypothesized that cells occupy a relatively limited number of transcriptional states in response to disease or experimental perturbation, and elucidating the connections between various perturbations will help in understanding cellular behavior. One such endeavor, the Connectivity Map (CMap) project, is a large-scale effort to measure gene expression response to molecular perturbations. While impressive in scope—CMap has been used to profile more than a million perturbation experiments—major challenges have included batch effects, averaging across cell populations, and difficulty in examining conditions that yield very few cells. The multiplexing method disclosed herein overcomes these obstacles and provides single-cell whole-transcriptome resolution at very low cost.

This example demonstrates the utility and versatility of the sample tagging method disclosed herein in the context of a multifaceted experimental perturbation in which neural stem cells (NSCs) were exposed to 96 unique combinations of growth factors, with the perturbed cell populations profiled as a single pooled library (FIG. 3A). Despite the cell capacity of scRNA-seq platforms, single-cell transcriptome-wide analysis of such an experiment, which produces a unique cell population in each condition, has been technically and financially inaccessible in the absence of a suitable means of sample pooling. Analysis of the 96-plex perturbation experiment revealed changes in cell population structure and transcriptional states that cannot be discerned from bulk measurements, establishing a cost effective means to survey cell populations from large experiments and clinical samples with the depth and resolution of single-cell RNA-seq. This example introduces a powerful new experimental and analytical paradigm, underpinned by the flexible, scalable cell tagging method disclosed herein, in which the massive cell capacity of scRNA-seq is effectively leveraged to analyze and compare large numbers of cell populations.

Example 3

Multiplexing Live and Fixed Cell Samples

Figure 6A:
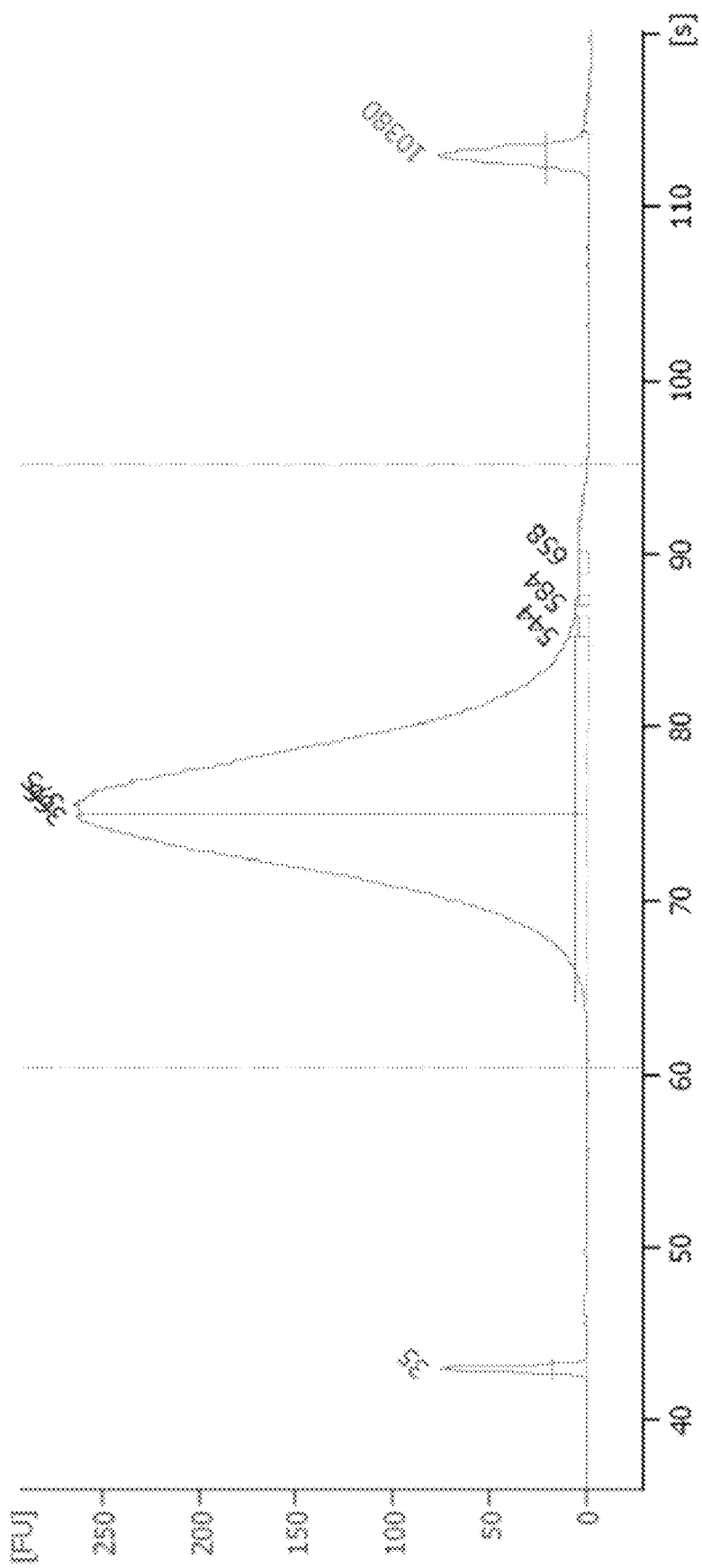
FIGS. 6A-6B depict exemplary BioAnalyzer traces for fragmented cDNA libraries (FIG. 6A) and sample tag libraries (FIG. 6B).
Figure 6B:
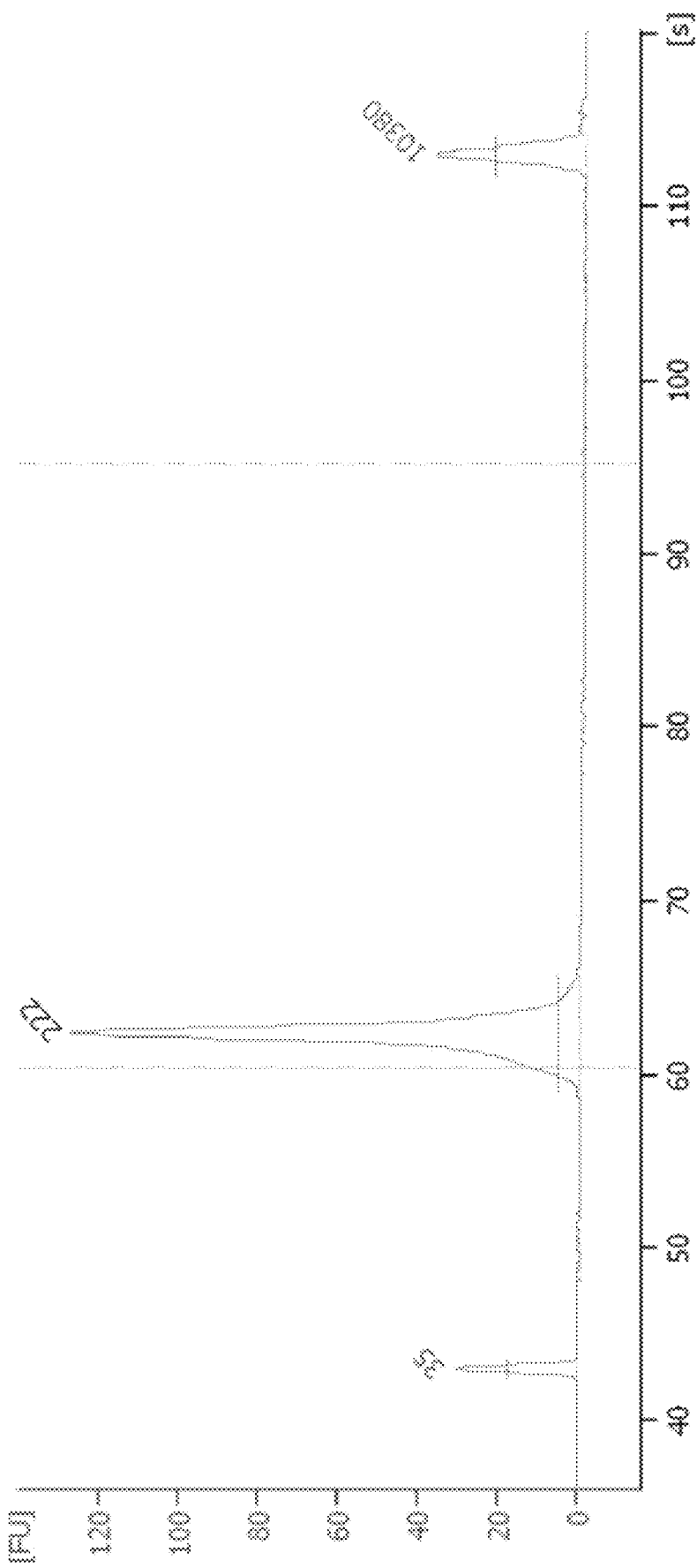
Figure 7C:
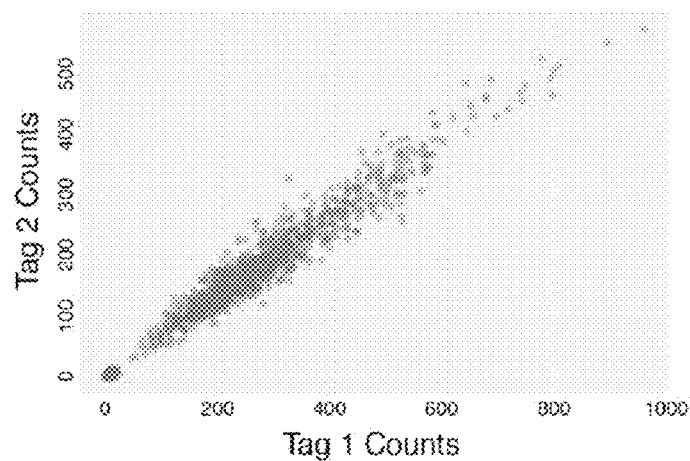
FIG. 7C depicts a scatter plot of counts for Tags 1 and 2, which were used to label the same sample. The low-count population (bottom-left) is background from droplets not containing cells from the sample, while the high-count population corresponds to positive cells from the sample and shows a striking correlation between the two tag counts (Pearson's correlation coefficient r=0.96).
Figure 7D:
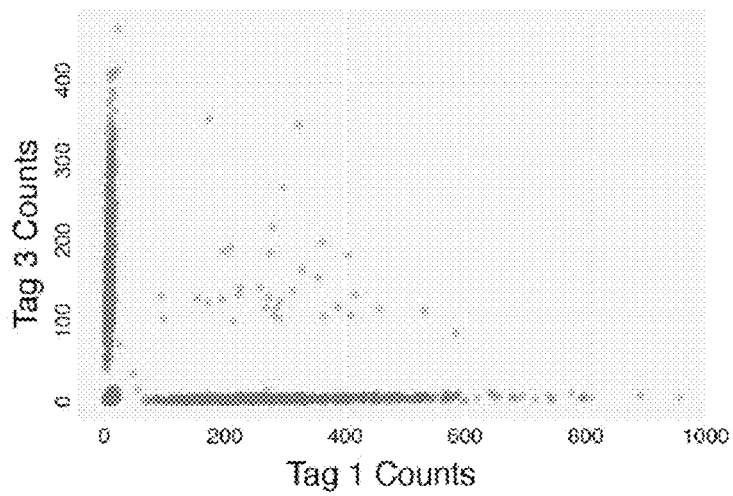
FIG. 7D depicts a "barnyard plot" showing two tags from separate samples.
Figure 7E:
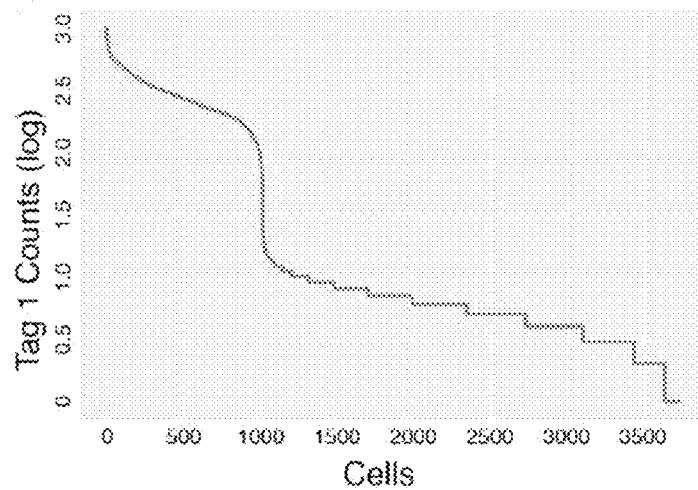
FIG. 7E depicts counts for Tag 1 from each cell in the experiment, ordered from highest to lowest and showing a clear inflection point between Tag 1 (+) and Tag 1 (−) cells.

To further validate the sample multiplexing method disclosed herein and explore its limits, a multiplexing experiment in which four samples of live mouse neural stem cells (NSCs) and four samples of methanol-fixed NSCs were each labeled with unique sets of two methyltetrazine-modified sample tags was undertaken. The samples were then quenched, pooled, and processed with the 10× Genomics Single-Cell Gene Expression Kit. FIGS. 6A-6B illustrate exemplary BioAnalyzer traces for fragmented cDNA libraries (FIG. 6A) and sample tag libraries (FIG. 6B). Analysis of sample tag profiles from methanol-fixed cells recapitulated matched pairs of sample tags, indicating efficient single-cell labeling, and permitting facile sample demultiplexing (FIG. 7). FIG. 7A depicts a heatmap showing 3,768 detected cells originating from four methanol-fixed samples each labeled by a pair of sample-specific tags. Cell doublet events were unambiguously detected as collisions of four pairs of tags corresponding to two separate samples. FIG. 7B depicts a t-SNE visualization of sample tag data colored by k-means clustering (k=4). Four main clusters were observed, corresponding to the four individual samples, as well as $$6 = \binom{4}{2}$$

small clusters corresponding to each possible combination of cell doublet originating from two different samples. FIG. 7C depicts a scatter plot of counts for Tags 1 and 2, which were used to label the same sample. The low-count population (bottom-left) is background from droplets not containing cells from the sample, while the high-count population corresponds to positive cells from the sample and shows a striking correlation between the two tag counts (Pearson's correlation coefficient r=0.96). In methanol-labeled samples, strong correlation between UMI counts for pairs of tags applied to the same samples was noted (FIG. 7C), suggesting that the extent of chemical tagging may be correlated with cell size. FIG. 7D depicts a "barnyard plot" showing two tags from separate samples. Tags are clearly orthogonal, with doublets easily identified. FIG. 7E depicts counts for Tag 1 from each cell in the experiment, ordered from highest to lowest and showing a clear inflection point between Tag 1 (+) and Tag 1 (−) cells.

Crucially, this example shows that cell tagging is equally applicable to live and fixed samples. Foregoing sample fixation enables sample multiplexing in conjunction with methods dependent on epitope preservation, and the disclosed labeling methods are sufficiently fast and robust to be completed in 20 minutes in any buffer compatible with NHS-ester conjugation (e.g., pH 7.0-8.5, devoid of buffer components containing primary amines). Alternatively, sample fixation can be invaluable for preservation of cell state and long-term storage of samples. In some embodiments, cell tagging performance is even better in this context, likely due to the improved kinetics of both IEDDA and NHS-ester reactions in methanol and the reduced rate of NHS-ester hydrolysis. Live cell labeling in aqueous solution resulted in diminished signal-to-noise, possibly a result of the high rate of NHS-ester hydrolysis in aqueous solution, along with the reduced rate of IEDDA reactions in water compared to methanol. Under methanol fixation conditions, cell tagging is a robust and flexible method for multiplex scRNA-seq with high capacity for tag multiplexing on individual cells. Compared to labeling strategies based on antibody-oligo conjugates, the chemical tagging methods disclosed herein are cheaper, not reliant on epitope markers, compatible with fixed cells, and, most notably, subject to chemical quenching, permitting high-throughput scRNA-seq analysis of low-input samples by pooling many cell populations before washing. While this example demonstrates multiplexing on the 10× Chromium system, the disclosed methods are compatible with other similar platforms (e.g. Drop-Seq, inDrops, sciRNA-seq, Bio-Rad's ddSEQ), and are readily extendible to full-length scRNA-seq and other single-cell genomic assays.

Example 4

Species Mixing and Tag Multiplexing

Figure 8A:
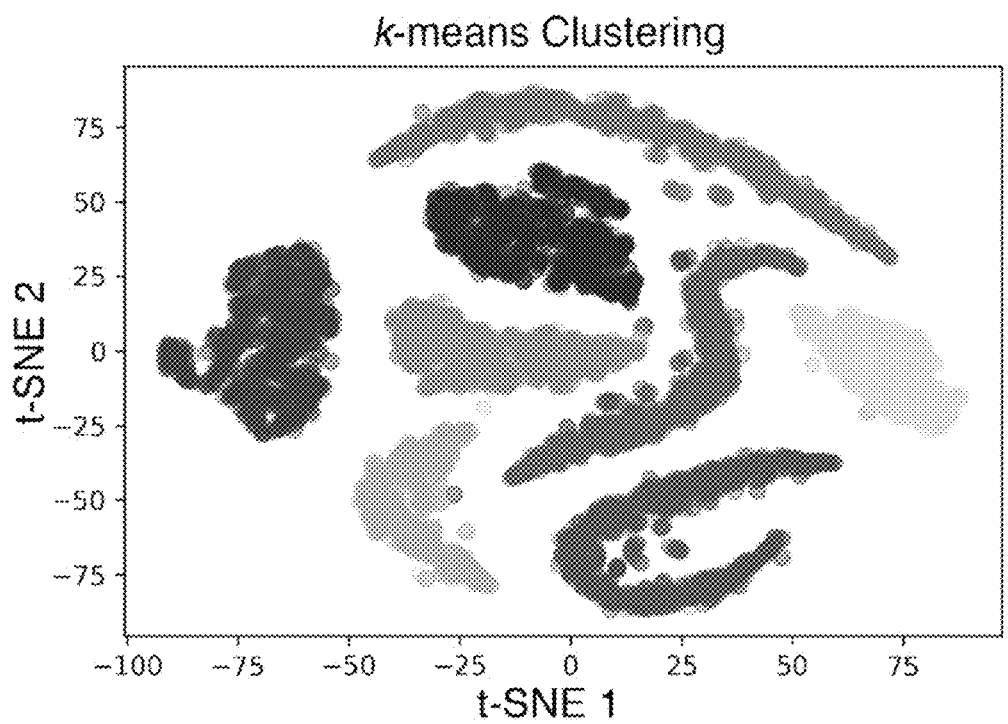
FIG. 8A depicts the 10,054 cells that were detected by a t-SNE projection plot of sample tags×cells count matrix (colored by sample assignment from k-means clustering performed on a matrix normalized for tag numbers and counts per cell).
Figure 8B:
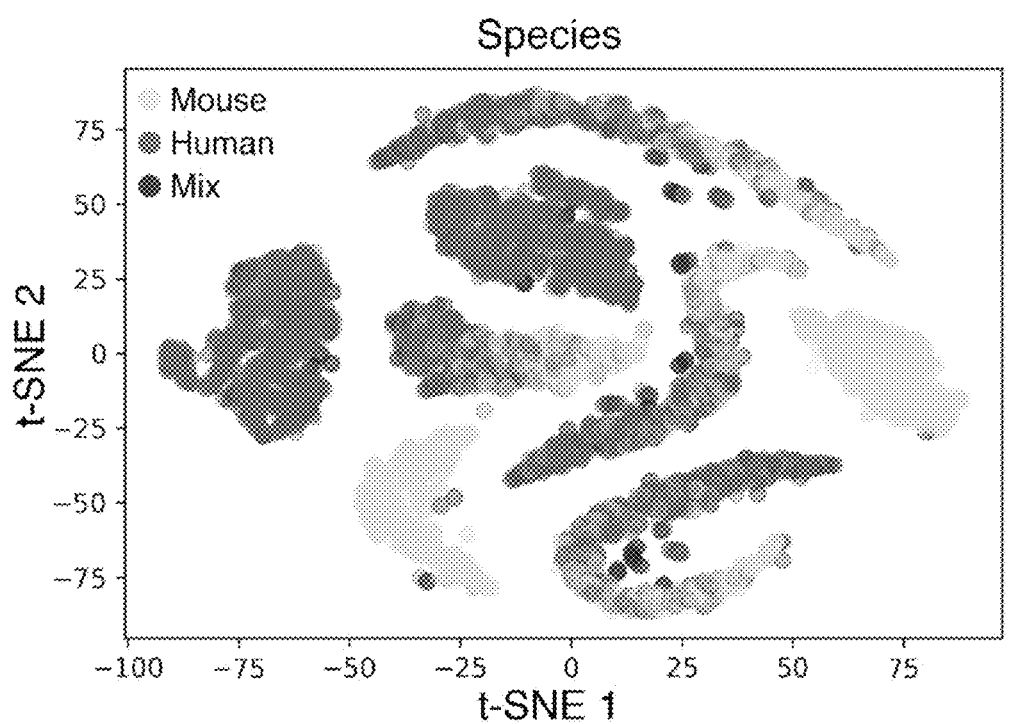
FIG. 8B depicts a t-SNE projection plot colored according to species assignment based on cDNA content.
Figure 8C:
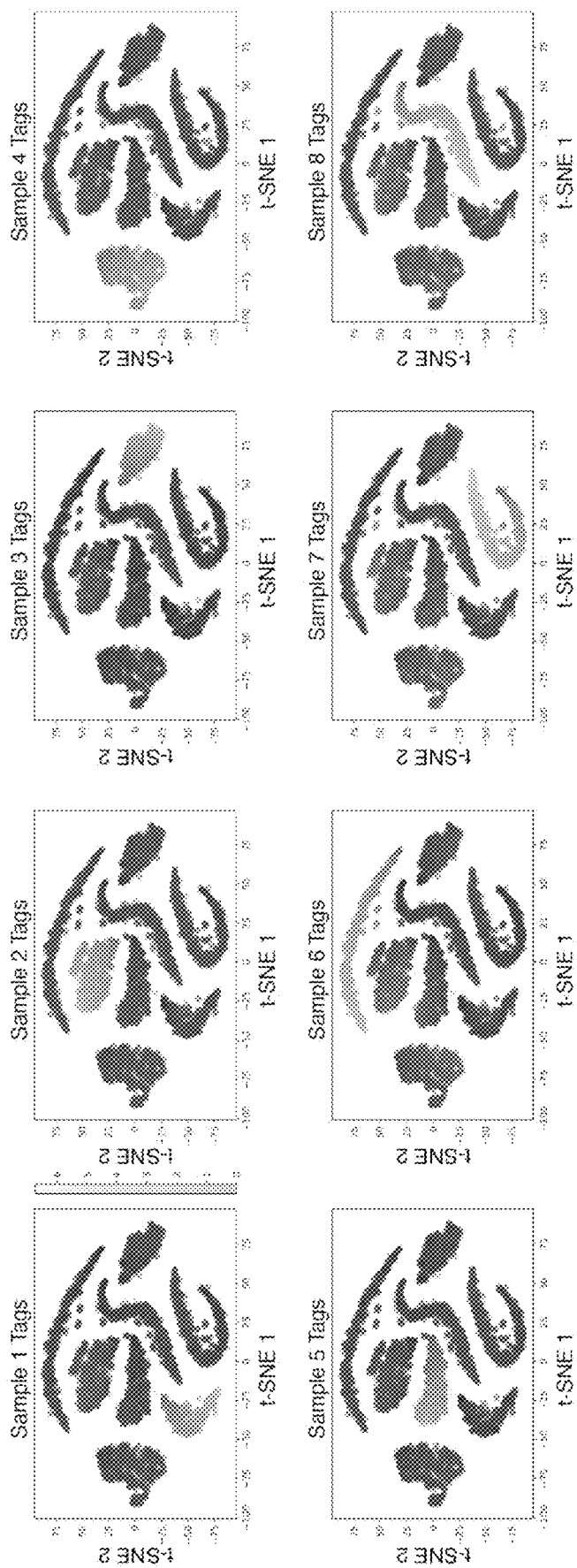
FIG. 8C depicts t-SNE representations with detected cells colored as the logarithm of the sum of sample tags used in each of the eight experimental samples.
Figure 8D:
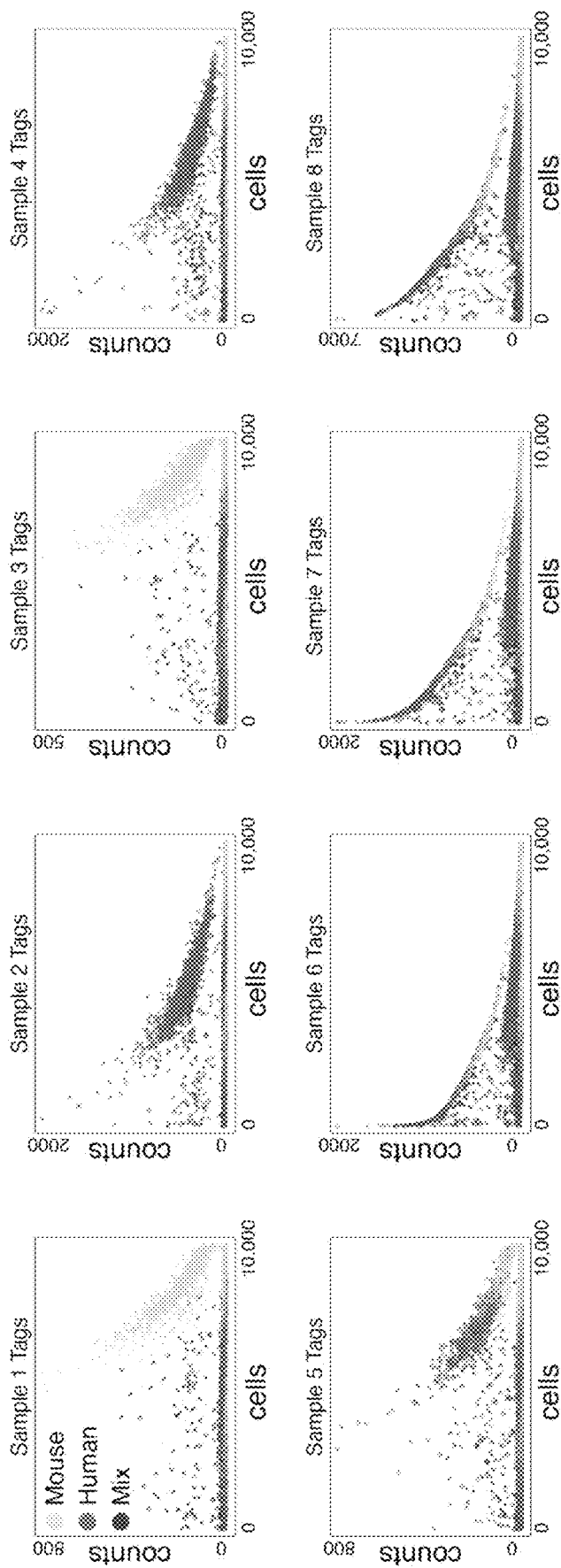
FIG. 8D depicts the sum of sample tag counts for each sample across all detected cells.

This example explores the limits of the cell tag multiplexing method provided herein. This example also tests the suggestion in example 3 that the extent of chemical tagging with the method disclosed herein is correlated with cell size. To test this hypothesis, a species-mixing experiment was devised in which large, human HEK293T cells and small, mouse NSCs were reacted individually and in combination with a series of non-overlapping sample tag pools of increasing size as depicted in Table 3. FIG. 8A depicts the 10,054 cells that were detected by a t-SNE projection plot of sample tags×cells count matrix (colored by sample assignment from k-means clustering performed on a matrix normalized for tag numbers and counts per cell). Eight major clusters are clearly identified. FIG. 8B depicts a t-SNE projection plot colored according to species assignment based on cDNA content. Four clusters represent a single species, and the remaining four are mixed, concordant with the experimental design. Cells identified as a mix of human and mouse are explained as cell doublets, and as expected fall outside of the major clusters, indicating a mix of sample tag signals as well. FIG. 8C depicts t-SNE representations with detected cells colored as the logarithm of the sum of sample tags used in each of the eight experimental samples. FIG. 8D depicts the sum of sample tag counts for each sample across all detected cells. Smaller NSCs present fewer sample tags than HEK293 Ts from the same samples, indicating a correlation between cell size and the extent of labeling.

This example demonstrates that the disclosed cell tagging method is a robust and flexible method for multiplex scRNA-seq with high capacity for tag multiplexing. It was found that up to 5 cell tags could be deposited on a single cell without loss of tag recovery, implying that 15,504 experiments could be multiplexed with a panel of just 20 tags. This example also demonstrates that the extent of cell labeling with the disclosed tagging method correlates with cell size, enabling a variety of applications. A strong correlation was observed between species of origin and sample tag counts, indicating the provided chemical tagging method is indeed sensitive to cell size, a relatively unexplored biological phenotype with intriguing implications for future work.

Experimental Materials and Methods

The following experimental materials and methods were used for Example 5 described below.

Overview of Cell Tagging Procedure

Barcoded DNA oligonucleotides ("ClickTags") are attached to exposed NHS-reactive amines on methanol-fixed cells of interest. ClickTag labeling is achieved in a one-pot, two-step reaction by combining cell samples with methyltetrazine-activated DNA (MTZ-DNA) oligos and the amine-reactive cross-linker NHS-trans-cyclooctene (NHS-TCO) (FIG. 9B). NHS-functionalized oligos are formed in situ via inverse-electron demand Diels-Alder (IEDDA) chemistry, and nucleophilic attack by accessible cellular amines chemoprecipitates the oligos directly onto the cells. Our one-pot reaction based on the IEDDA reaction improves on a previous cell surface modification scheme that requires far higher DNA concentrations and isolation of unstable activated DNAs immediately before use. A library of methyltetrazine-modified ClickTags can be prepared in advance, stored at −20° C. for long periods, and applied to many cell samples in parallel. Sequencing library preparation is derived from published methods for multi-modal scRNA-seq. In brief, the ClickTag sequences contain poly(dA) tails that are captured and copied during reverse transcription, appending the same cell barcodes as the associated mRNAs from the same cell. The resulting short, dsDNAs are isolated during SPRI purification, specifically amplified, and purified by agarose gel electrophoresis.

Oligo Activation

ClickTags were prepared with either 5'- or 3'-amine modified oligonucleotides (100-250 nmol scale, Integrated DNA Technologies, see Table 1). HPLC purification was critical to obtain highly reactive preparations of 5'-modified oligos, while 3'-modified oligos were purchased without HPLC purification. In either case, oligos were resuspended to a concentration of 500 µM in 50 mM sodium borate buffer pH 8.5 (Thermo). NHS esters and MTZ-Cy5 were resuspended in dry DMSO and stored in single-use aliquots at −80° C. at the following concentrations: NHS-TCO 20 mM; NHS-MTZ 10 mM; MTZ-Cy5 1 mM, TCO-Cy5 1 mM. For NHS-TCO and modified fluorophores, dilution in DMSO is performed immediately before use.

Oligo activation reactions were performed by combining 25 µL oligo solution with 41.8 µL DMSO (Sigma) and 8.2 µL of 10 mM NHS-methyltetrazine (Click Chemistry Tools). The reaction was allowed to proceed for 30 minutes at room temperature on a rotating platform. After 30 and 60 minutes, additional 8.2 µL aliquots of 10 mM NHS-methyltetrazine were added. After 90 minutes total reaction time, ethanol precipitation was performed by addition of 180 µL 50 mM sodium borate buffer and 30 µL 3 M NaCl. After mixing, 750 µL ice-cold ethanol was added and the mixture precipitated at −80° C. overnight. The precipitate was pelleted at 20,000×g for 30 minutes at 4° C., washed twice with 1 mL ice-cold 70% ethanol, then resuspended in 100 µL 10 mM HEPES pH 7.2. Yield was determined by absorbance at 260 nm. Typical final concentrations ranged between 40 and 80 µm.

Figure 10A:
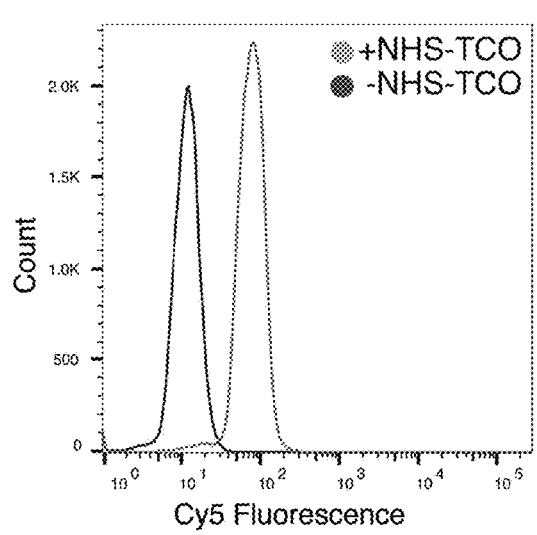
FIGS. 10A-10C depict data related to direct labeling with Inverse Electron-Demand Diels-Alder (IEDDA) chemistry.
Figure 10B:
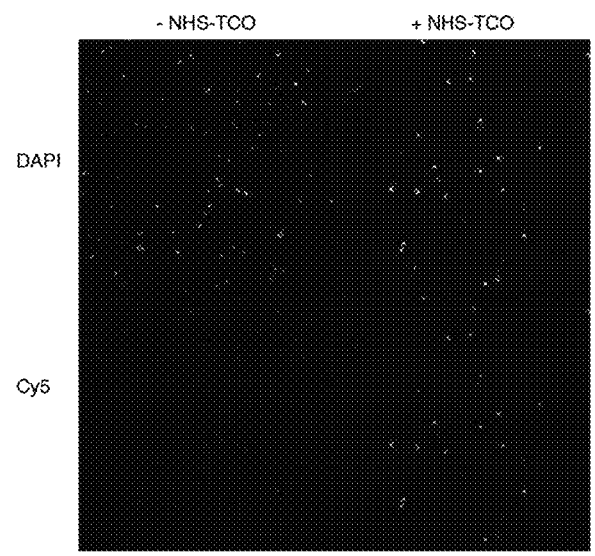
Figure 10C:
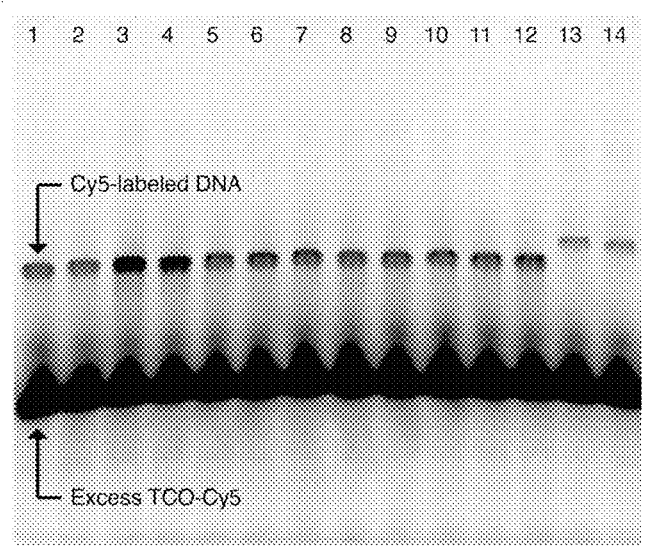

Relative oligo activity was determined by electrophoretic mobility shift assay using Cy5-trans-cyclooctene (Click Chemistry Tools). Methyltetrazine-derivatized oligos were diluted 100-fold in 10 mM HEPES pH 7.2, then 4 µL of this solution was added to 1 µL of a 500 nM solution of TCO-Cy5 in DMSO. All tetrazine reactions in this work were performed in the dark to protect the photoreactive trans-cyclooctene group. The reaction was allowed to proceed at room temperature for 20-120 minutes and analyzed on a 12% SDS-PAGE gel. Oligo activity varied within a 2-fold range across preparations. Oligos were stored at −20° C. and used without further normalization. Electrophoretic activity assay and confirmation of cell labeling by microscopy, as demonstrated in FIG. 10, are strongly recommended for new users. MTZ-DNAs can be stored for months without loss of activity, but use of oligos with more than 2-fold difference in concentration or activity may reduce cell labeling performance across samples, and the activity of separate batches should be compared before being used together.

Cell Culture and Fixation

Neural stem cells were cultured according to the following protocol:

Cryopreserved mouse neural stem cells (NSCs) were thawed for 2 minutes at 37° C. then transferred to a 15 mL conical tube. Pre-warmed Neural Stem Cell Basal Medium (SCM003, Millipore) was slowly added to a total volume of 10 mL, and the resulting cell suspension centrifuged at room temperature for 2.5 minutes at 200×g. The supernatant was removed and the cell pellet was resuspended in 2 mL pre-warmed Neural Stem Cell Basal Medium and counted on the Countess II Automated Cell Counter (Thermo). Cells were seeded on poly-L-ornithine (Millipore) and laminin (Thermo) coated 100 mm culture plates at 700,000 cells per plate in 10 mL of pre-warmed Neural Stem Cell Basal Medium supplemented with EGF (Millipore) and bFGF (Millipore) at 20 ng/mL each, heparin (Sigma) at 2 µg/mL, and 1% Penicillin-Streptomycin (Thermo). Supplemented medium was changed the next day and every other day thereafter until confluent.

Neural stem cells for 96-sample growth factor screen were cultured according to the following protocol after the above described cell culture plate reached ~80% confluence: Stock solutions (10×) were prepared in Neural Stem Cell Basal Medium for every factor and at every concentration used: [EGF+bFGF at 200 ng/mL, 40 ng/mL, 8 ng/mL, 1.6 ng/mL]; [BMP4 (Peprotech) at 200 ng/mL, 40 ng/mL, 8 ng/mL, 0 ng/mL]; [Retinoic Acid (Sigma) at 10 µM, 2 µM, 0 µM]; [Scriptaid (Selleckchem)/Decitabine (Selleckchem) at 1 µM/5 µM, 0.2 µM/1 µM, 0 µM/0 µM]; [Heparin at 20 m/mL+Penicillin-Streptomycin at 10%]. 20 µL of each stock (EGF/bFGF; BMP4; Retinoic acid or Scriptaid/Decitabine; and Heparin/Penicillin-Streptomycin) were added to each well of a poly-L-ornithine and laminin coated 96-well plate for a total of 80 µL.

NSCs previously plated on 100 mm culture plates until ~80% confluent were dissociated by incubation in 4 mL of ESGRO Complete Accutase (Millipore) for 2 minutes at 37° C. After incubation, the Accutase and NSCs were transferred to a 15 mL conical tube and centrifuged at room temperature for 2.5 minutes at 200×g. Supernatant was removed and the cell pellet was resuspended in 2 mL Neural Stem Cell Basal Medium. Centrifugation and medium replacement were repeated once more and cell concentration was counted on the Countess II Automated Cell Counter. The cell suspension was then diluted with additional Neural Stem Cell Basal Medium to a concentration of 18.3 cells/µL. From this stock 120 µL was added to each well of the 96-well plate for a total of ~2,200 cells/well. Supplemented media for every well in the 96-well plate was replaced every other day during the 5-day incubation.

Before NSC dissociation and fixation, 80 µL of ice-cold methanol was added to each well of twelve 8-well PCR strips on an ice block. After 5 days in culture, all media in the 96-well plate was removed and the cells washed three times with 150 µL of Neural Stem Cell Basal Medium. Any remaining media were removed and replaced with 20 µL of Accutase and incubated at 37° C. for 2 minutes with gentle pipetting to help break cell clumps. Next, 20 µL of dissociated NSCs in Accutase were transferred to the 8-well strip tubes containing 80 µL of 100% methanol, and the entire volume was pipetted to mix. After fixation, the NSCs were stored at −20° C. until sample labeling.

For four-sample NSC labeling and species-mixing experiments (below), NSCs were cultured on a 100 mm poly-L-ornithine and laminin coated culture plate according to the protocol previously described until ~80% confluent. NSCs were dissociated by removing culture medium followed by incubation with 4 mL Accutase for 2 minutes. NSCs in Accutase were transferred to a 15 mL conical tube and centrifuged at room temperature for 2.5 minutes at 200×g. The supernatant was removed and the cell pellet was resuspended in 2 mL Hank's Balanced Salt Solution (HBSS, Thermo) with 0.04% BSA (Sigma). Centrifugation and medium replacement were repeated once and cell concentration was determined on a Countess II Automated Cell Counter. Cells were then fixed by addition of 4 volumes ice-cold methanol added slowly with constant mixing. Fixed cells were stored at −20° C. until ClickTag labeling and scRNA-seq.

Frozen stocks of HEK293T cells (ATCC) were thawed for 2 minutes at 37° C. with gentle agitation. Thawed cells (500 µL) were added to 5 mL pre-warmed media (DMEM (Corning)+10% FBS (Gemini Bio-Products)+1% Penicillin-Streptomycin (Corning) and centrifuged at 1,500×g for 5 minutes. The cells were resuspended in 5 mL media and transferred to a T-25 cell culture flask. Cells were grown at 37° C. with 5% CO2 following standard practices. HEK293T cells were dissociated by incubation with TrypLE Select (Thermo) for 5 minutes at 37° C., washed twice with HBSS, and resuspended in 1 mL at a concentration of ~6×10$^6$ cells/mL. Cell number and viability were measured using a Countess II Automated Cell Counter. Four mL ice-cold methanol was added slowly with constant mixing, and the resulting cell suspension incubated at −20° C. for at least 20 minutes. Cells were stored at −20° C. until ClickTag labeling and scRNA-seq.

Flow Cytometry and Fluorescence Microscopy

Yeast cells (Fleischmann's Rapid Rise) were used as an abundant cellular substrate to test cell labeling reactions. Approximately 5 g of dehydrated cells were rehydrated in 4 mL PBS+0.1% Tween-20 (Sigma) for 10 minutes at room temperature with rotation. One mL of the resulting cell suspension was diluted with 7 mL PBS-Tween and fixed by slow addition of 32 mL ice-cold methanol with constant mixing. Cells were incubated at −20° C. for at least 20 minutes before further use.

Methanol-fixed cells were rehydrated by combining 700 µL HBSS with 500 µL fixed cells in 80% methanol. This suspension was centrifuged at 3,000×g for 5 minutes, then washed twice more with HBSS. Cells were resuspended in 1 mL HBSS, and 50 µL of this cell suspension was used for cell labeling. Methyltetrazine-Cy5 (Click Chemistry Tools) was added to 2 µM final concentration, NHS-TCO to 5 µM, and DAPI to 1 µg/mL. Cell labeling reactions were incubated for 30 minutes at room temperature with rotation then quenched by addition of Tris-HCl to 10 mM and methyltetrazine-DBCO (Click Chemistry Tools) to 50 µM. Samples were diluted 20-fold in HBSS and analyzed on a MACSQuant VYB flow cytometer.

Fluorescence microscopy samples were prepared as above except NHS-TCO was used at 1 µM and MTZ-Cy5 was used at 62.5 µM. Samples were imaged on a Zeiss LSM 800 laser scanning confocal microscope.

Multiplexed scRNA-Seq Proof of Concept

Fixed NSCs were split into four aliquots with ~400,000 cells in 100 µL 80% methanol. Live NSCs were prepared as described above, washed into HBSS, and similarly aliquoted to four samples with 400,000 cells in 100 µL. Prior to cell labeling, 8 labeling combinations were made by combing 6 µL each of two different MTZ-derivatized ClickTags. A 5-minute pre-incubation reaction was performed in the dark at room temperature by addition of 4 µL 1 mM NHS-TCO. After pre-incubation, cell suspensions were thoroughly mixed with the entire volume of a single ClickTag labeling mix. Cell labeling proceeded for 30 minutes at room temperature on a rotating platform. Reactions were quenched by addition of Tris-HCl to 10 mM final concentration and methyltetrazine-DBCO (Click Chemistry Tools) to 50 µM final concentration. After quenching for 5 minutes, cells were pooled to create a single sample for fixed cells and a single sample for live cells. Two volumes PBS-BSA was added and the cells pelleted by centrifugation at 500×g for 5 minutes. Cells were washed three times with PBS-BSA and vigorously resuspended in a final volume of 150 µL. Cells were analyzed, counted, and loaded on two lanes of the Chromium Controller (10× Genomics, Inc.) targeting 5,000 cells each. Library preparation was adapted from the REAP-Seq protocol. The 10× Genomics v2 Single Cell 3' seq Reagent kit protocol (10× Genomics) was used to process samples according to the manufacturer's procedure with modifications as follows: After initial amplification of cDNA and ClickTags, the two libraries were separated during SPRI size-selection. The manufacturer's instructions were used to complete full-length cDNA library preparation. For ClickTags, rather than discarding the 0.6×SPRI supernatant, this fraction was combined with more SPRI beads (final SPRI ratio 1.5×) and incubated at room temperature for 5 min. The SPRI beads were washed twice with 80% EtOH and ClickTags eluted in 20 µL nuclease-free water. ClickTags were quantified by Qubit High-Sensitivity DNA Assay (Invitrogen) and amplified using primer R1-P5 and indexed reverse primers as appropriate (see Table 4). Table 4 depicts run statistics for multiplexed, fixed, and live mouse NSCs described in FIG. 15.

TABLE 4

RUN STATISTICS FOR MULTIPLEXED, FIXED, AND LIVE MOUSE NSCS

| Metric | Multiplexed* | Fixed | Live |
| --- | --- | --- | --- |
| Number of Cells | 4,611 | 3,808 | 9,719 |
| Number of Reads | 200M | 255M | 222M |
| Mean Reads per Cell | 26,022 | 67,059 | 22,803 |
| Reads Mapped to Transcriptome | 79.0% | 77.0% | 66.7% |
| Fraction Reads in Cells | 90.6% | 92.8% | 92.6% |
| Sequencing Saturation | 60.1% | 79.8% | 42.0% |
| Median Genes per Cell | 2,090 | 2,241 | 2,169 |

The multiplexed sample contained both mouse and human cells, so the multiplexed statistics correspond only to "mouse" cells as identified by CellRanger. Note that the "Fixed" sample was sequenced much more deeply than the "Multiplexed" and "Live" samples. PCR was performed in a 25 µL volume including 2.5 µL ClickTag library, 1.5 uL of 10 uM forward, 1.5 uL of 10 uM reverse primer, 7 µL nuclease-free water, and 12.5 µL KAPA 2×HIFI PCR master mix (Kapa Biosystems). The samples were cycled as follows: 98° C. 3 min, 16 cycles of: 98° C. 20 sec, 58° C. 30 sec, and 72° C. 20 sec; and then a final extension step of 72° C. for 4 min. Final ClickTag libraries were obtained using a PippinPrep automated size selection system with a 3% agarose gel set for a broad purification range from 200-250 bp (target library size is 225 bp). A Qubit assay was again used to determine library concentration for sequencing. ClickTag and cDNA libraries were analyzed on a BioAnalyzer High Sensitivity DNA kit (Agilent). Example traces are provided for reference (FIG. 6). ClickTag libraries were sequenced on an Illumina MiSeq using a MiSeq V3 150 cycle kit (26×98 bp reads), and cDNA libraries were not sequenced for this proof-of-concept experiment.

Species Mixing and ClickTag Multiplexing

Methanol-fixed human HEK293T and mouse NSCs were prepared as described above. Samples were labeled with non-overlapping ClickTag sets of increasing size (Table 3). Suspensions of both cell types were prepared at 700,000 cells/mL in 80% methanol. Samples of 100 uL were prepared for each condition, with species mixing conditions comprising 50 µL of cell suspension from each species. For this experiment, 3'-modified oligos isolated by standard desalting were used as opposed to the 5'-modified, HPLC-purified oligos used in all other experiments presented. ClickTag sets were prepared by reacting 6 µL of each oligo along with 2 µL of 1 mM NHS-TCO per oligo at room temperature. After 5 minutes, the entire volume of each labeling mixture was added to the appropriate cell suspension. Cell labeling was performed for 30 minutes at room temperature on a rotating platform. Reactions were quenched as above, pooled, and added to 2 mL PBS+1% BSA. Samples were split across two Eppendorf tubes and centrifuged at 500×g for 5 minutes. Cell pellets were resuspended in 500 µL PBS-BSA, combined, and centrifuged once more. The cell pellet was washed twice more with 1 mL PBS-BSA. Finally, the cells were resuspended in 150 µL PBS-BSA, counted, diluted to 1×10$^6$ cells/mL and loaded on a single lane of the Chromium Controller targeting 10,000 cells. ClickTag and cDNA libraries were prepared as described. Libraries were submitted for sequencing as part of an Illumina NovaSeq library, targeting 500 M reads total (2×150 bp reads), with ClickTags submitted at 10% of the total library concentration.

96-Sample Growth Factor Screen

Figure 23A:
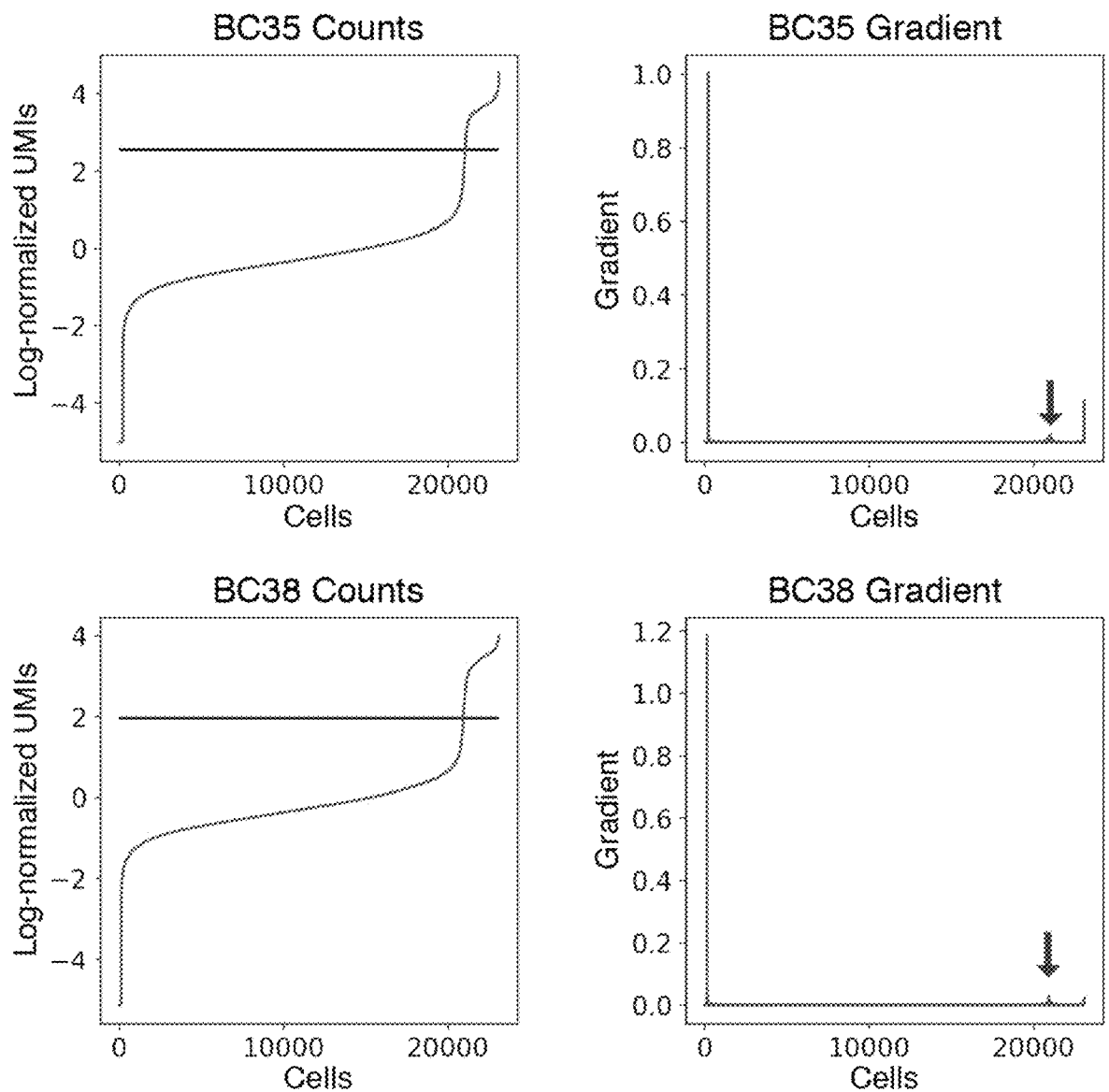
Figure 23B:
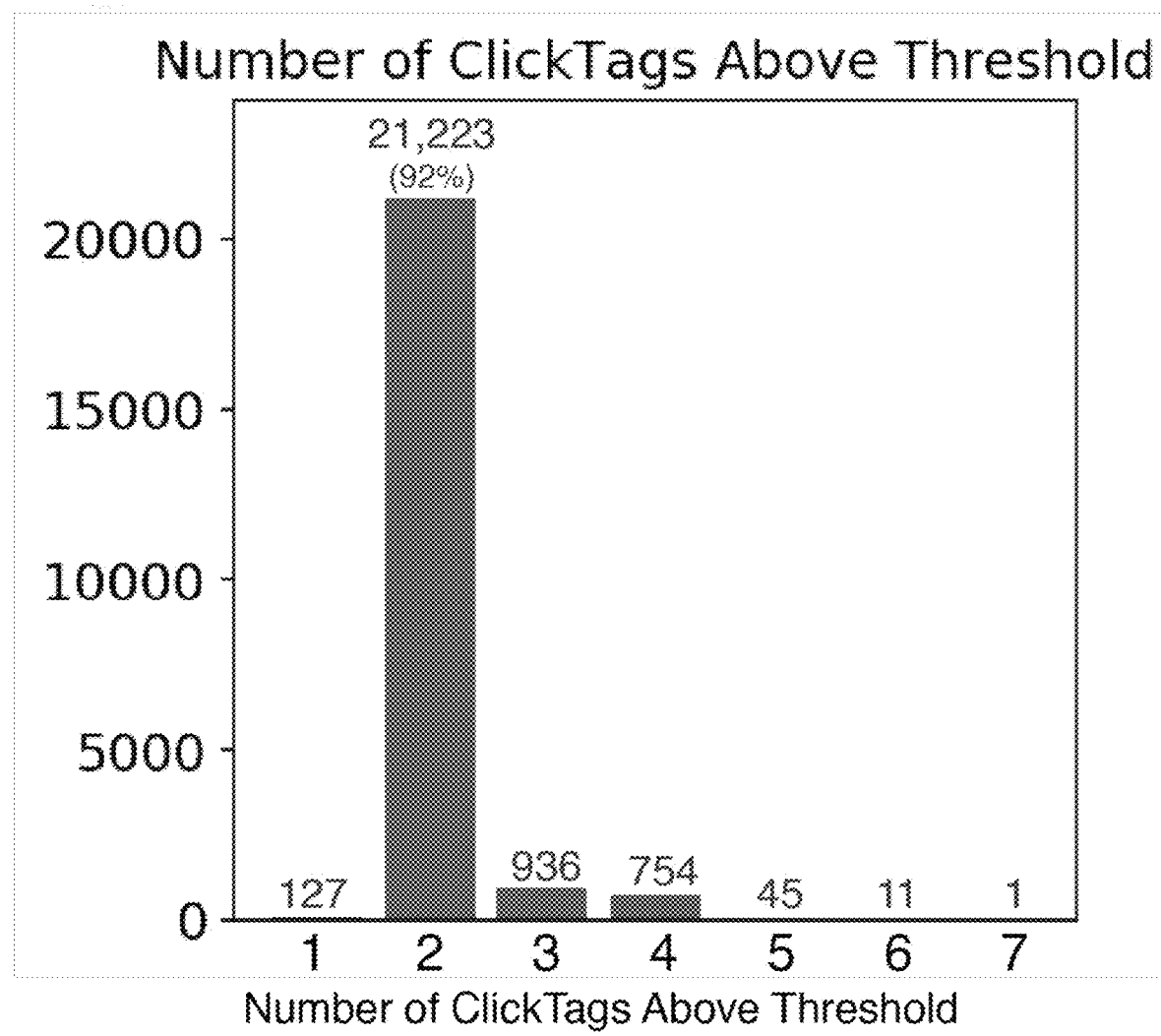
Figure 23C:
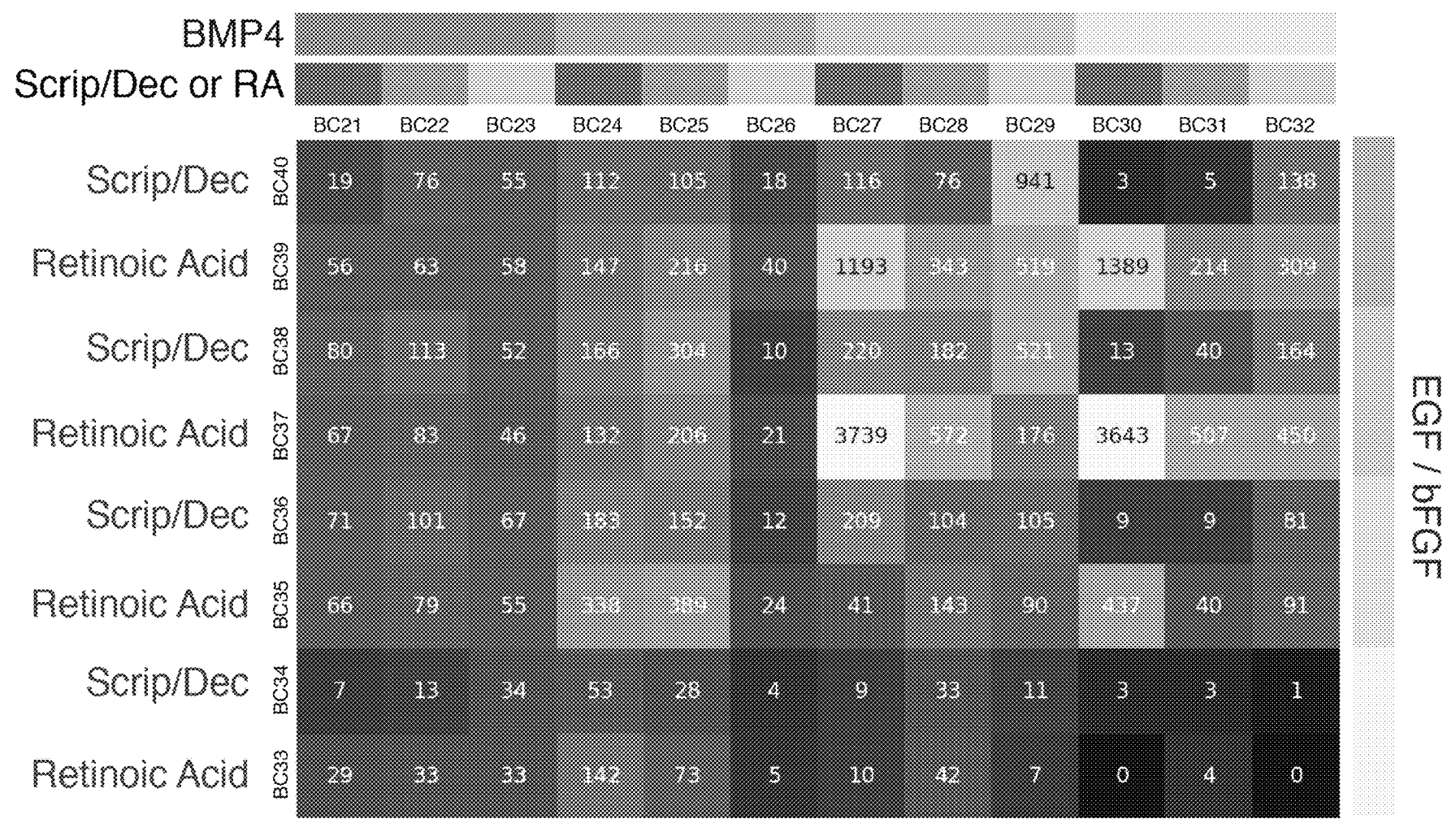

NSCs for the 96-sample perturbation experiment were prepared as described above. For each sample, two Click-Tags (6 µL each) were combined with 4 uL 1 mM NHS-TCO according an 8×12 matrix. Columns 1-12 of the 96-well plate correspond to ClickTags BC21-BC32, while rows A-H correspond to ClickTags BC33-BC40 (FIG. 23). Fixed cells from each experimental condition (100 µL) were labeled with the entire volume of the corresponding ClickTag mix for 30 minutes at room temperature on a rotating platform. Samples were quenched as described above, pooled, and combined with 15 mL PBS-BSA. Samples were split across two 15-mL conical tubes and spun at 500×g for 5 minutes. Cell pellets were resuspended in 3 mL PBS-BSA each and centrifuged again. The pellets were washed twice with one mL PBS-BSA and resuspended in a final combined volume of 200 uL. Cells were loaded on two lanes of the 10×Chromium Controller targeting 10,000 cells per lane. Sequencing libraries were prepared as two large libraries (9,000 cells each) and two small libraries (1,000 cells each). ClickTag amplicons were sequenced on two lanes of Illumina MiSeq using MiSeq v3 150 cycle kits (26×98 bp reads), and cDNA libraries were pooled and sequenced on Illumina HiSeq 4000 using two HiSeq 3000/4000 SBS 300 cycle kits (2×150 bp reads).

cDNA Data Processing

Raw sequenced reads were processed using the 10× Genomics Cell Ranger pipeline (version 3.0.0). The 'cell-ranger mkfastq' command was used to demultiplex libraries based on sample indices and to convert the barcode and read data to FASTQ format files. The 'cellranger count' command was used to identify cell barcodes and to align reads to the mouse or human transcriptomes (mm10 and hg19) as appropriate. For the 96-sample perturbation experiment, the 'cellranger aggr' command was used to combine and normalize sequencing data from the two 10× lanes split across two HiSeq lanes. Cells were selected by Cell Ranger using the inflection point of the rank-UMI vs cell barcodes plot.

ClickTag Data Processing, Assignment, and Doublet Detection

Figure 11:
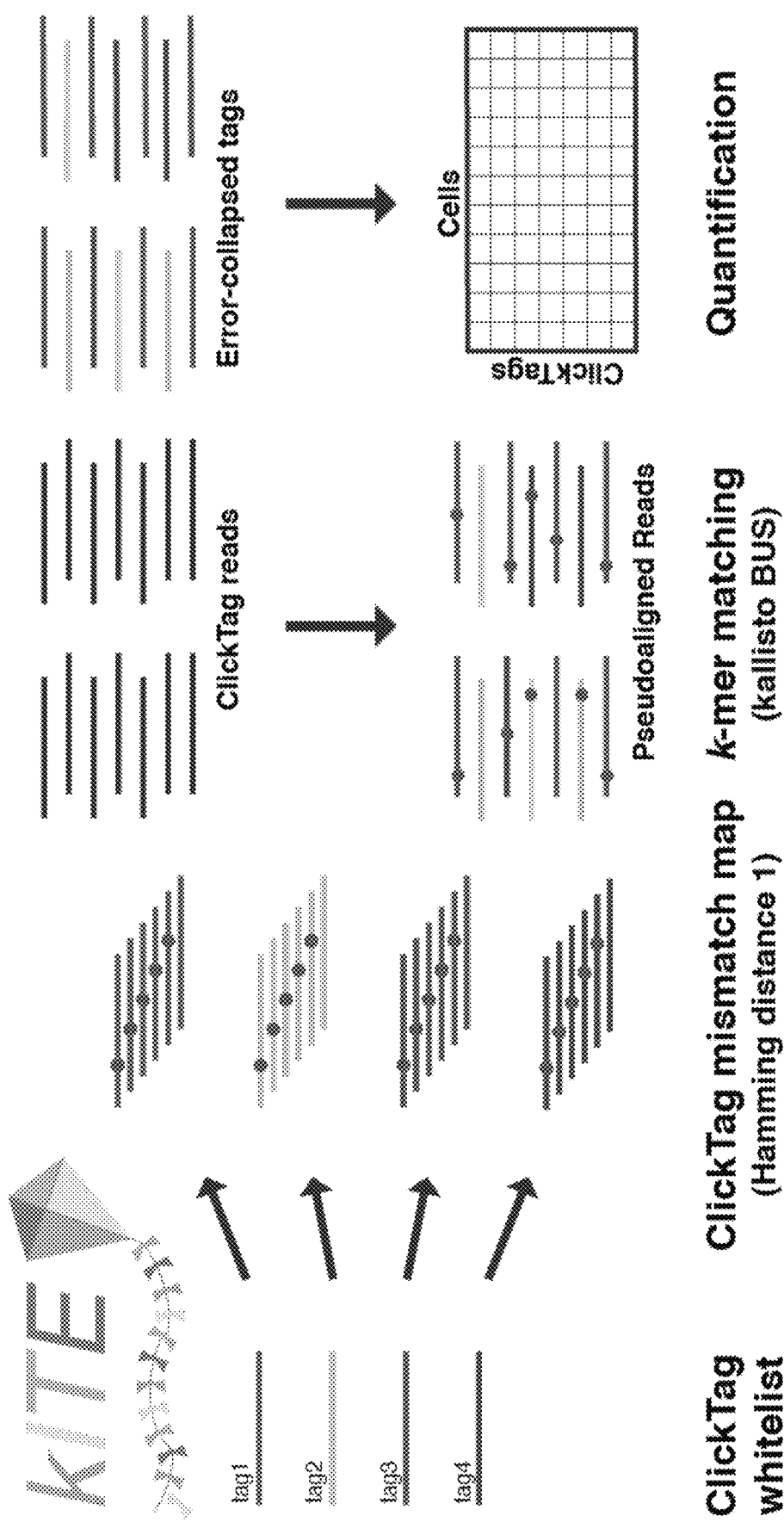
FIG. 11 depicts an overview of the kITE (kallisto Indexing and Tag Extraction) workflow. In kITE, the kallisto RNA-seq pseudoalignment algorithm is used for fast matching of sequencing reads to ClickTag barcodes. To account for the occurrence of errors in sequencing data, a whitelist of ClickTag barcode sequences is converted to a mismatch map containing the correct barcodes as well as all of their Hamming distance 1 variations. The mismatch map is used to create a kallisto index, and 'kallisto bus' commands are run without modification, producing a BUS file where each record contains a unique 10× cell barcode/UMI combination and the identity of the matched sequence. Finally, the mismatch map is used to collapse the BUS file into a ClickTags×Cells matrix which can be analyzed with standard scRNA-seq software.
Figure 12A:
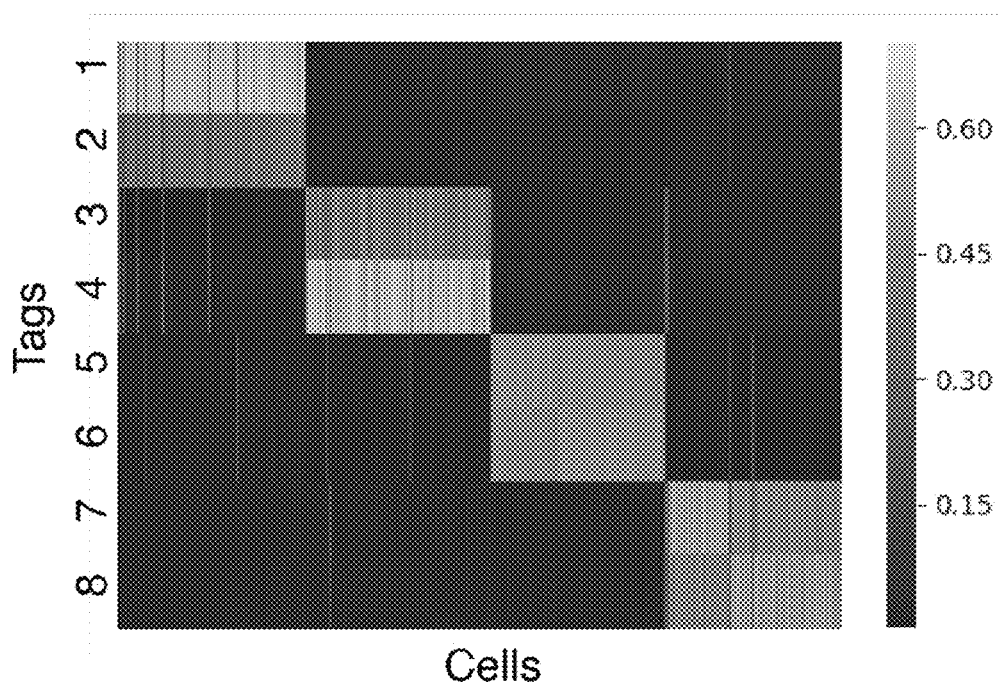
Figure 12B:
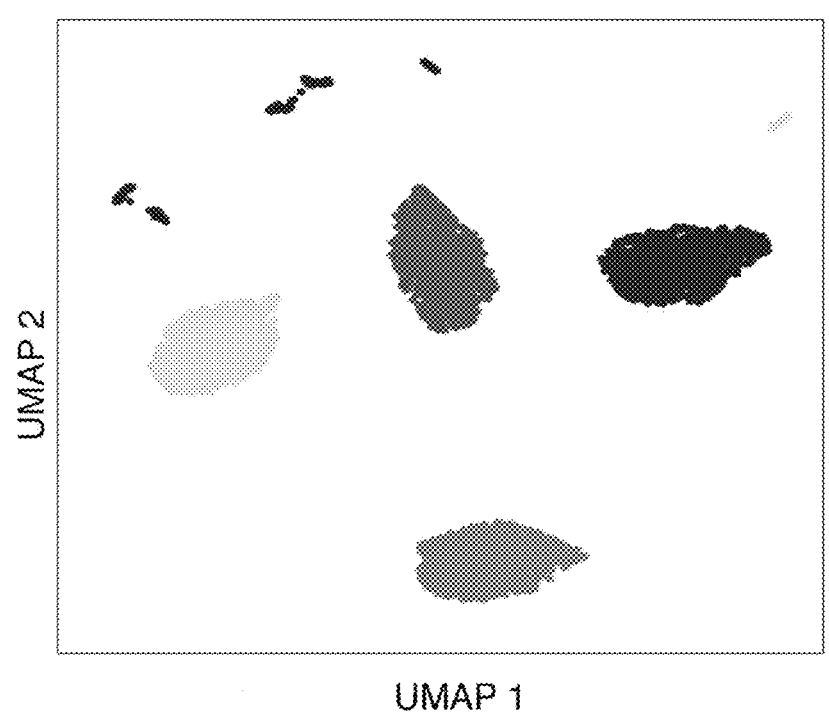
Figure 12F:
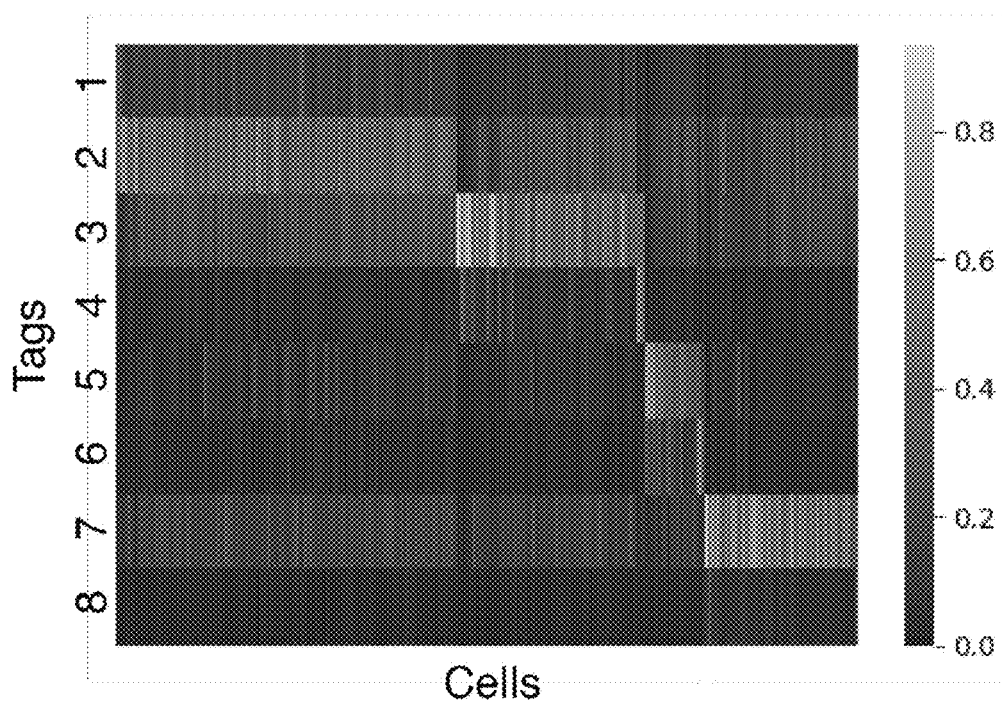
Figure 12G:
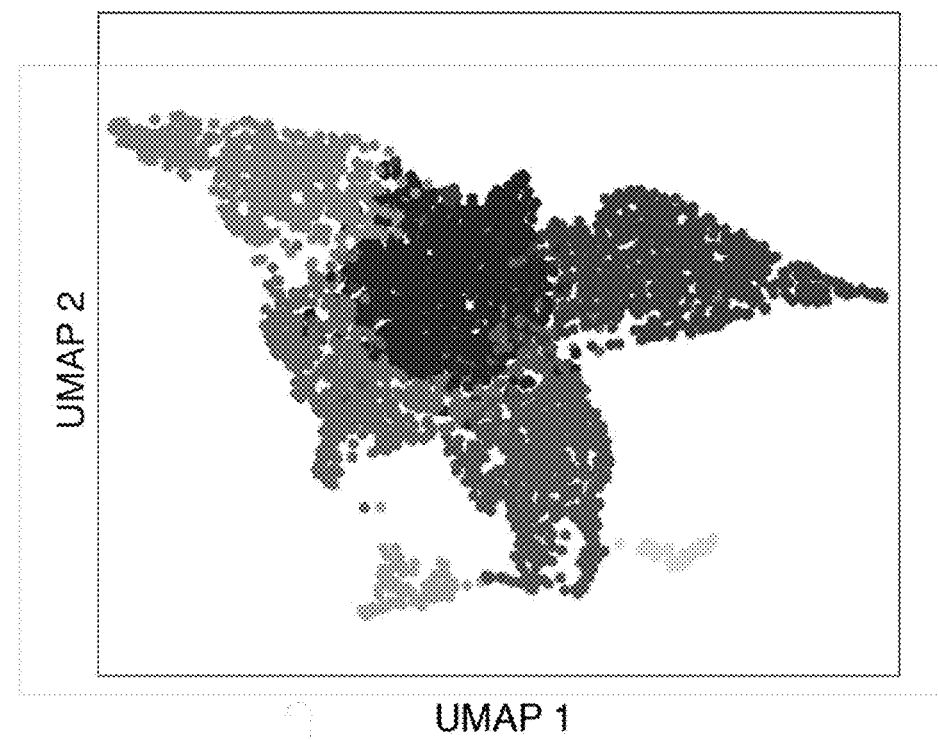
Figure 13A:
Figure 13B:
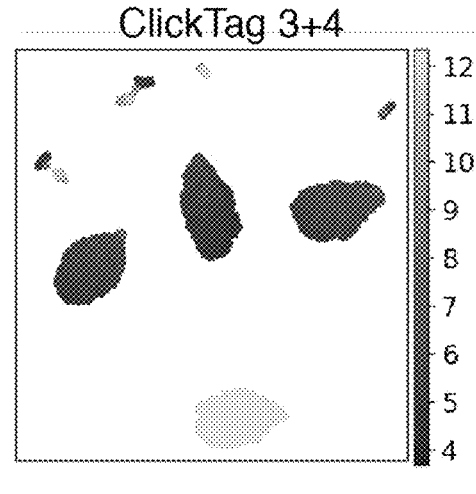
Figure 13C:
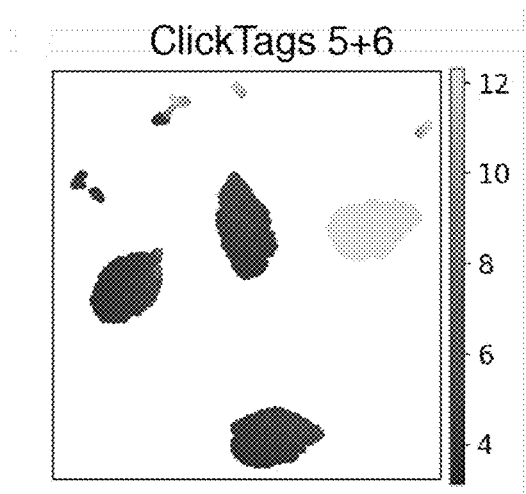
Figure 13D:
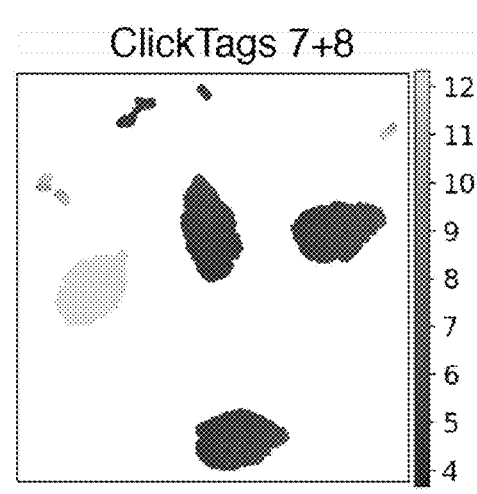
Figure 13E:
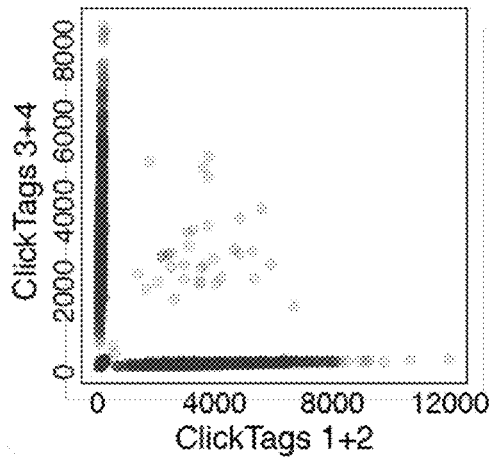
Figure 13F:
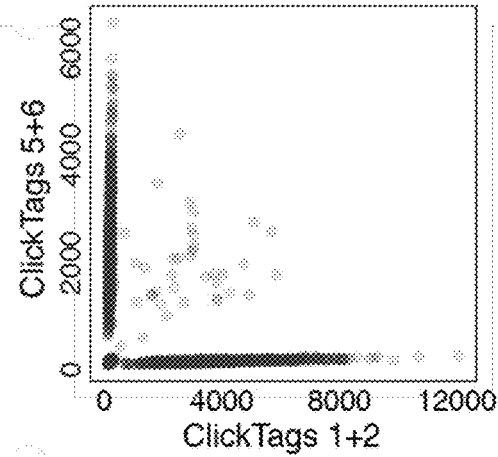
Figure 13G:
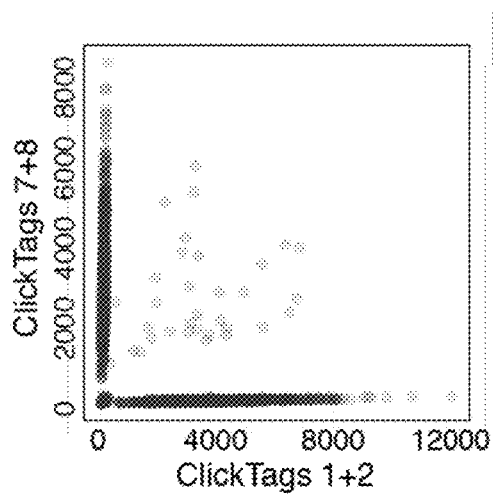
Figure 13H:
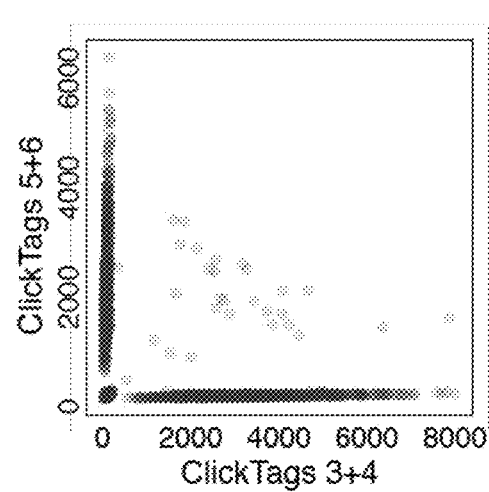
Figure 14A:
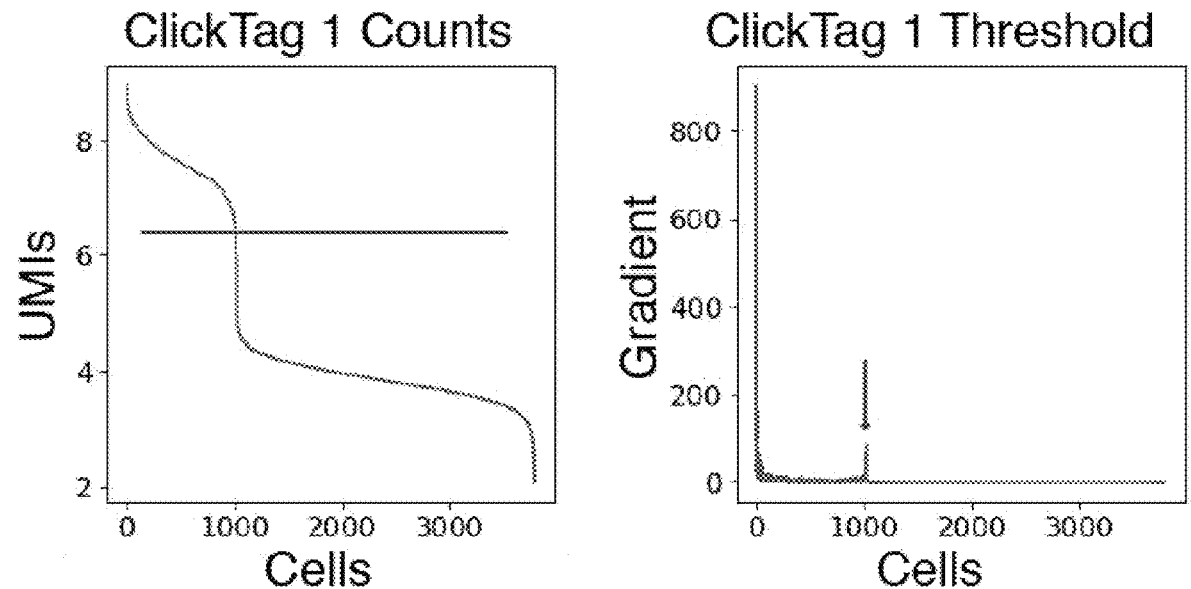
FIGS. 14A-14E depict data related to sample assignment based on ClickTags from four-sample multiplexing experiment shown in FIGS. 12A-12E. Facile thresholding can be achieved by taking the gradient of the rank-UMI plot. Examples are shown for two ClickTags from this experiment (FIGS. 14A-14B). Of 3,800 cells analyzed, 3,627 cells had two ClickTags above threshold, which in all cases corresponded to a pair of sample-specific ClickTags. A doublet rate of ~4.5% is comparable with the doublet rate of ~3% estimated by 10× Genomics.
Figure 14B:
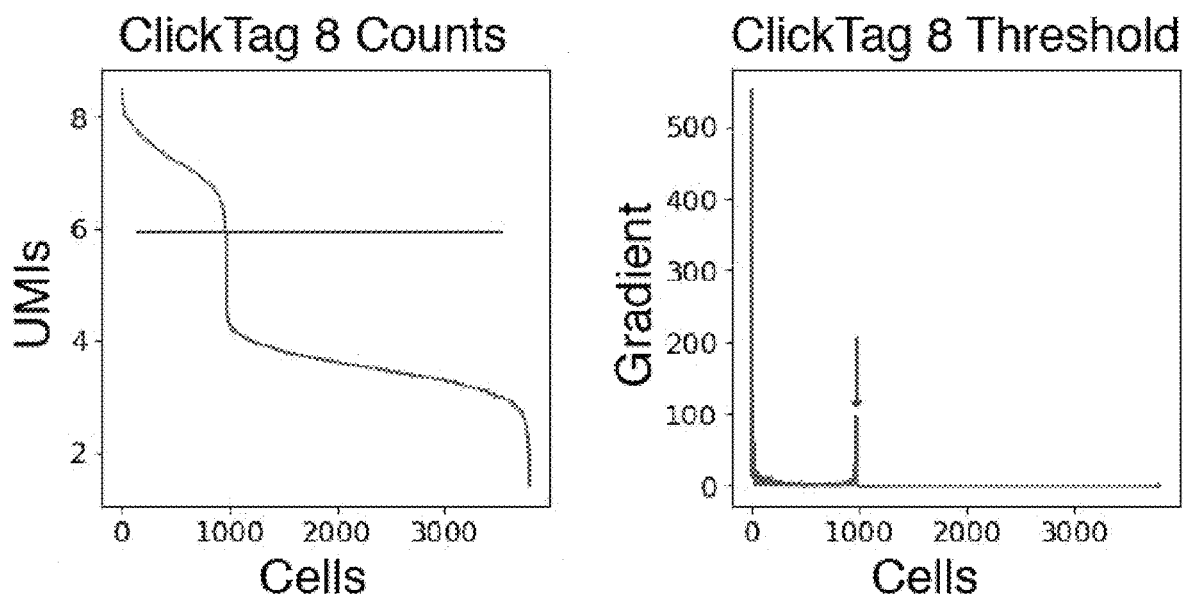
Figure 14C:
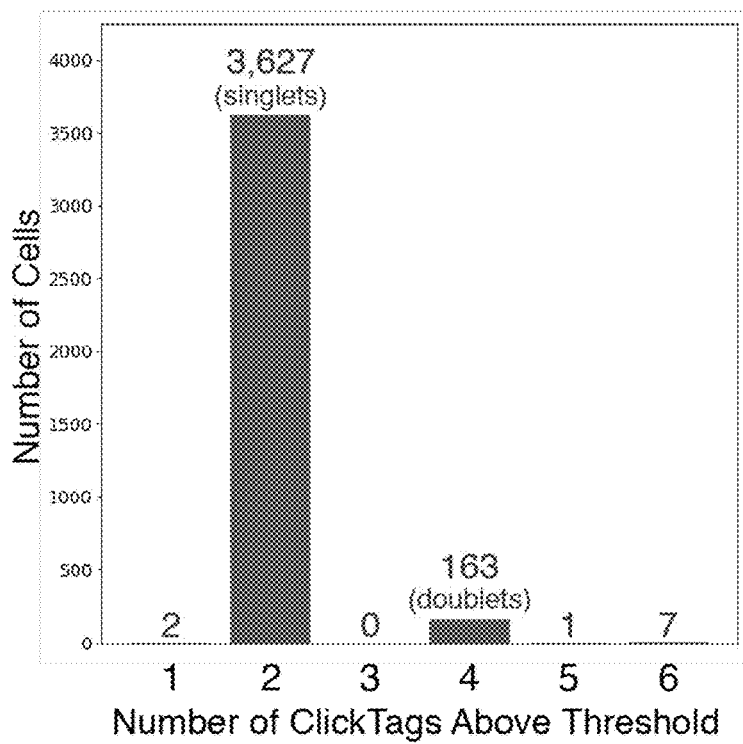
Figure 14D:
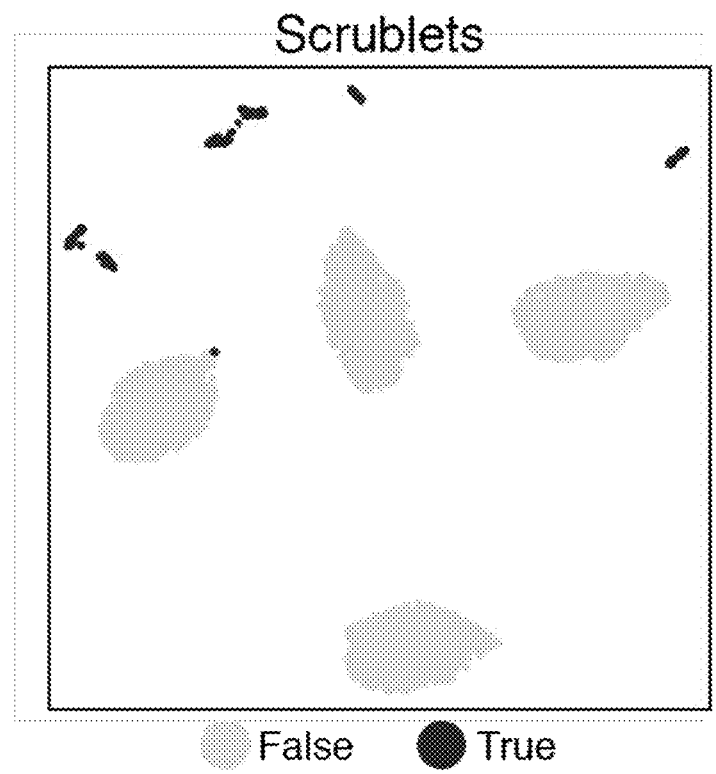
Figure 14E:
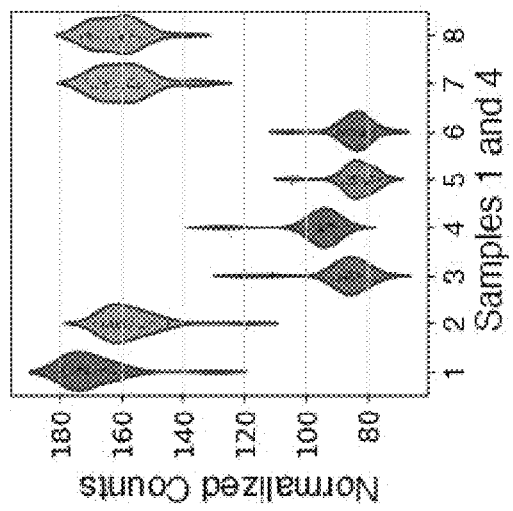
Figure 14E:
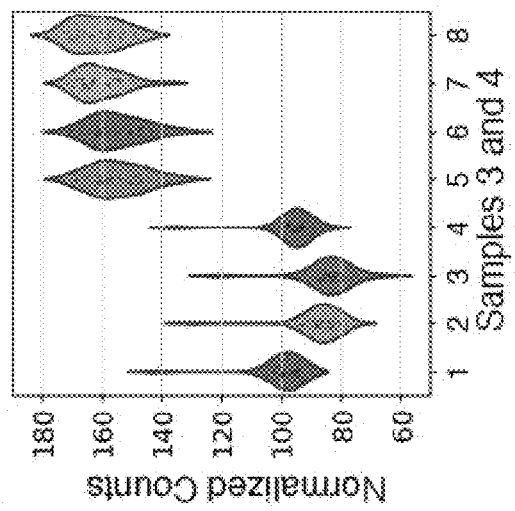
Figure 14E:
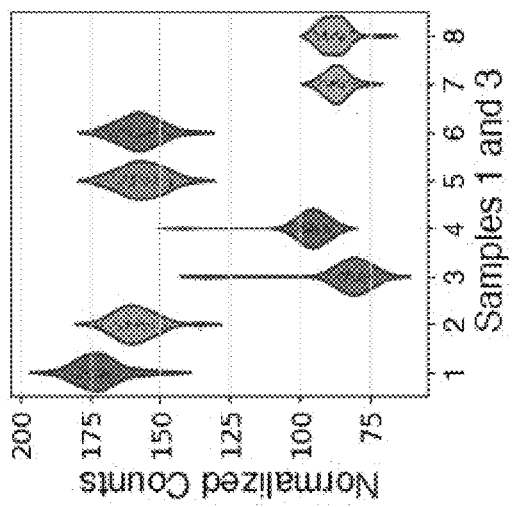
Figure 14E:
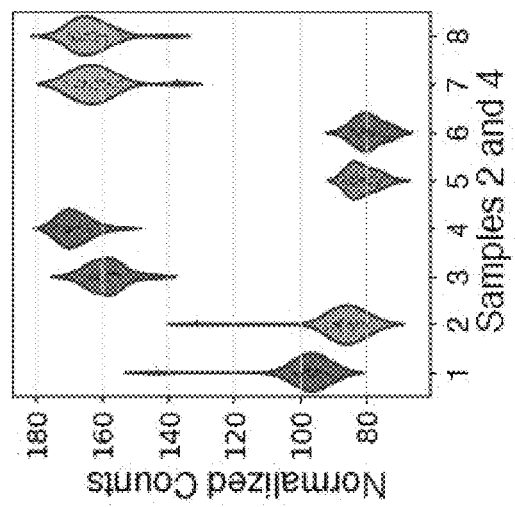
Figure 14E:
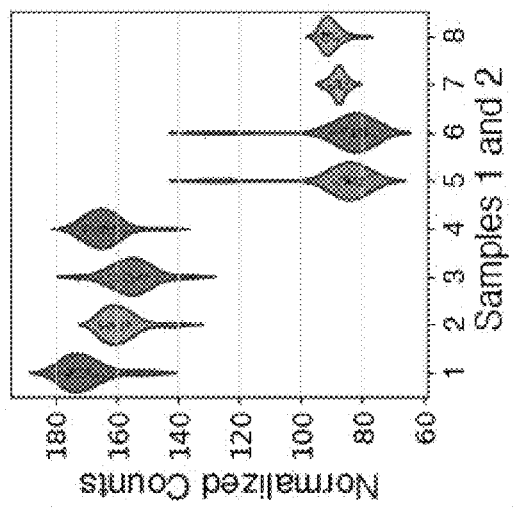
Figure 14E:
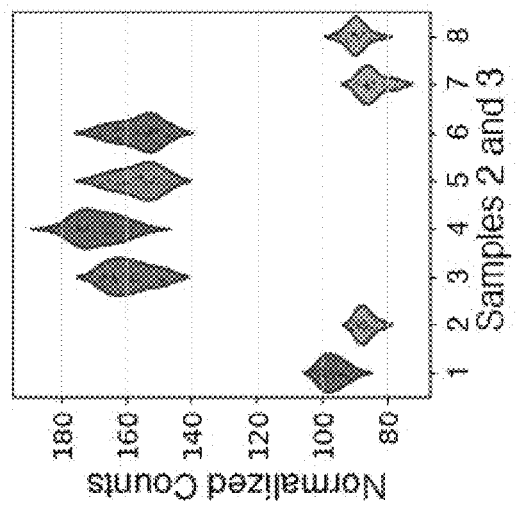
Figure 15A:
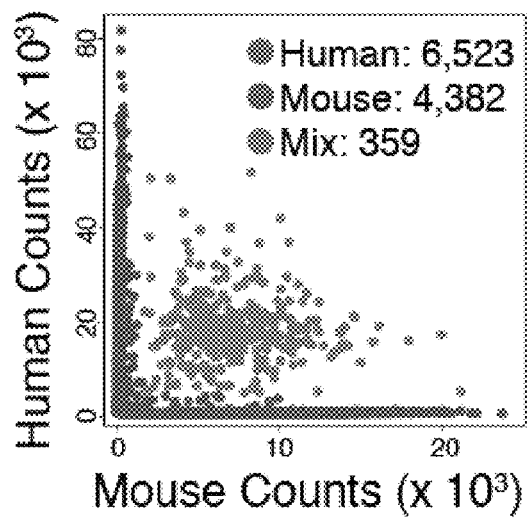
FIGS. 15A-15D depict data related to species-mixing experiment fidelity analysis.
Figure 15B:
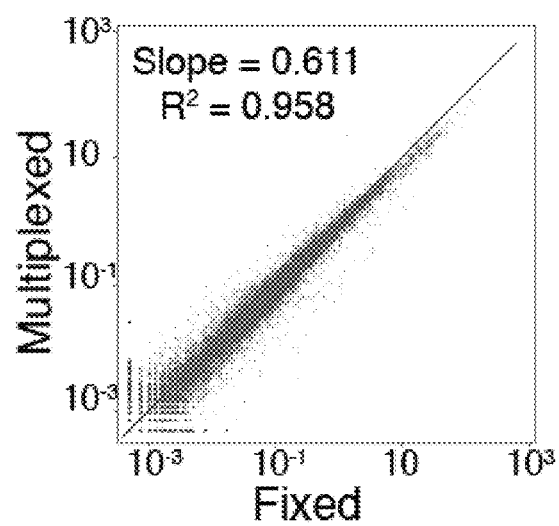
Figure 15C:
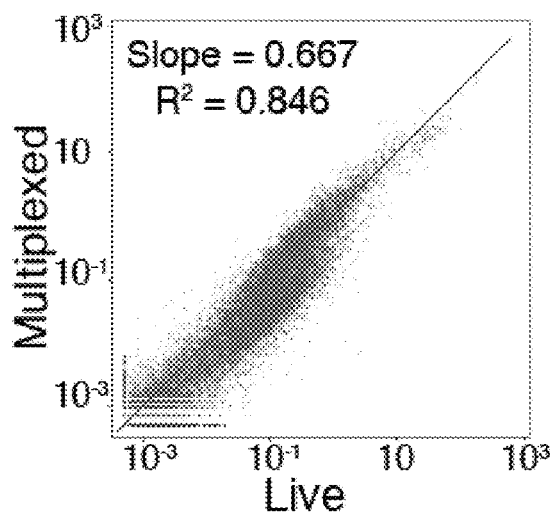
Figure 15D:
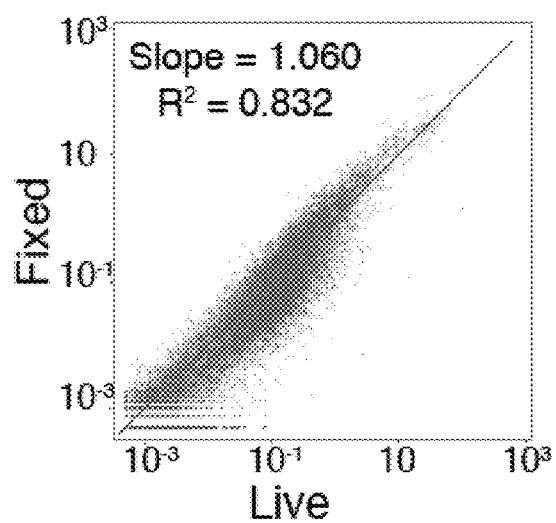

Cell barcode error correction was performed using the 10× barcode whitelist. Subsequently, sequenced reads from the ClickTag libraries were processed with a new feature barcode processing workflow, kITE (kallisto Indexing and Tag Extraction), which is built on the kallito BUS scRNA-seq workflow. In kITE, the ClickTag barcodes used in a given experiment are used to generate a "mismatch index"

consisting of the whitelist feature barcodes and all of their Hamming distance 1 variations (FIG. 11). A kallisto index is produced from the mismatch index, and the 'kallisto bus' command is used to pseudoalign ClickTag reads against the mismatch index. The output is a BUS file entry for every unique feature barcode, UMI, and set combination. Finally, the BUS file is converted to a cells×ClickTags digital count matrix by collapsing counts from each ClickTag feature barcode with those corresponding to its Hamming distance 1 mismatches.

Sample assignment for the four-sample NSC experiments was performed for the top 3,800 cells with the most ClickTag UMIs. For each ClickTag, a threshold was calculated using the numpy gradient function to find the maximum slope of the rank-UMI vs cell barcode plot. The cells× ClickTags matrix was further processed using the ScanPy single-cell analysis package. The data were normalized to 1,000 reads per cell and log-transformed, followed by t-SNE embedding and clustering by Louvain community detection. The Scrublet doublet detection algorithm was used to isolate likely multiplets from the ClickTag data, and this subset of cells was re-clustered to generate the violin plots in FIG. 14.

Figure 25A:
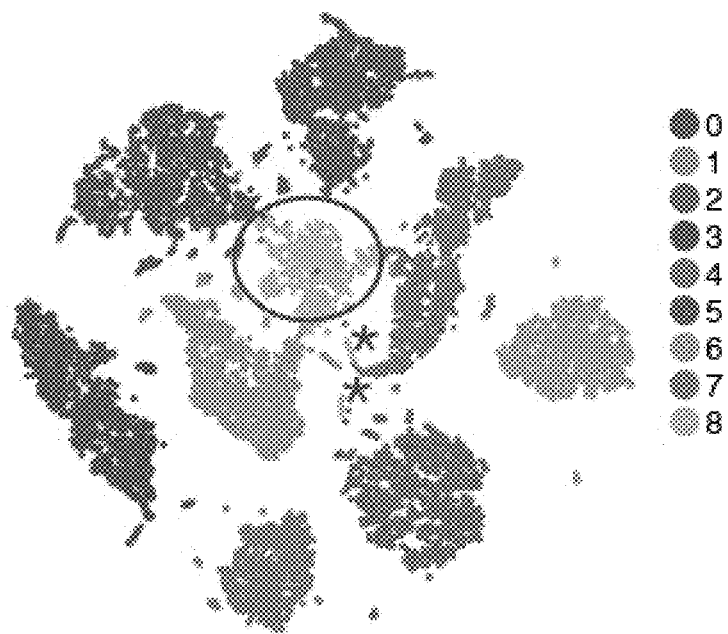
FIGS. 25A-25C depict filtering for high-quality cells in the species-mixing experiment. ClickTag counts from all cells passing the Cell Ranger UMI filter were normalized, log-transformed, and embedded by t-SNE, generating nine distinct clusters. Cluster 8, circled, was found to have reduced UMI counts for both ClickTags and cDNAs and was removed from downstream analysis. Two sub-clusters (*) grouped with Cluster 8 were later found to correspond to two classes of inter-sample doublets and are similarly labeled in FIG. 21 but were not included in the doublet detection comparison shown in FIG. 20.
Figure 25B:
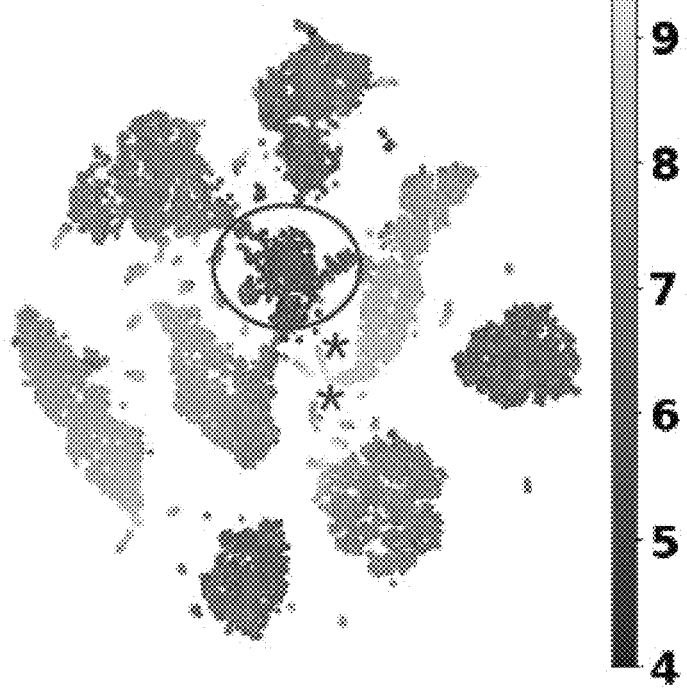
Figure 25C:
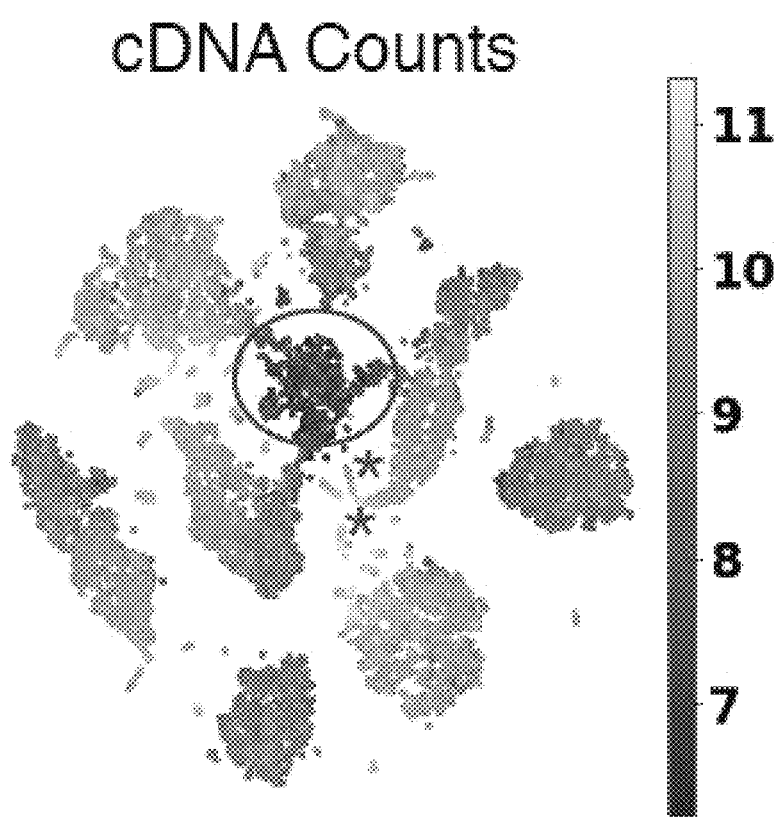
Figure 26A:
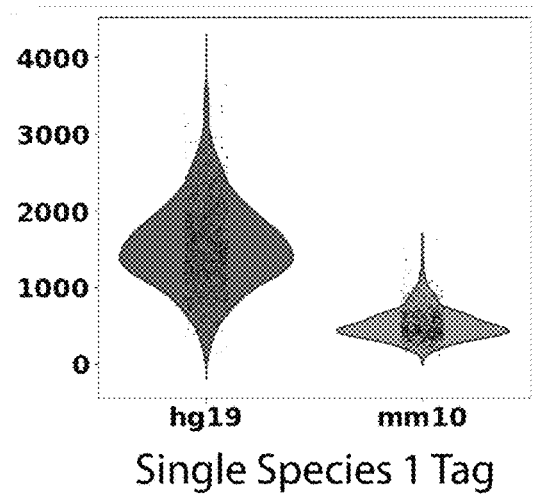
FIGS. 26A-26F depict an analysis of ClickTag counts from human HEK293T and mouse neural stem cells from the multiplexed species-mixing experiment. Human cells consistently yield more ClickTags than mouse cells from the same or similarly treated samples, consistent with the RNA yield as shown in FIG. 22.
Figure 26B:
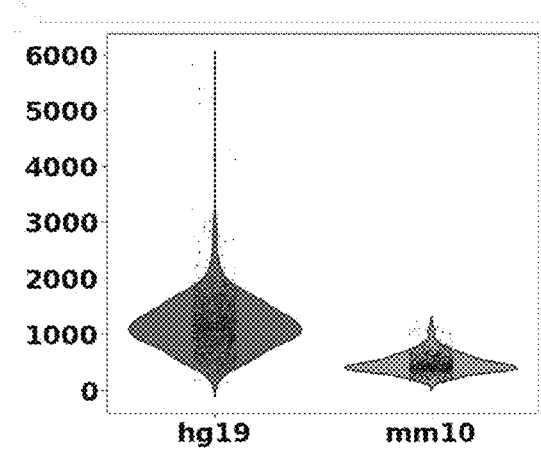
Figure 26C:
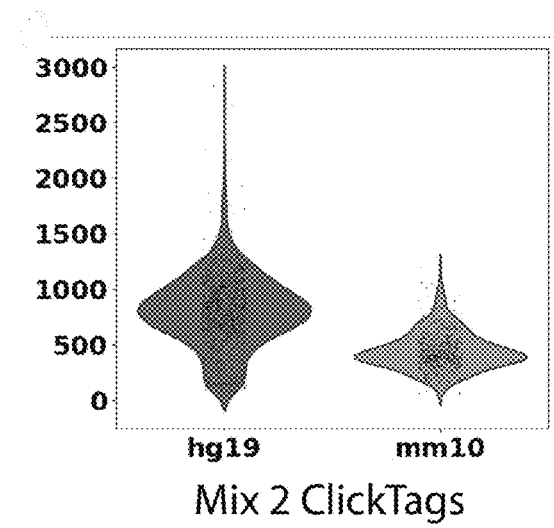
Figure 26D:
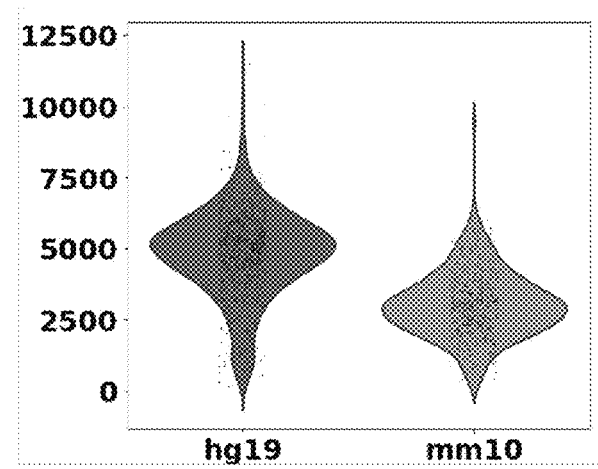
Figure 26E:
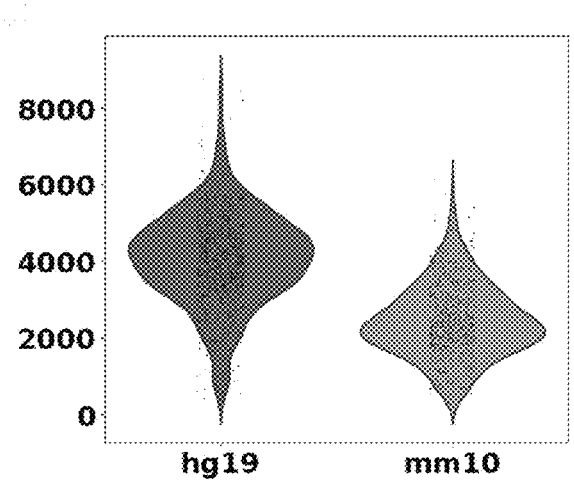
Figure 26F:
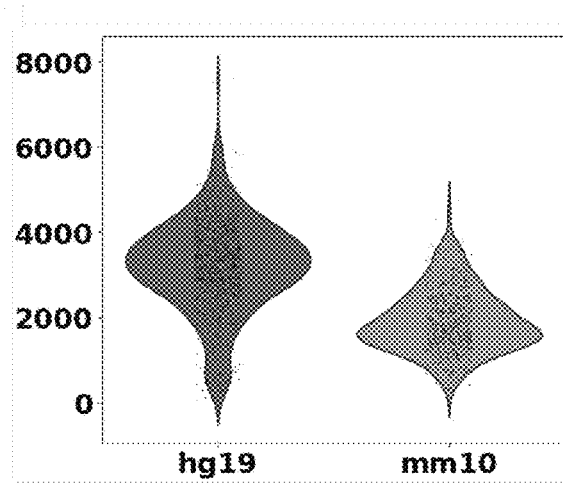
Figure 27A:
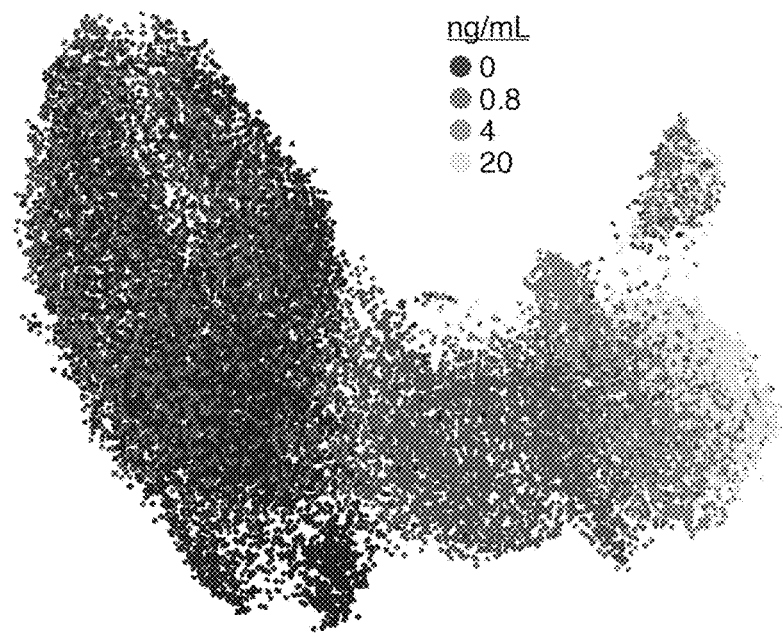
FIGS. 27A-27D depict data related to UMAP embedding showing cells from the 96-sample perturbation experiment colored according to the experimental treatment for each cell. Global trends such as EGF/bFGF dependence, BMP4 response, and retinoic acid-driven proliferation are evident.
Figure 27B:
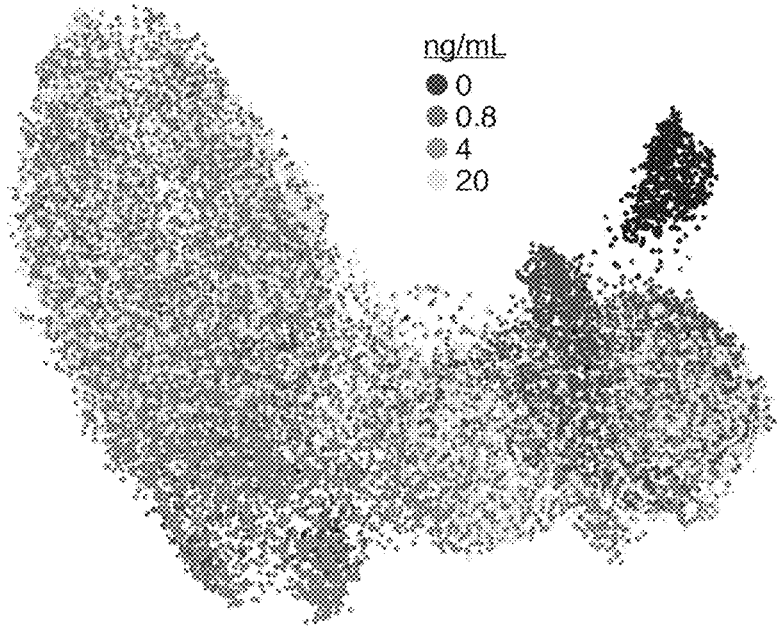
Figure 27C:
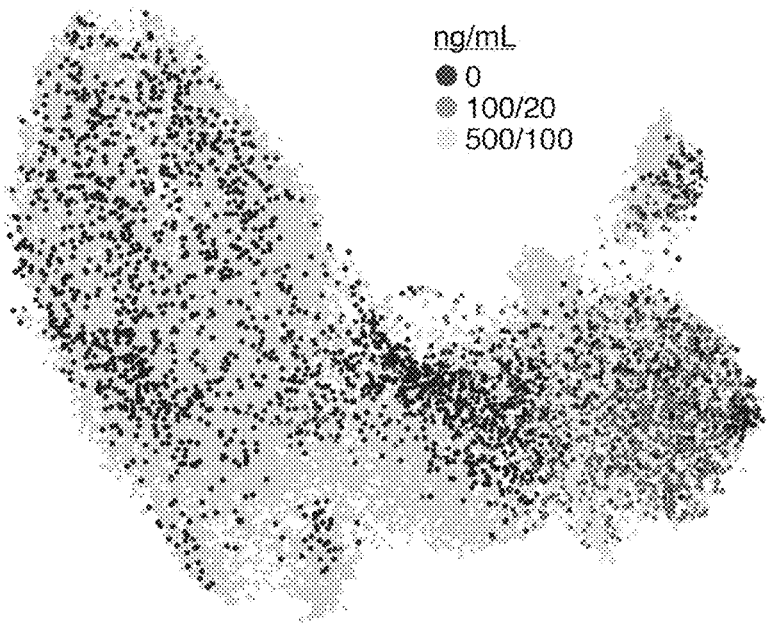
Figure 27D:
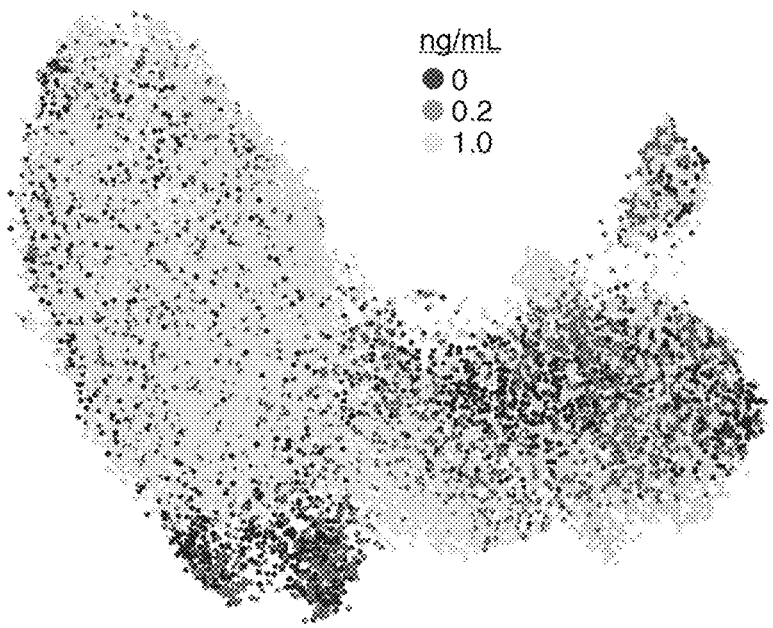

For the species-mixing experiment, 11,264 valid cell barcodes were selected by Cell Ranger using the rank-UMI vs. cell barcode plot for the cDNA libraries. The same cell barcodes were extracted from a cells×ClickTags matrix created using the kITE procedure described above. After normalizing each cell to 1,000 ClickTag counts, the data were log-transformed and the number of counts regressed out using ScanPy 'regress_out'. The resulting matrix was embedded with t-SNE and clustered by Louvain community detection. Of the nine clusters produced, one cluster showed greatly reduced UMI counts from both ClickTag and cDNA libraries and no clear correlation with any of the experimental groups (FIG. 25). The cells in this "noise cluster" were discarded, resulting in 10,482 high-quality cells which were used for downstream analysis. Doublet identification was compared across three methods: Cell Ranger (cDNA-based), Scrublet (ClickTag count-based), and manual cluster selection (ClickTag t-SNE-based). Manual selection was performed with the FlowJo cytometry analysis software, isolating individual sub-clusters from the t-SNE embedding.

For the 96-plex NSC experiment, sample assignment and doublet removal were similar to the four-sample NSC experiment, beginning with identification of 23,068 cells based on cDNA UMI counts. For each ClickTag, a threshold was calculated using the numpy gradient function to find the maximum slope of the rank-UMI vs cell barcode plot. Positive sample assignments were evaluated in comparison to the experimental design, and cells with sample assignments that did not exactly match a ClickTag combination used in the experiment were filtered out, yielding 21,191 high-quality cells.

cDNA Data Analysis

For the species-mixing experiment, the species origin of each cell was determined by Cell Ranger using cDNA counts from each genome, and droplets containing cells were selected by Cell Ranger using the rank-UMI x cell barcode plot. After filtering out cells with low ClickTag and cDNA counts (see above), the cDNA count data were normalized and log-transformed. Principal component analysis of the resulting matrix was followed by construction of a neighborhood graph and a UMAP embedding. These were computed using the ScanPy 'neighbors' and 'UMAP' functions with default settings.

Figure 24A:
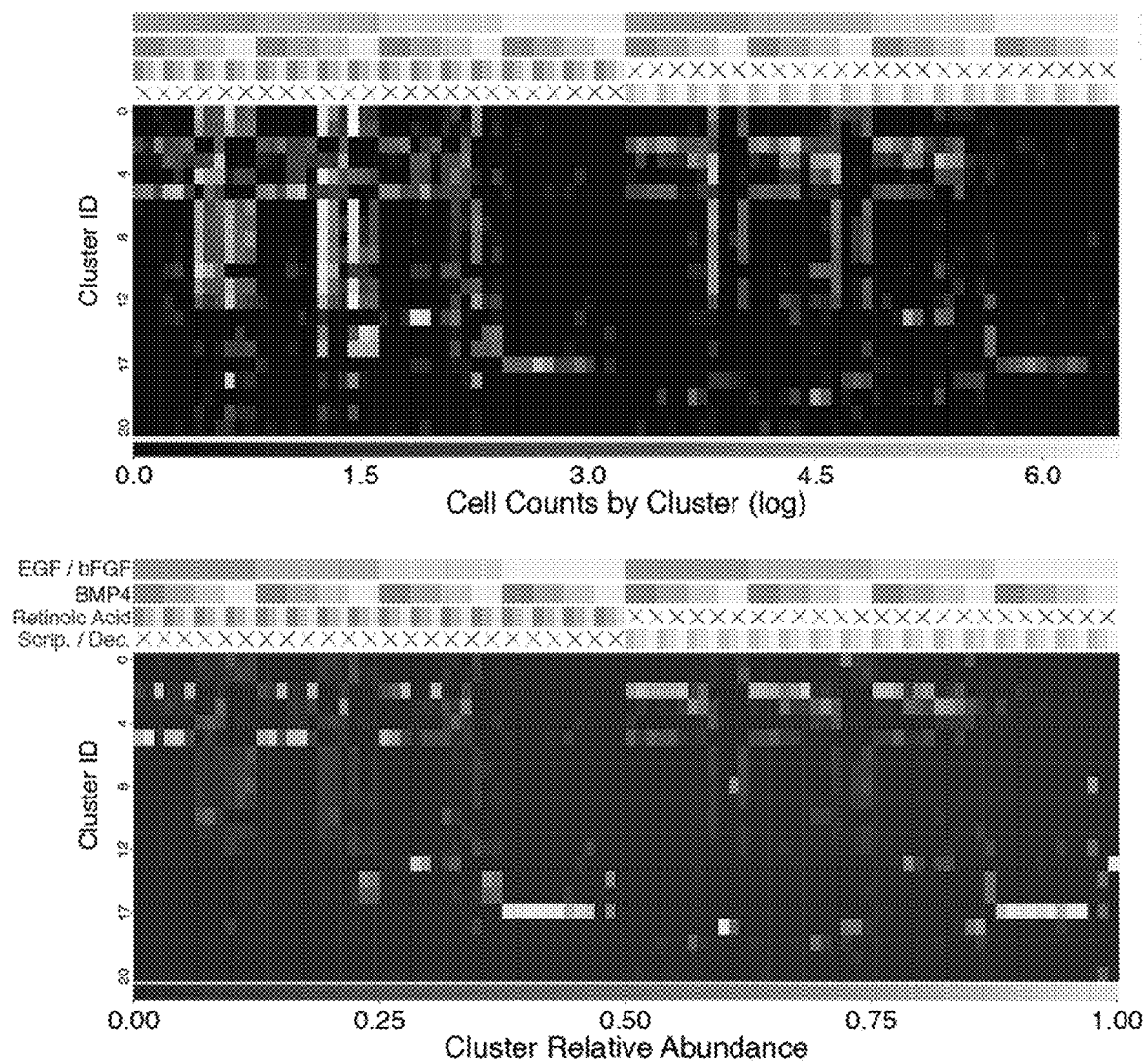
FIGS. 24A-24D depict data related to the perturbation response at single-cell resolution.
Figure 24B:
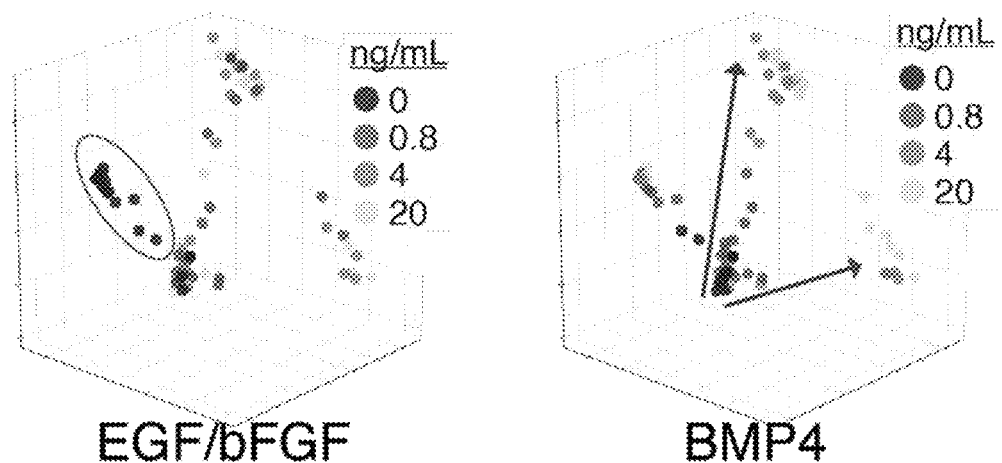
Figure 24B:
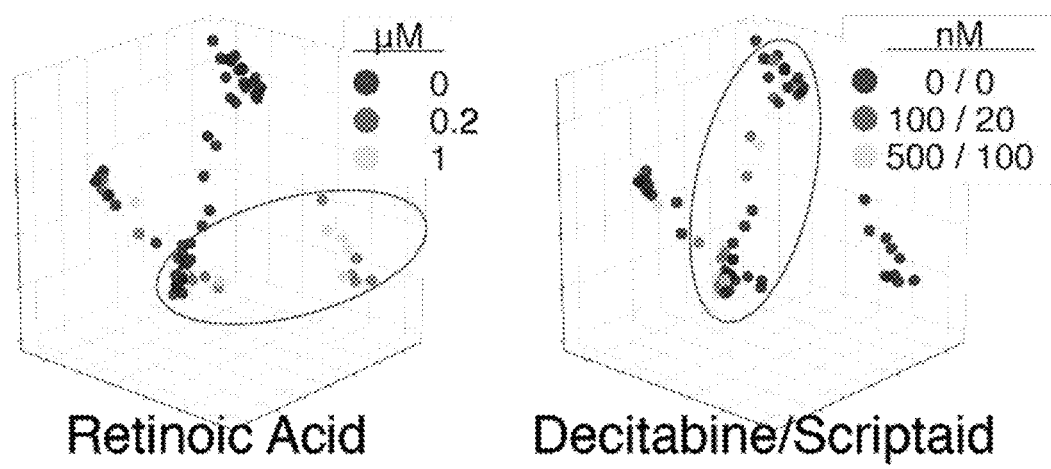
Figure 24C:
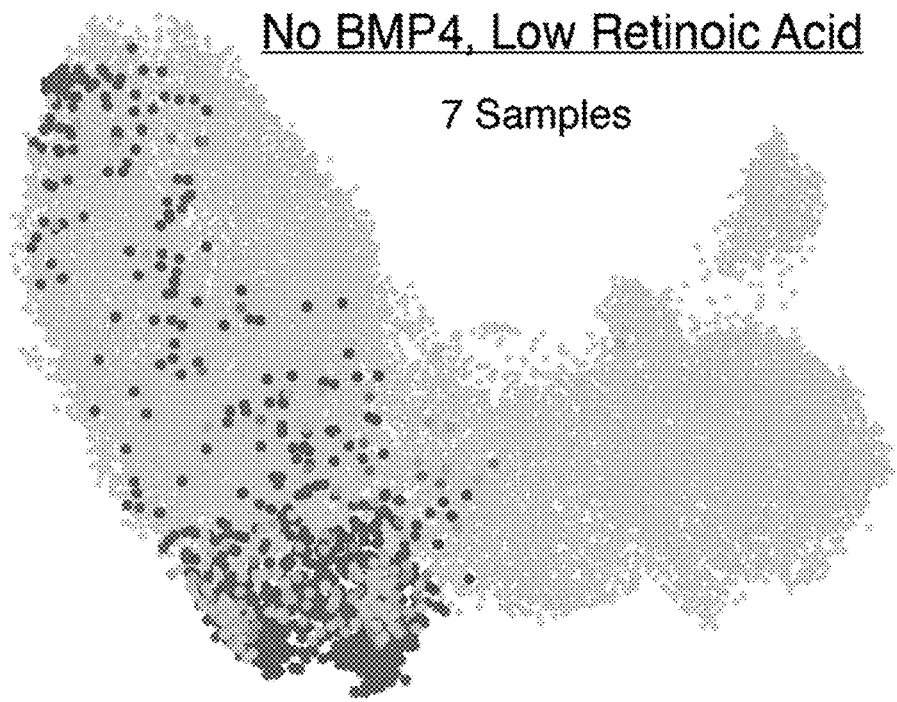
Figure 24C:
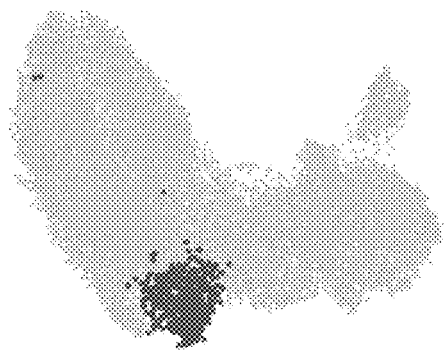
Figure 24C:
Figure 24C:
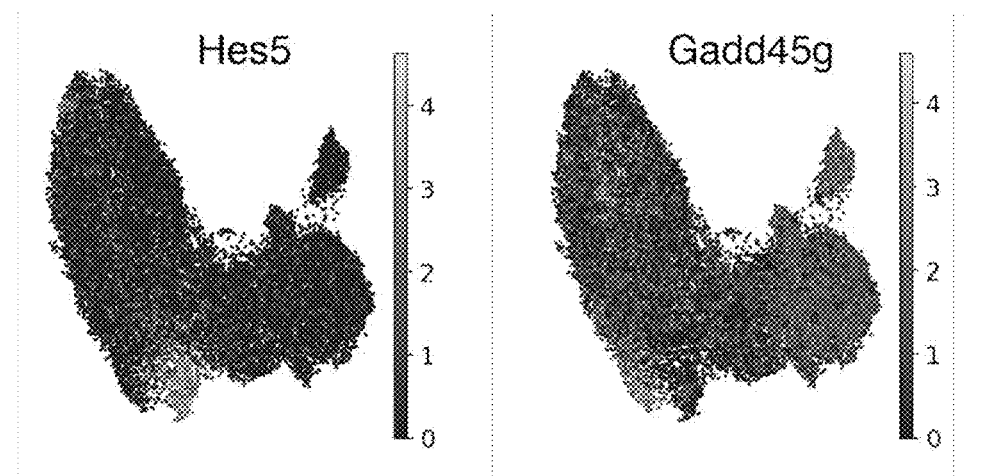
Figure 24D:
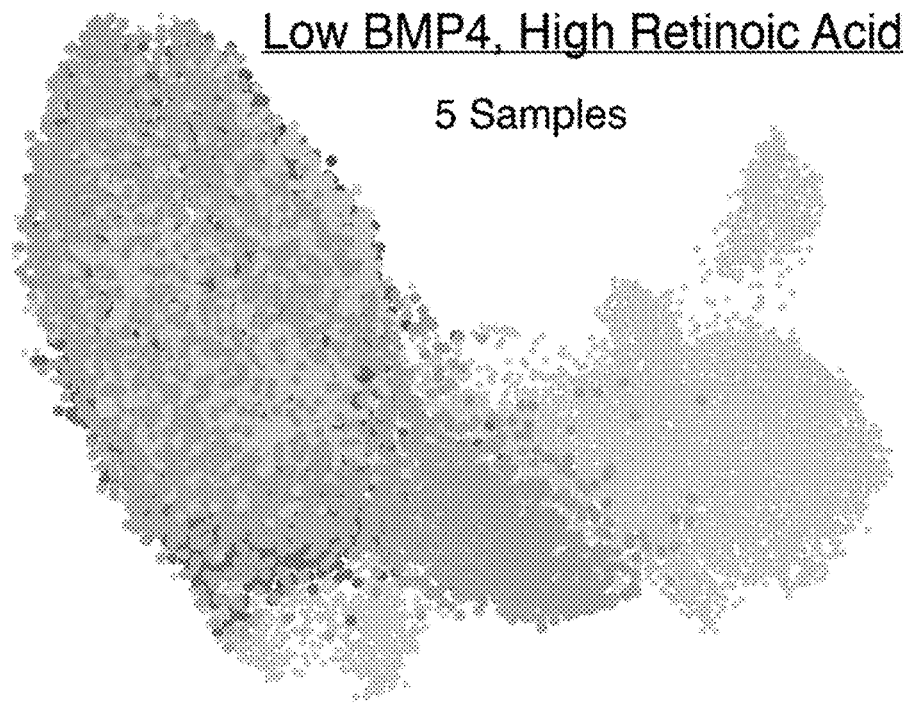
Figure 24D:
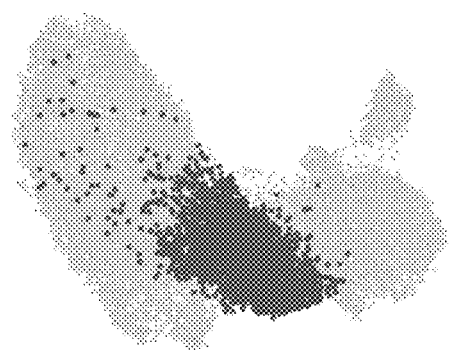
Figure 24D:
Figure 24D:
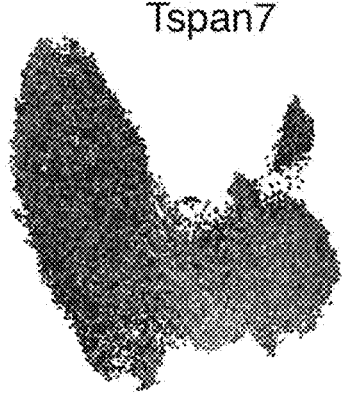
Figure 24D:
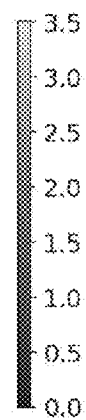
Figure 24D:
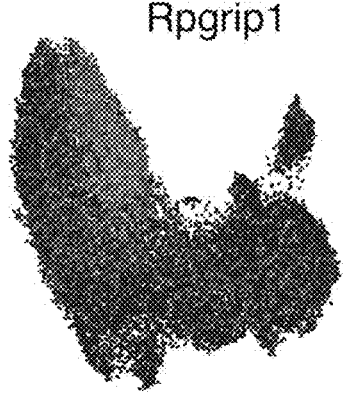
Figure 24D:
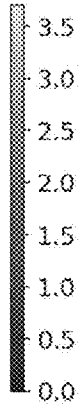

For the 96-sample perturbation experiment, high-quality cells were selected as described above, and again ScanPy was used normalize and log-transform the data. Highly variable genes were selected as those with mean normalized counts>0.0125 and <5 and with dispersion>0.5, yielding 1,860 highly variable genes. The per-cell read counts were regressed out and the data scaled to unit variance. Principal component analysis was performed on this matrix, followed by generation of a neighborhood graph using the top 40 principal components. The neighborhood graph was used to compute a UMAP embedding, and clustering was performed using the 'louvain' command in ScanPy. For clustering based on Louvain community detection, the resolution parameter was adjusted to agree with subpopulations produced by the perturbation experiment. It was reasoned that these natural groupings represent reproducible, quantitatively distinct biological states under the conditions of our experiment and would thus hold the most information relevant to the changing experimental parameters. In practice, a resolution setting of 2.2 yielded clusters that were in best agreement agreed with the sample-specific subpopulations produced by the perturbation experiment. Sample assignments were combined with cluster assignments from each cell to produce a matrix of cluster occupancy×experimental condition as well as a normalized version of the same matrix consisting of cluster relative abundance for each sample (FIG. 24A). Principal component analysis was performed on the cluster relative abundance matrix to visualize relationships between the experimental conditions used in our perturbation (FIG. 24B). Differential expression analysis was performed with the rank_genes_groups function in ScanPy. The top differential genes between the cluster(s) of interest and the rest of the dataset are shown (FIGS. 24C-24D). Linear regression was performed using the statsmodels Python package. The concentrations of the perturbants applied to each cell were used as independent variables and the corresponding gene expression for that cell set as the dependent variable. Regression was performed for all highly variable genes and all high-quality cells. Genes with strong condition dependence were selected based on their p-values from this model.

Example 5

Highly Multiplexed Single-Cell RNA-Seq for Defining Cell Population and Transcriptional Spaces This example describes a universal sample multiplexing method for single-cell RNA-seq in which cells are chemically labeled with identifying DNA oligonucleotides. Analysis of a 96-plex perturbation experiment revealed changes in cell population structure and transcriptional states that cannot be discerned from bulk measurements, establishing a cost effective means to survey cell populations from large experiments and clinical samples with the depth and resolution of single-cell RNA-seq.

Massively parallel single-cell RNA-sequencing (scRNA-seq) is transforming our view of complex tissues and yielding new insights into functional states of heterogeneous cell populations. Currently, individual scRNA-seq experiments can routinely probe the transcriptomes of more than ten thousand cells, and in the past year the first datasets approaching and exceeding one million cells have been reported. However, despite numerous technical breakthroughs that have increased cell capacity of many scRNA-seq platforms, researchers are at present limited in the number of samples that can be assayed. Many biological and therapeutic problems rely on finding genes or signals responsible for a phenotype of interest from screens involving hundreds, or even thousands, of samples. High-throughput analysis of genetic, signaling, and drug perturbations by scRNA-seq therefore requires effective multiplexing procedures to overcome the limitations imposed by device operation, high reagent cost, and batch effect.

This example presents a novel approach to scRNA-seq multiplexing that allows for cells from individual samples to be rapidly chemically labeled with identifying DNA oligonucleotides (FIG. 9B). This example describes a one-pot, two-step chemical cross-linking reaction that is independent of specific epitopes, sequence markers, or genetic manipulation. The disclosed universal workflow attaches methyltetrazine-modified DNA oligos, or "ClickTags", to cellular proteins using inverse electron-demand Diels-Alder (IEDDA) chemistry and the heterobifunctional, amine-reactive cross-linker NHS-trans-cyclooctene (NHS-TCO). After demonstrating effective labeling conditions on yeast cells (FIG. 10), a multiplexed scRNA-seq experiment was performed in which four samples of live mouse neural stem cells (NSCs) and four samples of methanol-fixed NSCs were each labeled with two unique ClickTags. The ClickTags can be specifically amplified and sequenced with a modified 10× Genomics Single Cell Gene Expression protocol, and we employed a computational workflow, kITE (kallisto Indexing and Tag Extraction), to rapidly pseudoalign ClickTag reads to an index of barcodes (FIG. 11). ClickTag reads from methanol-fixed cells accurately recapitulated the experimental design with a high correlation between UMI counts for pairs of tags applied to the same sample, indicating efficient single-cell labeling, and facilitating sample demultiplexing (FIGS. 12 and 13). Cell doublet events were unambiguously detected as collisions of two pairs of tags corresponding to two separate samples (FIG. 14).

Figure 16A:
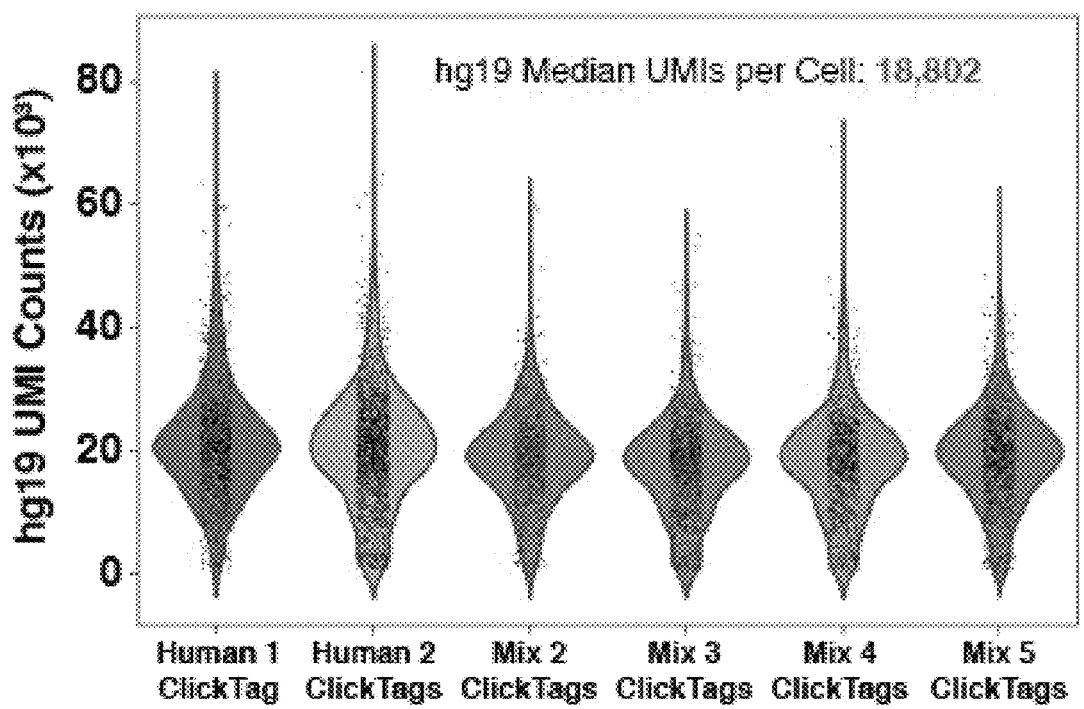
FIGS. 16A-16C depict data related to comparison of human cDNA libraries across samples from the species-mixing experiment.
Figure 16B:
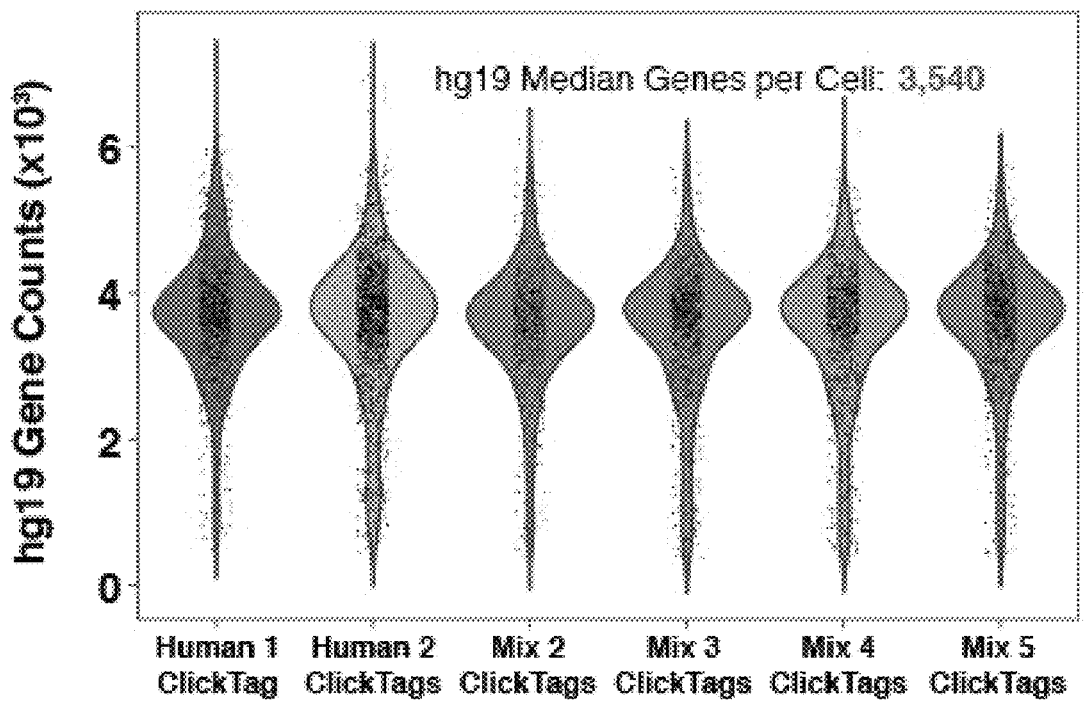
Figure 16C:
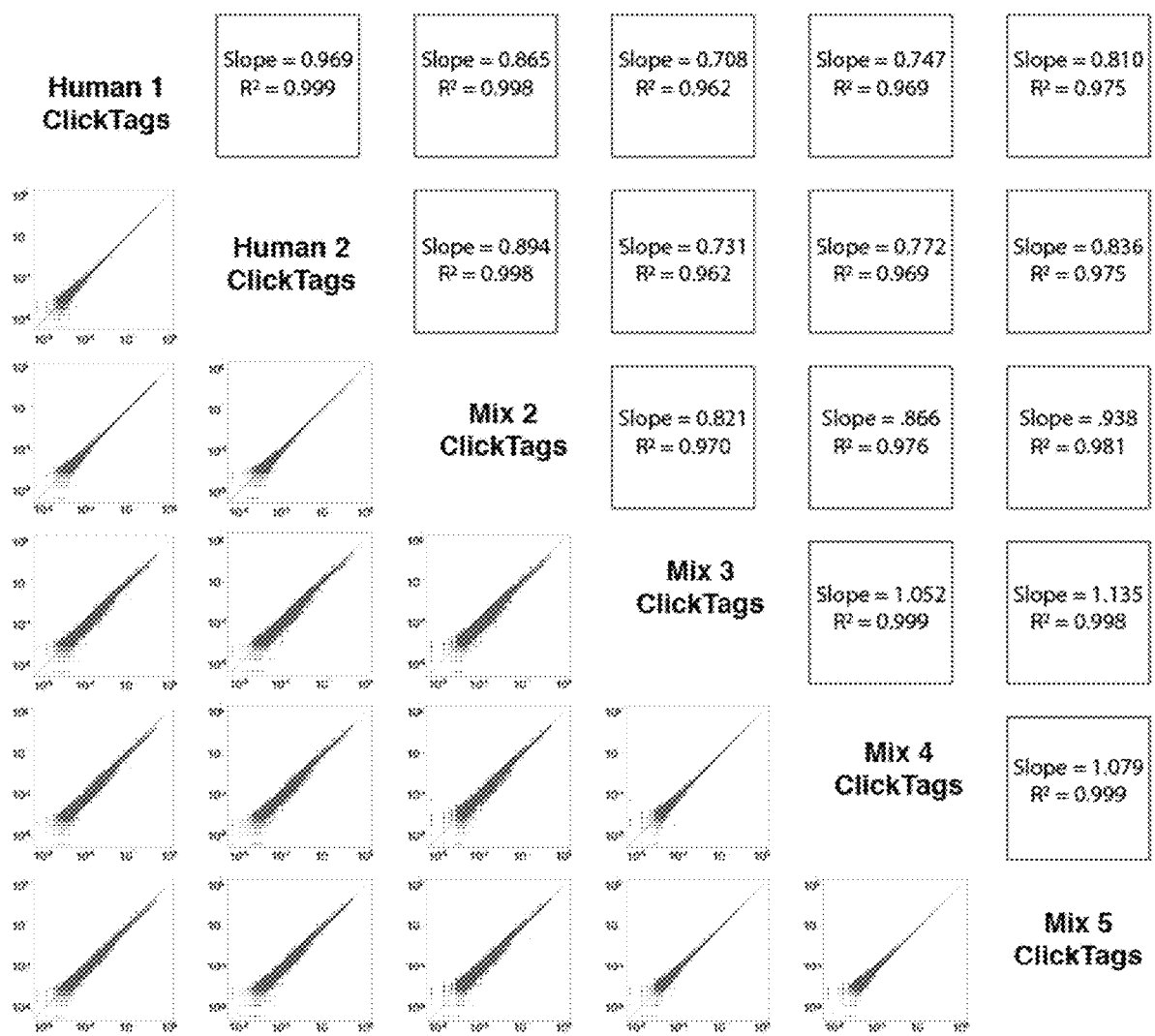
Figure 17A:
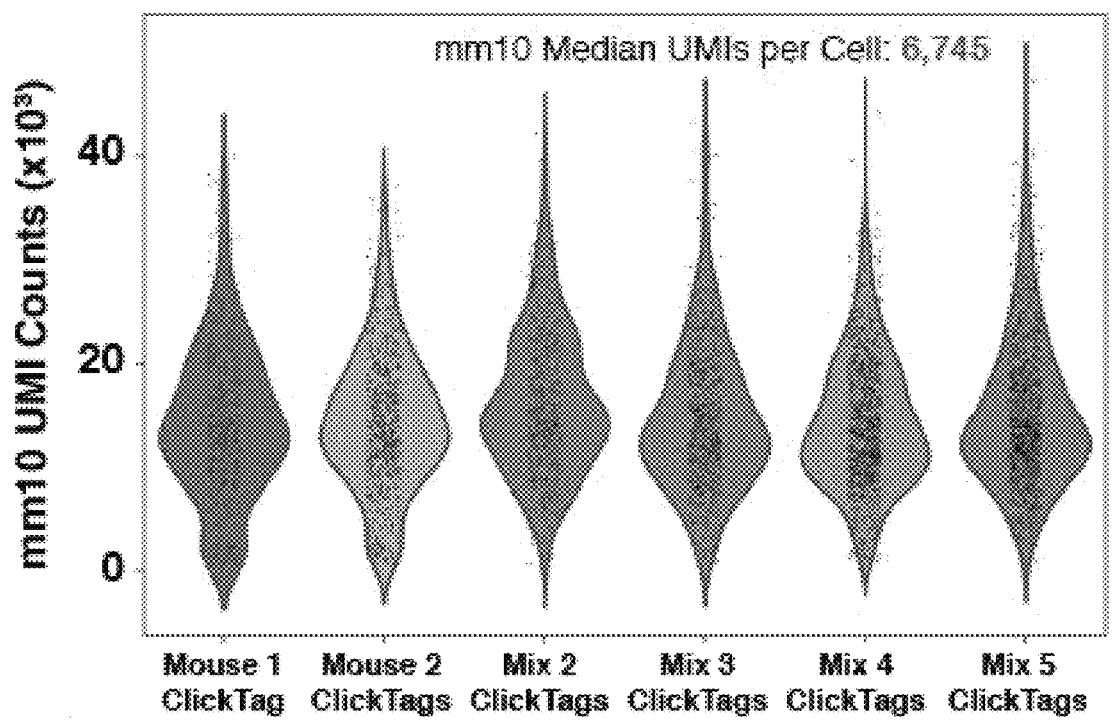
FIGS. 17A-17C depict data related to comparison of mouse cDNA libraries across samples from species-mixing experiment.
Figure 17B:
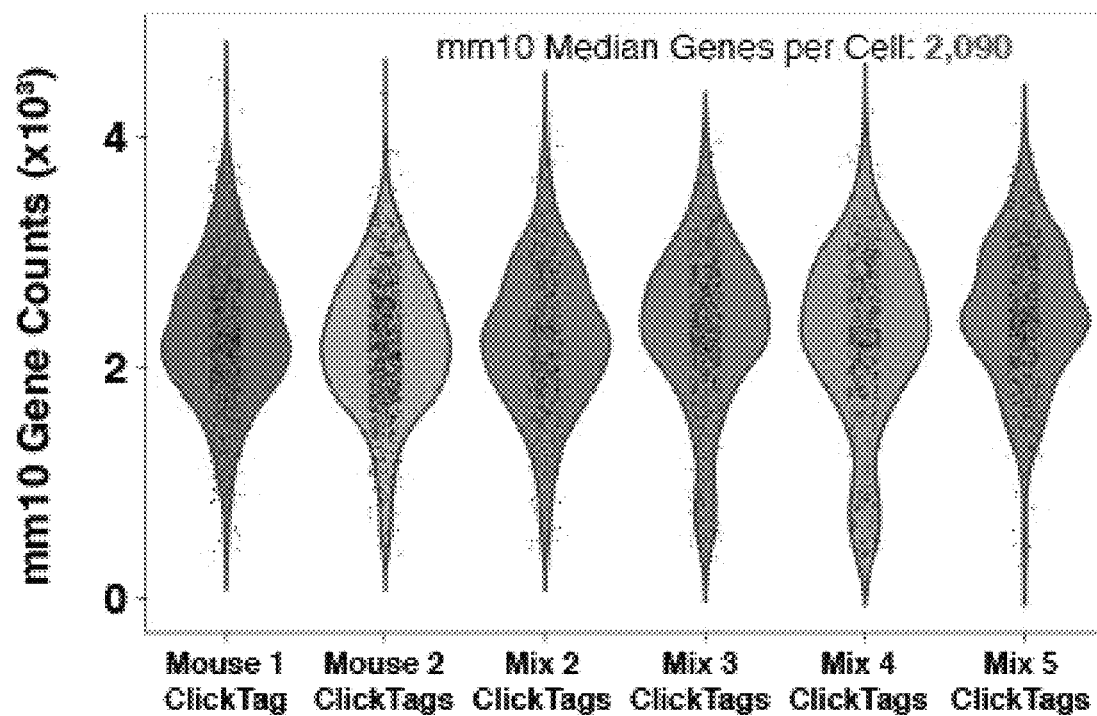
Figure 17C:
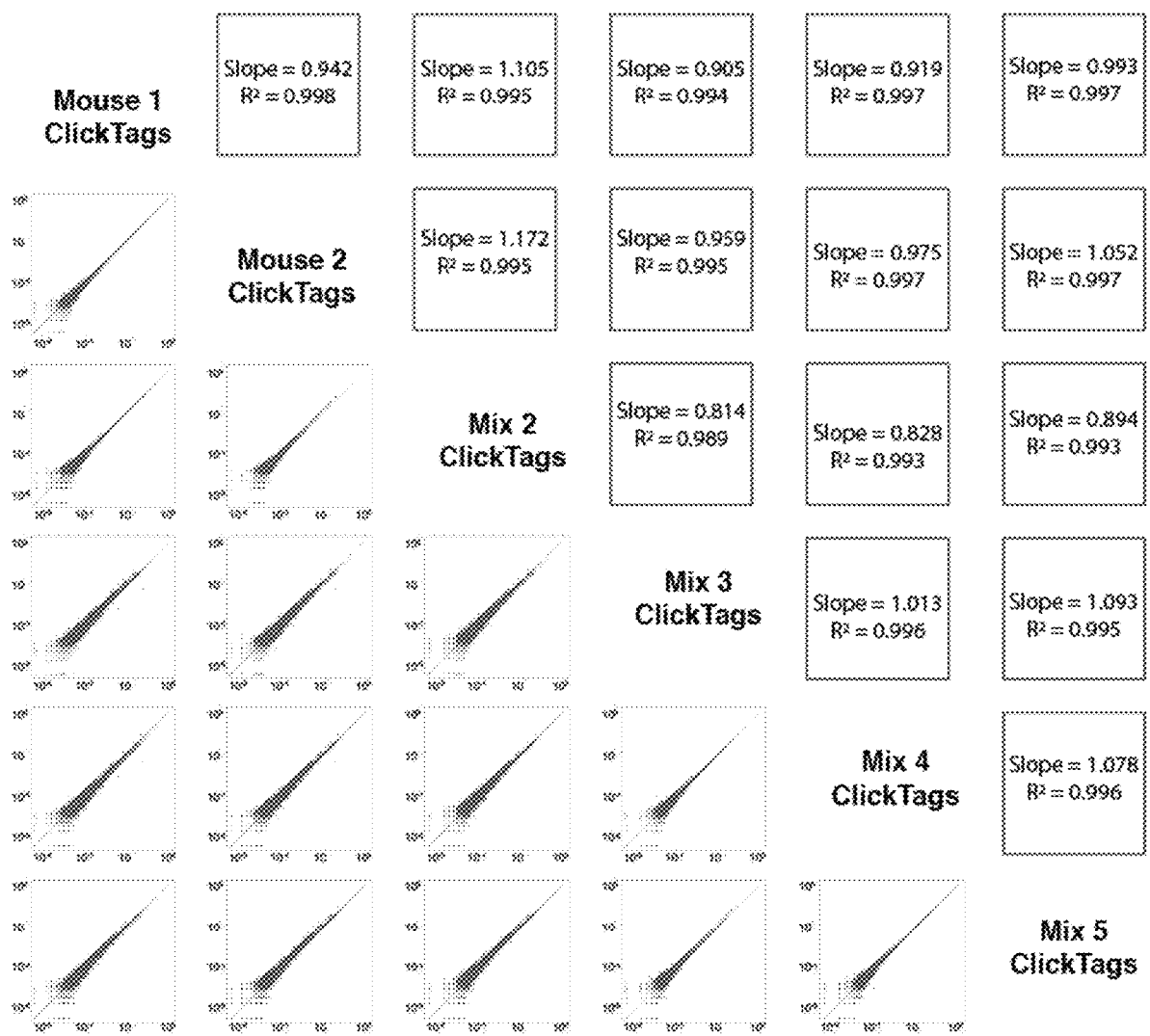
Figure 18A:
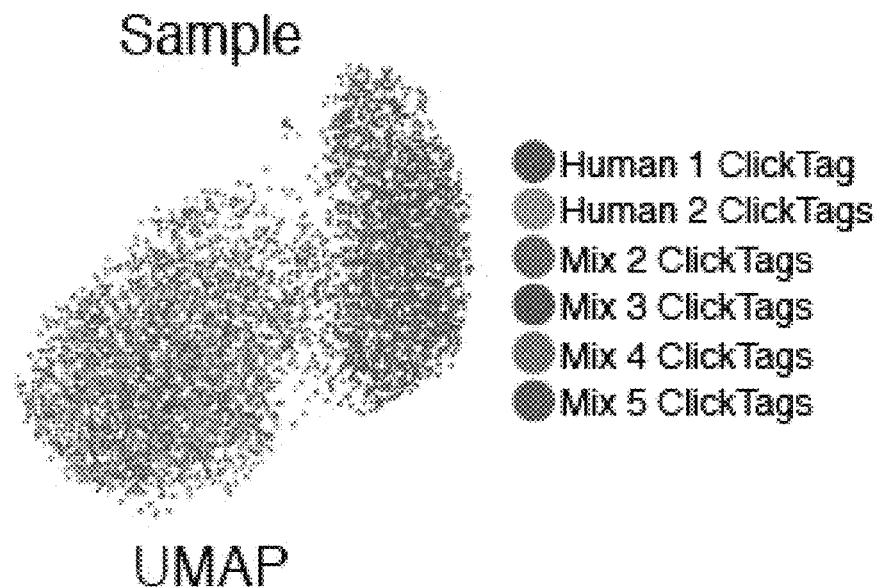
FIGS. 18A-18E depict data related to the effect of Click-Tag concentration on human gene expression quantification.
Figure 18B:
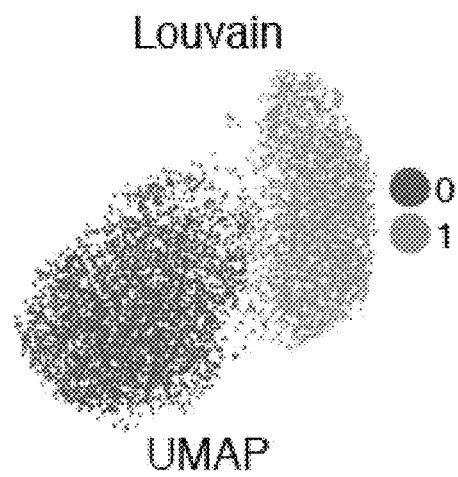
Figure 18C:
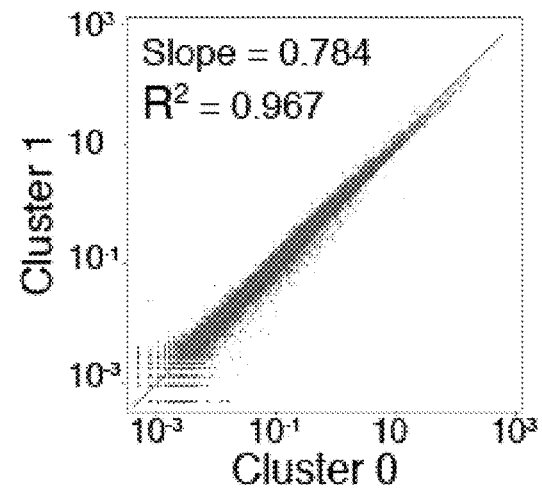
Figure 18D:
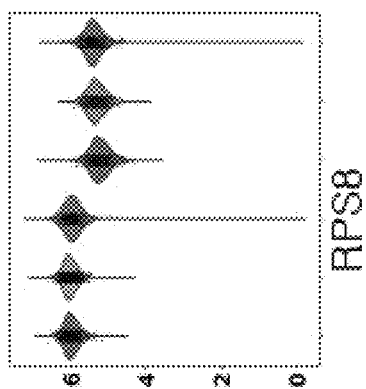
Figure 18D:
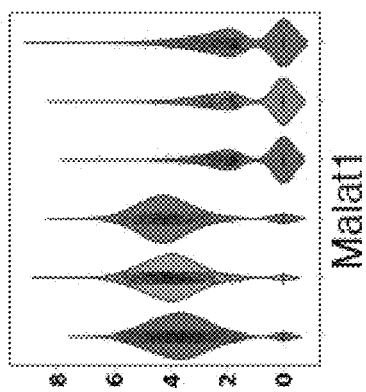
Figure 18D:
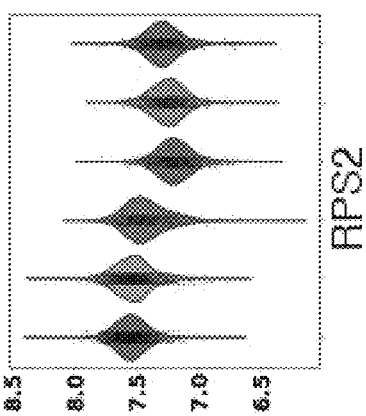
Figure 18D:
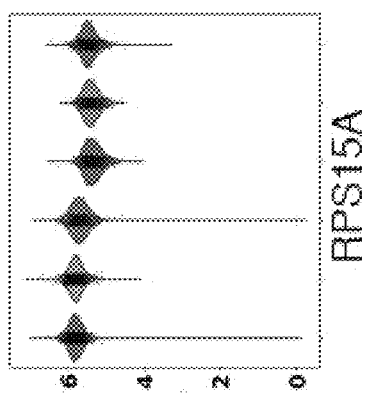
Figure 18E:
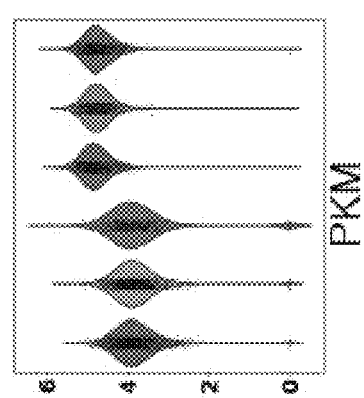
Figure 18E:
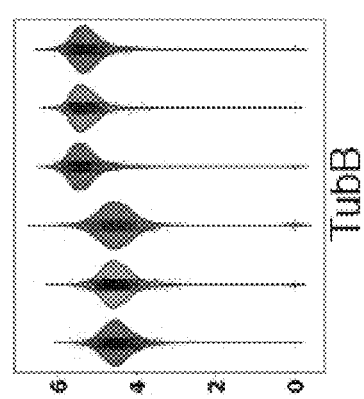
Figure 18E:
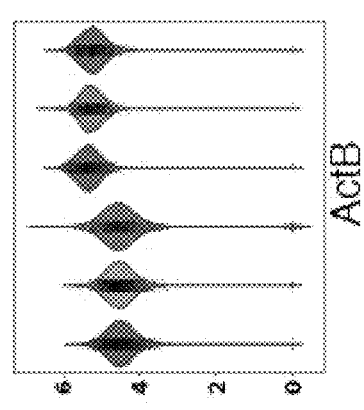
Figure 18E:
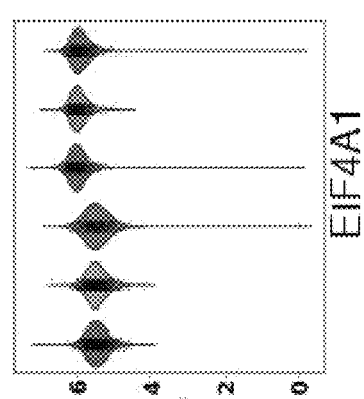
Figure 19A:
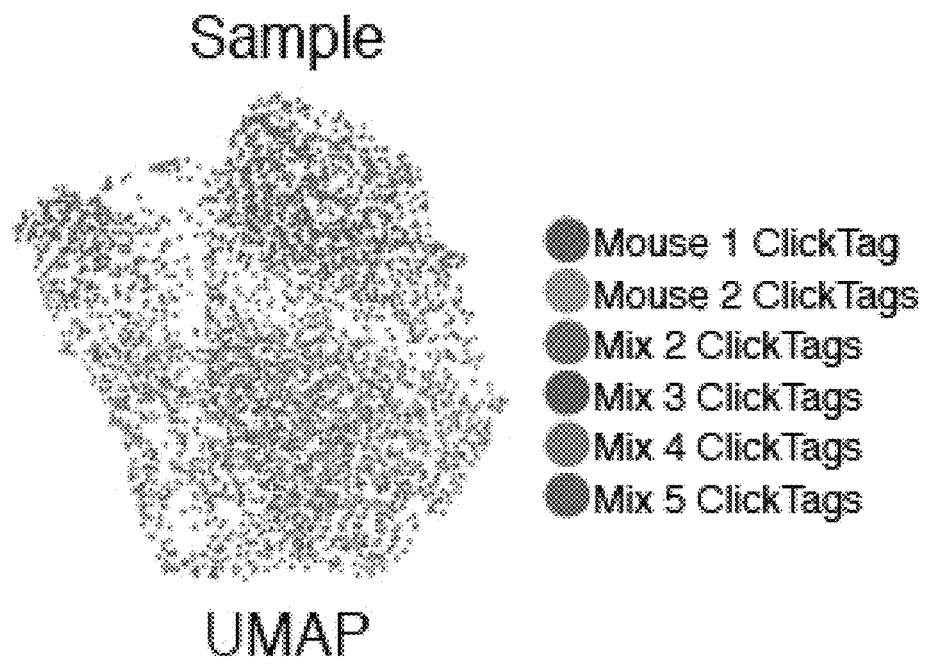
FIGS. 19A-19E depict data related to the effect of Click-Tag concentration on mouse gene expression quantification.
Figure 19B:
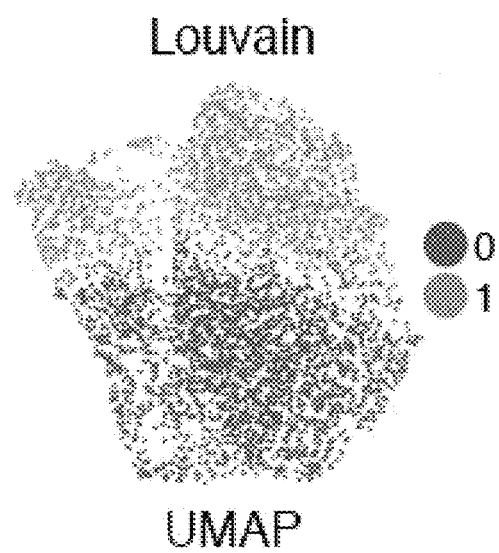
Figure 19C:
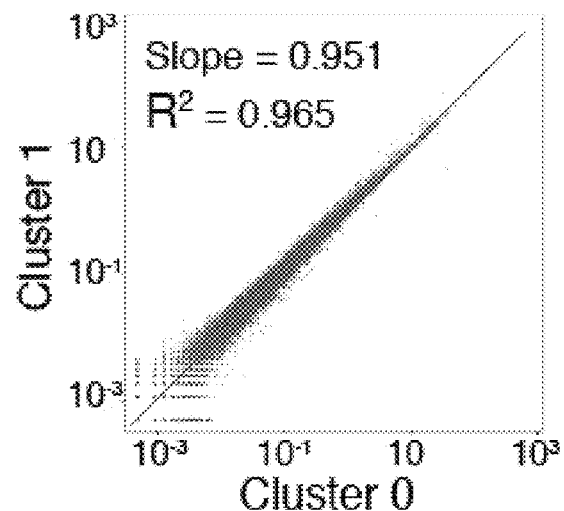
Figure 19D:
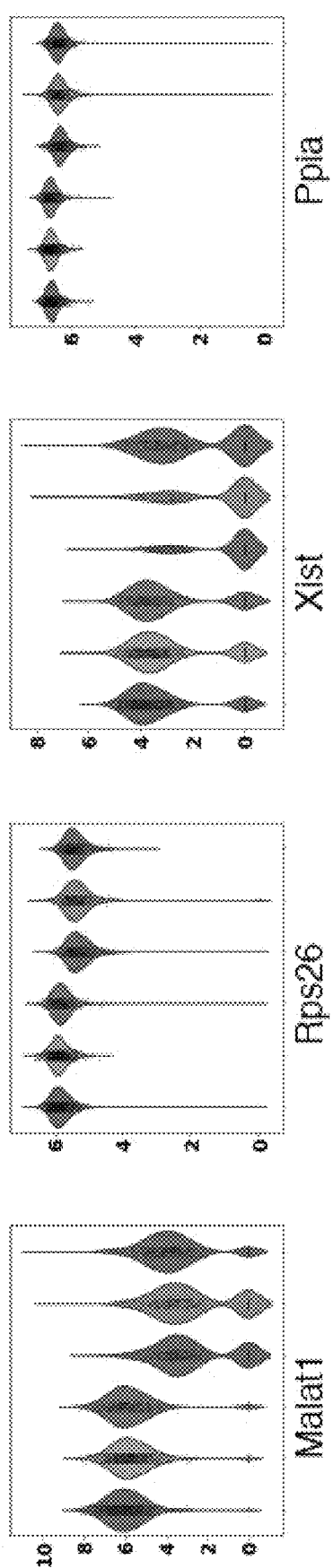
Figure 19E:
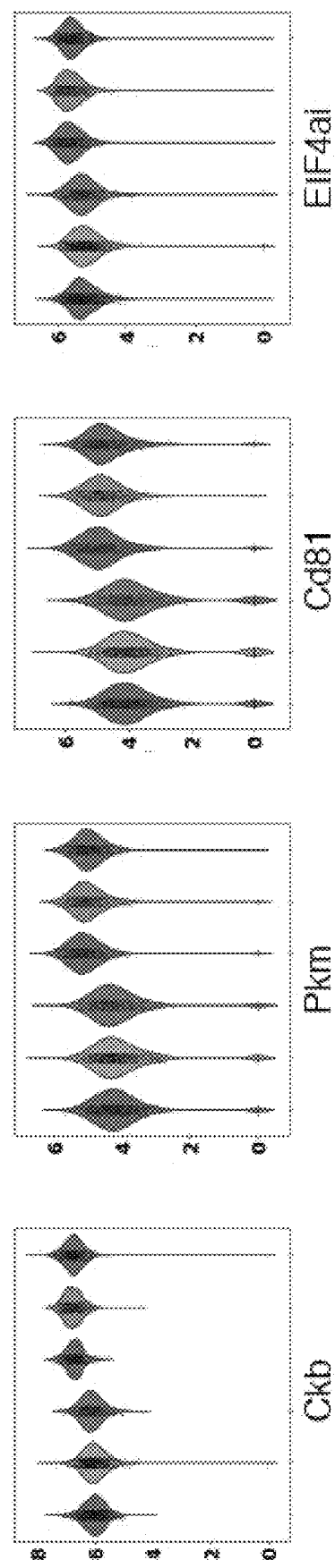

Next a complex species-mixing experiment was performed aimed at evaluating the limits of ClickTag multiplexing and quantifying any deleterious effects on the associated cDNA libraries. Samples of large, human HEK293T cells and small, mouse NSCs were fixed and reacted individually and in combination with a series of non-overlapping sample tag pools of increasing size (Table 3) and processed as a single lane of 10× targeting 10,000 cells. It was found that overall cDNA library quality was consistent with untagged methanol-fixed samples (FIG. 15), including a slight under-representation of low-expression genes, a slight over-representation of high-expression genes, and reduced library complexity compared to live cells. Samples labeled with one or two ClickTags displayed highly reproducible gene expression profiles, as did samples labeled with three, four, or five ClickTags, thus validating a "balanced" labeling scheme using the same number of ClickTags of equal concentration for all samples in multiplexing experiments (FIGS. 16 and 17). Interestingly, an examination of the differences between the 1, 2 and 3, 4, 5 ClickTag populations showed large changes in the non-coding RNAs MALAT1 and Xist (FIGS. 18 and 19), two highly expressed genes captured via internal A-rich binding sites that are frequently filtered prior to analysis.

Figure 20A:
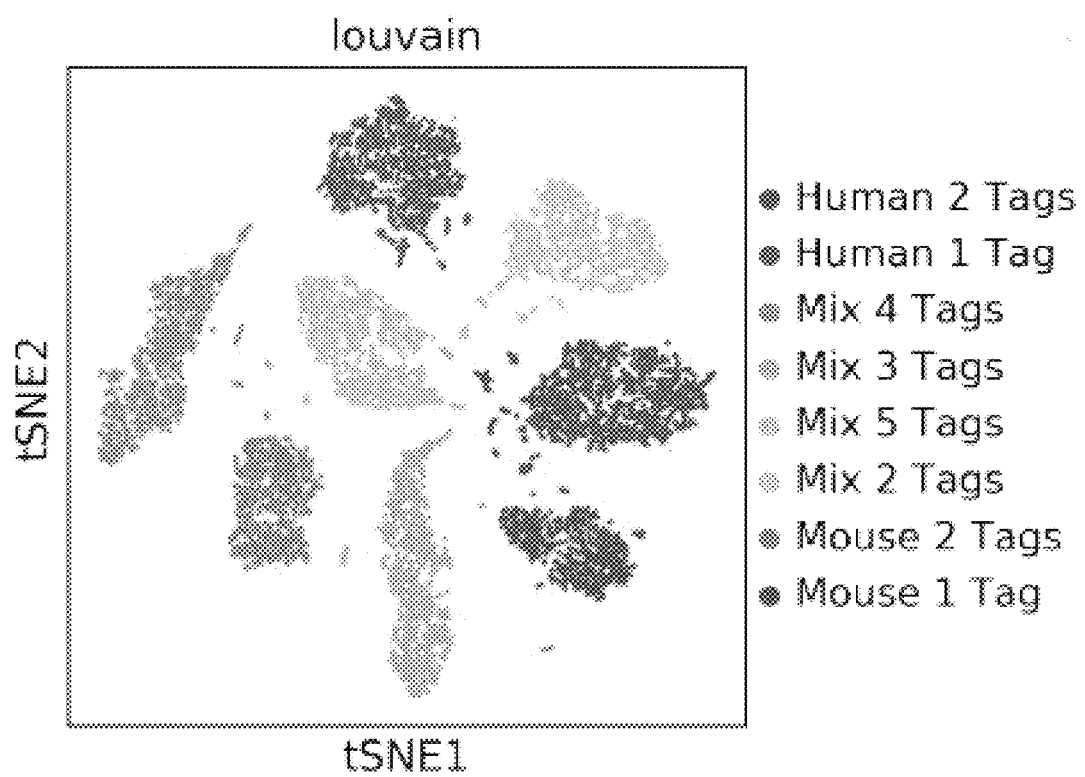
FIGS. 20A-20G depict data related to the combination of ClickTags and species information, which presented a unique opportunity for comparison of doublet detection methods. Doublets identified by CellRanger are necessarily limited to cross-species events, while ClickTags are similarly only relevant for detection of doublets originating from different samples.
Figure 20B:
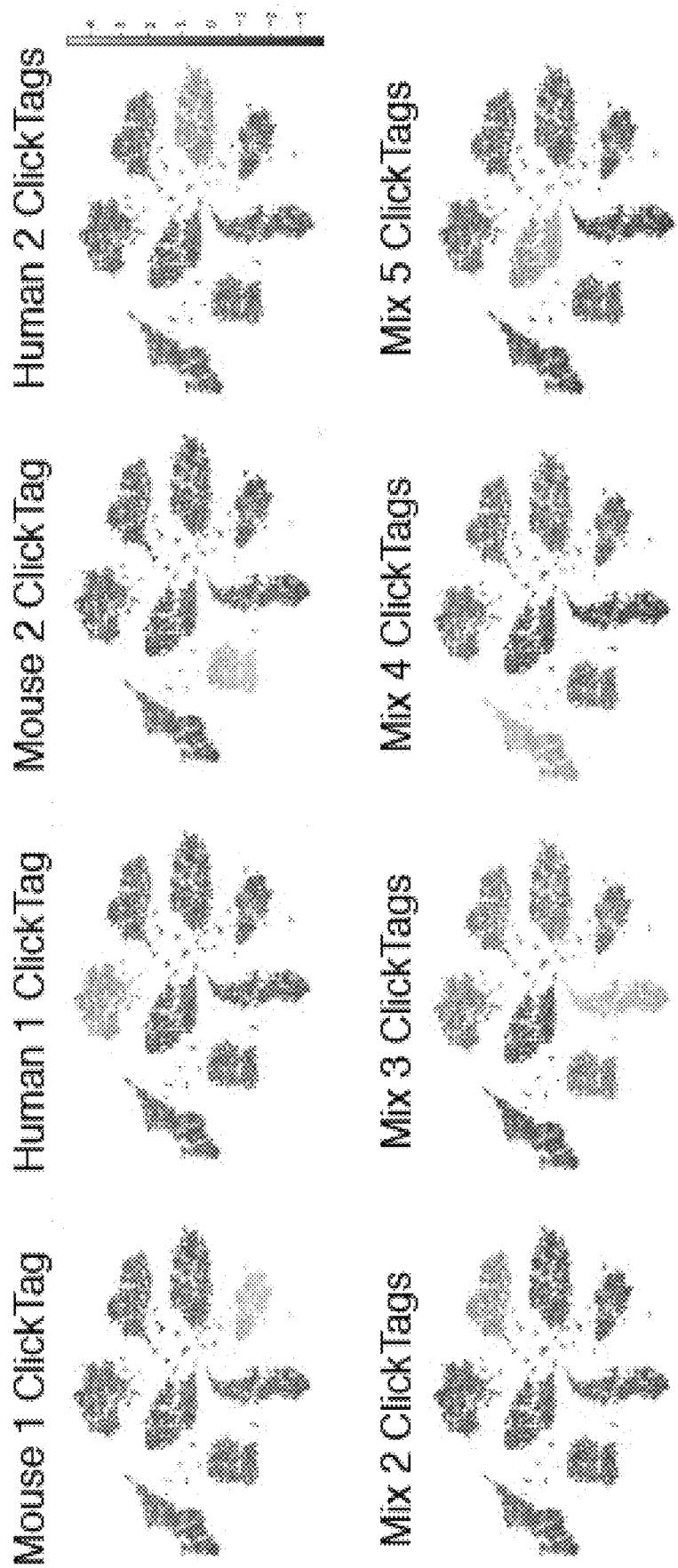
Figure 20C:
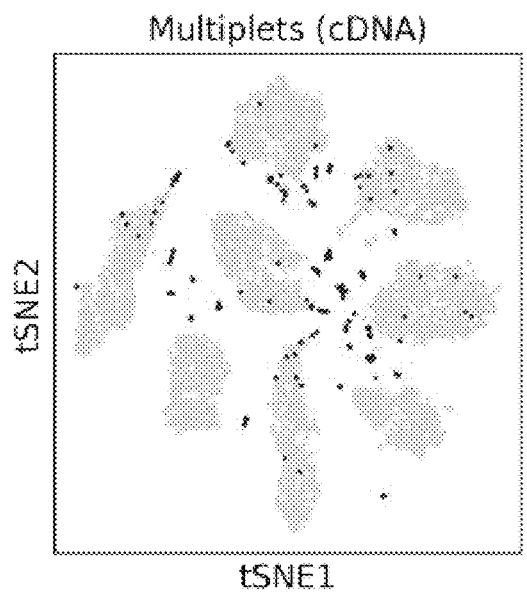
Figure 20D:
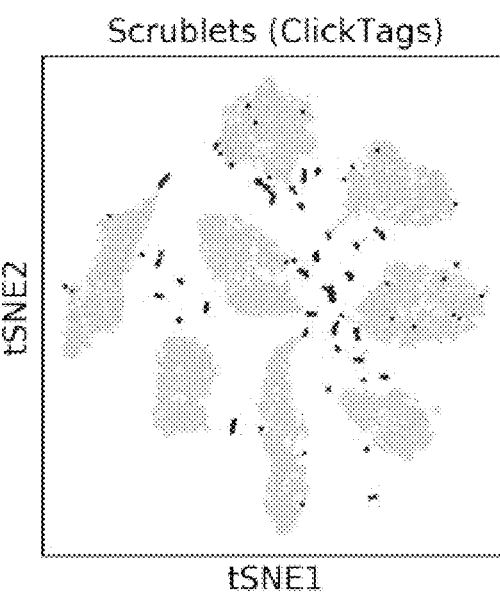
Figure 20E:
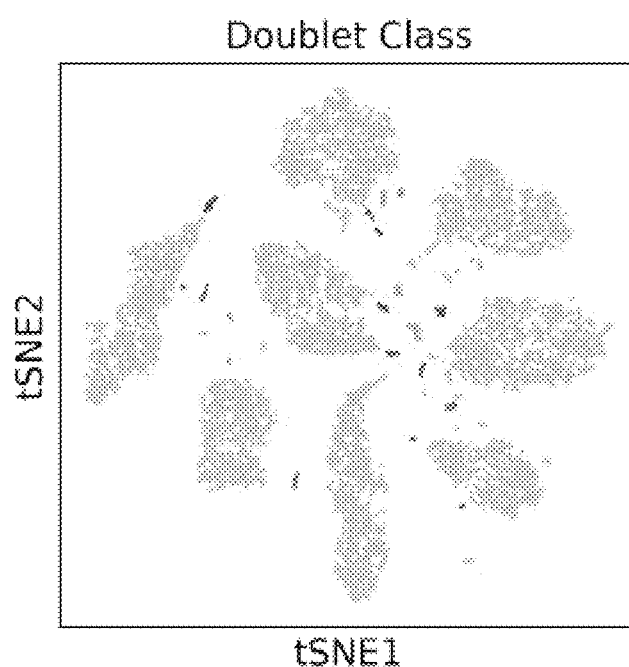
Figure 20F:
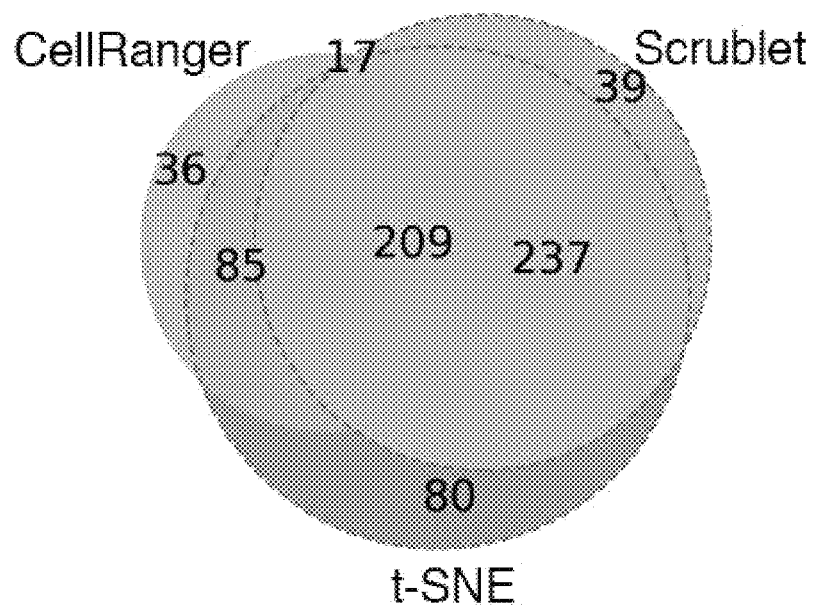
Figure 20G:
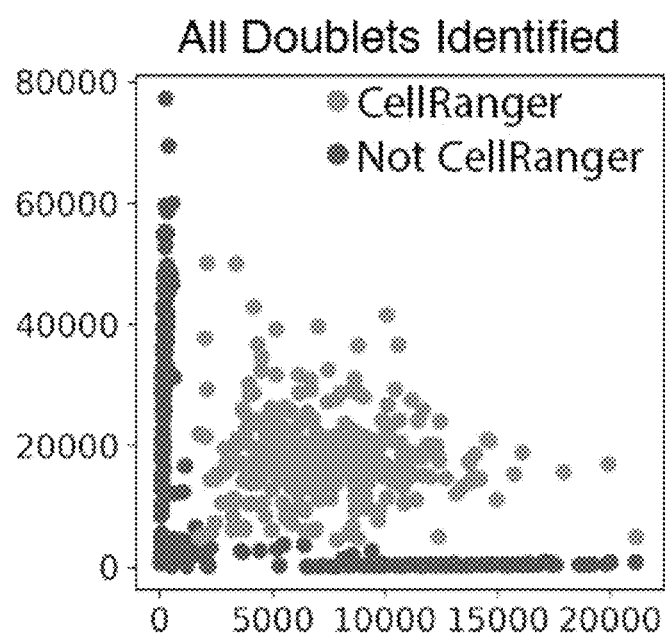
Figure 21A:
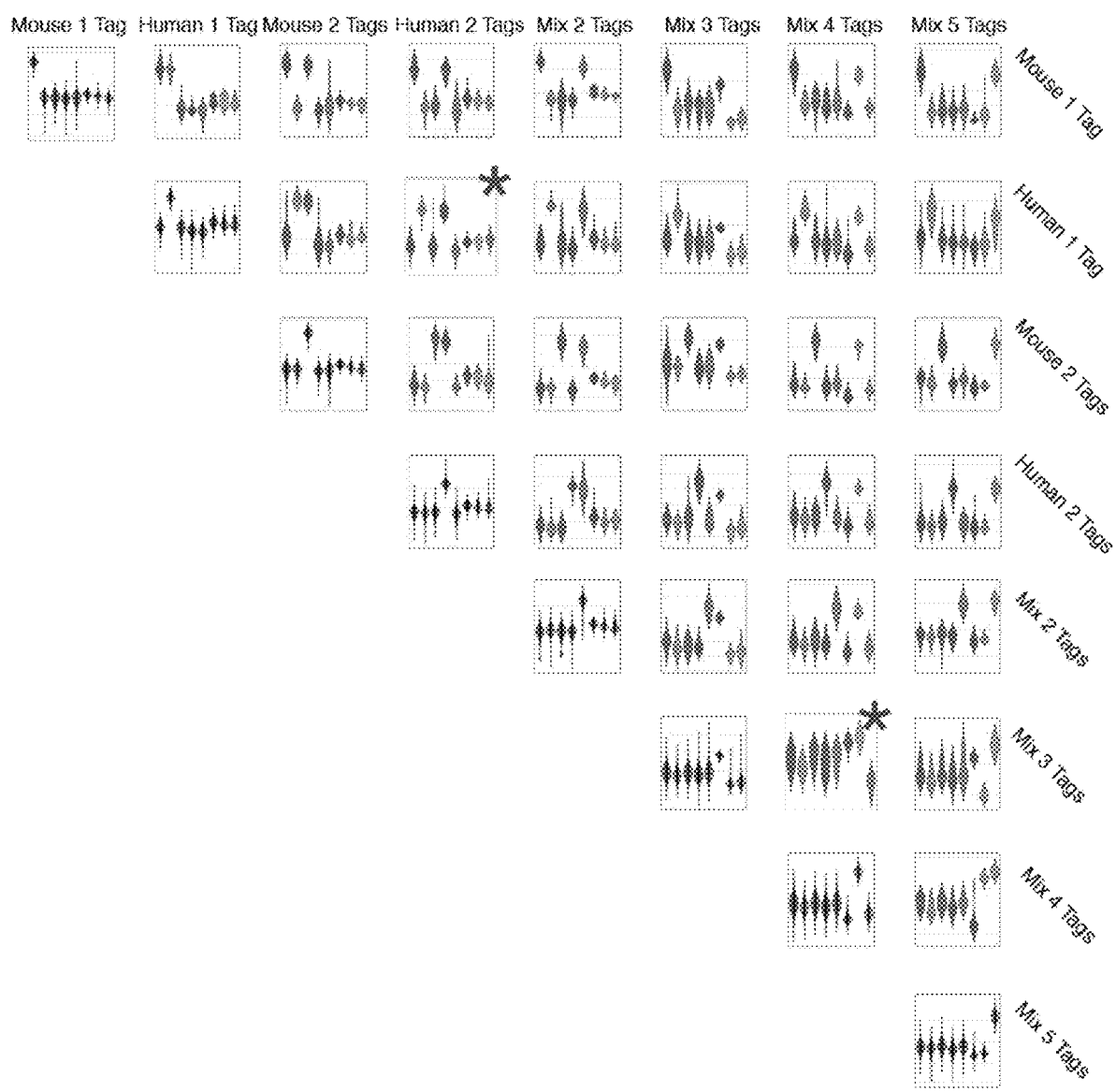
FIGS. 21A-21B depict data related to doublet classification for species-mixing experiment.
Figure 21B:
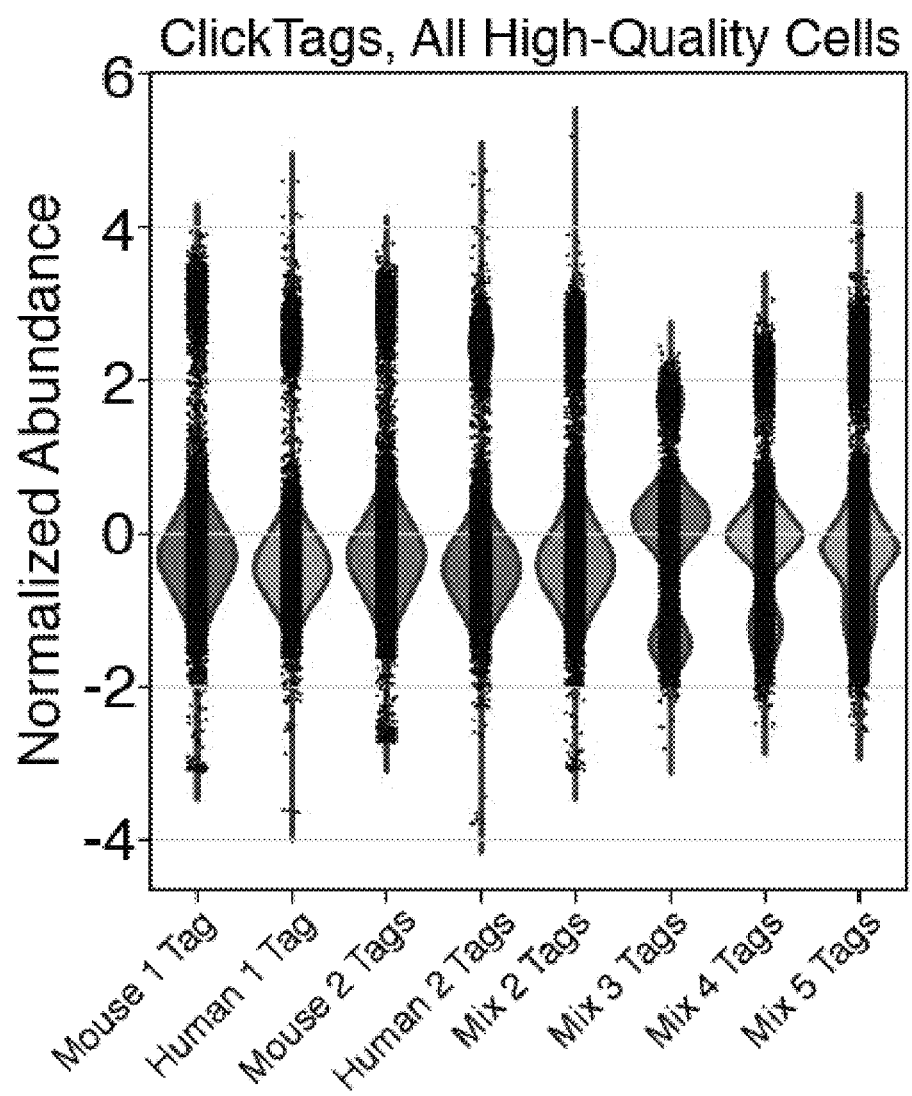
Figure 22A:
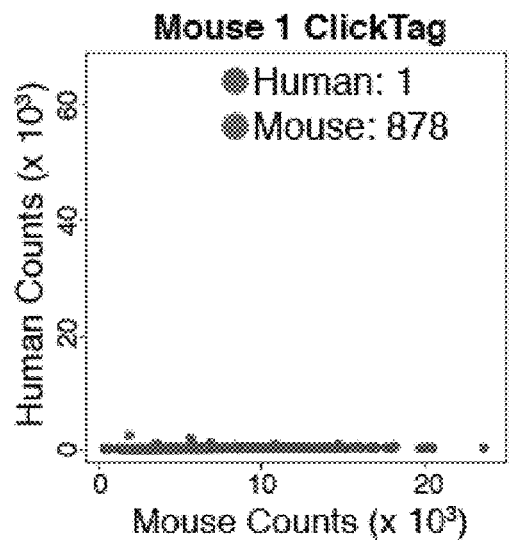
FIGS. 22A-22H show barnyard plots for droplets identified as singlets following the manual selection procedure described in the caption of FIG. 20.
Figure 22B:
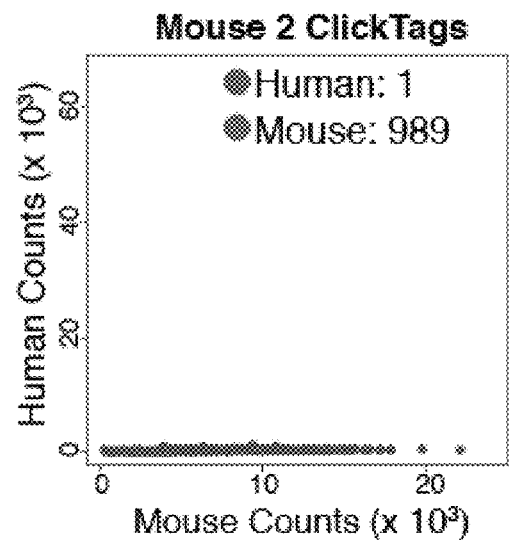
Figure 22C:
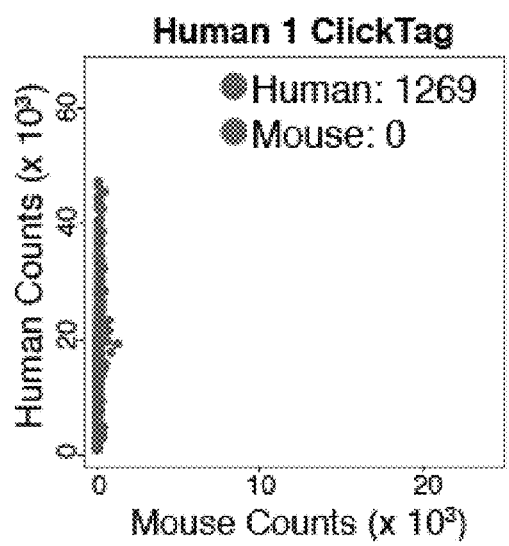
Figure 22D:
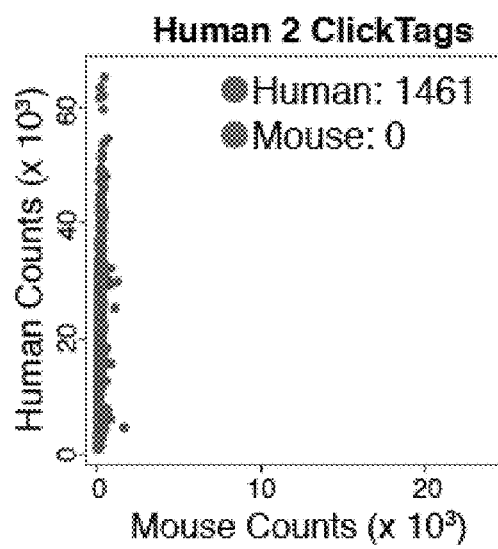
Figure 22E:
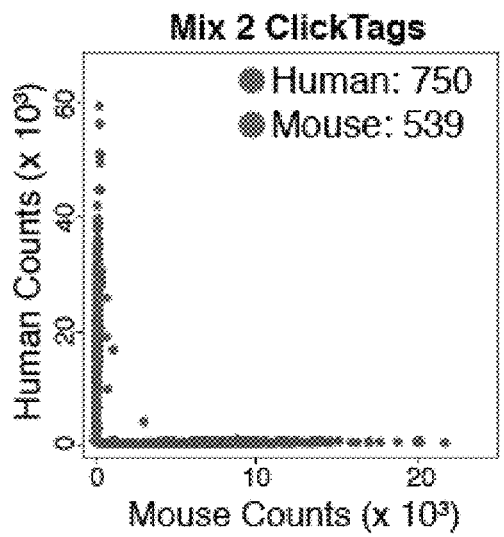
Figure 22F:
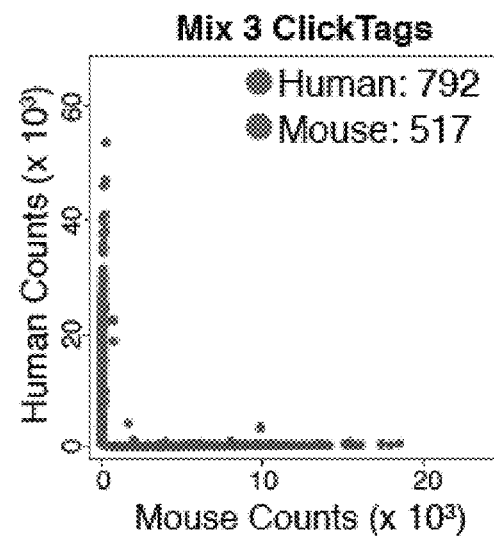
Figure 22G:
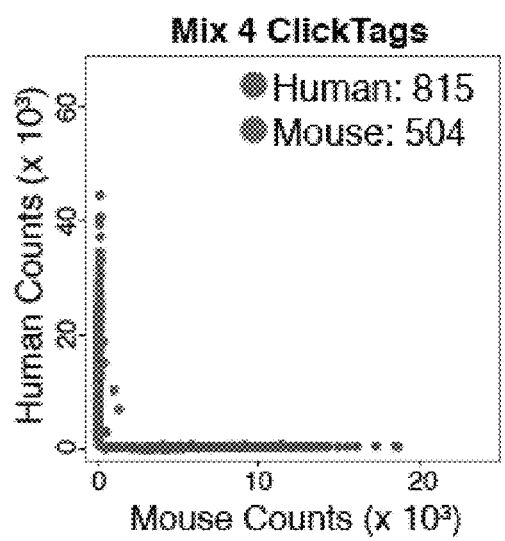
Figure 22H:
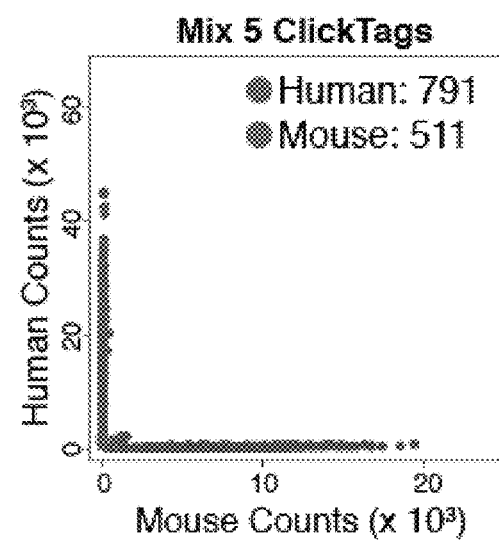

Filtering, clustering and embedding ClickTag data from this species mixing experiment revealed 8 distinct clusters of cells and high concordance with the experimental design (see Methods, FIGS. 20A-20B). Up to 5 ClickTags could be deposited on a single cell without loss of tag recovery, implying that in principle 15,504 experiments could be multiplexed with a panel of just 20 tags. Species and ClickTag information were used to filter out doublets, with identification by manual sub-cluster selection outperforming that of CellRanger (cDNA, inter-species events) and the Scrublet algorithm (ClickTags, inter-sample events) (FIGS. 20C-20G), achieving successful extraction of all 28 possible inter-sample collisions (FIG. 21). Barnyard plots generated from the resulting population of singlets showed near-perfect species fidelity in single-species samples, indicative of highly accurate sample assignment (FIG. 22). FIG. 26 depicts an analysis of ClickTag counts from human HEK293T and mouse neural stem cells from the multiplexed species-mixing experiment. Human cells consistently yield more ClickTags than mouse cells from the same or similarly treated samples, consistent with the RNA yield as shown in FIG. 22.

Figure 9E:
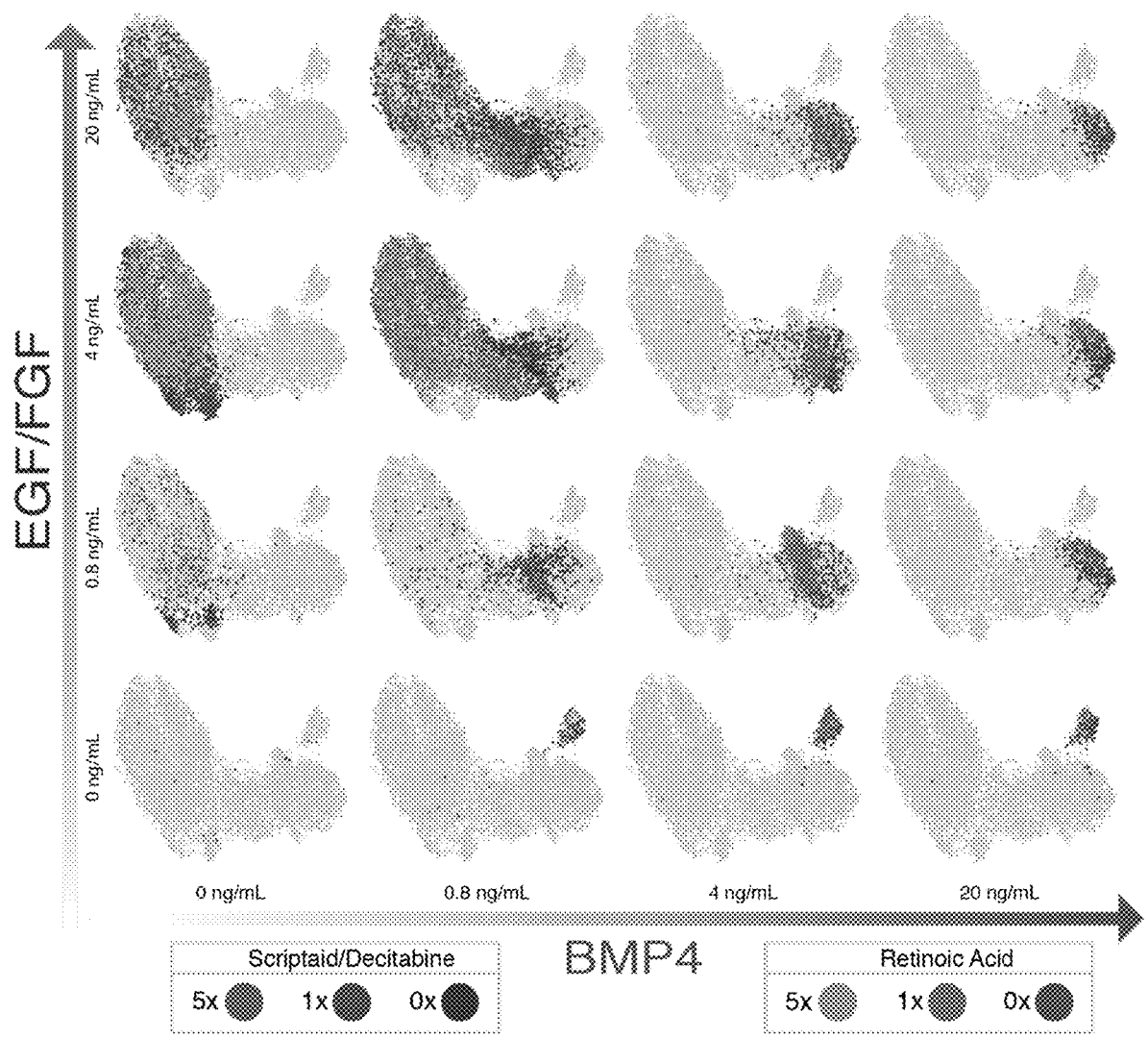

Finally, a complex perturbation experiment was performed to illustrate the utility and scope of multiplexed scRNA-seq. Neural stem cells (NSCs) are known to differentiate into many unique cell types in vivo, primarily neurons, astrocytes, and oligodendrocytes. In vitro, NSCs can be forced into different differentiation trajectories by exposing the cells to a variety of synthetic chemicals, hormones, and growth factors. The response of NSCs to varying concentrations of Scriptaid/Decitabine, epidermal growth factor (EGF)/basic fibroblast growth factor (bFGF), retinoic acid, and bone morphogenic protein 4 (BMP4) was investigated, producing a 4×4×6 perturbation array representing a large space of experimental conditions (FIG. 9A). NSCs were grown in a single 96-well plate with each culture corresponding to a unique combination of factors (FIG. 9C, FIG. 23). After fixation and ClickTag labeling (FIG. 9B), the samples were pooled and subjected to our modified 10× protocol. A total of 23,097 cells were detected based on cDNA counts, and sample assignment was performed for these cells based on a simple thresholding of ClickTag UMI counts. High concordance with the experimental design was observed, with 21,223 cells (92%) classified as positive for exactly two ClickTags, of which 99.8% corresponded to a pair in the experimental design (96 pairs were used out of 20/2=190 possible combinations). Visualization of the cell populations produced by each experimental condition revealed a complex interplay between the perturbants (FIG. 9E). On a global level, cell proliferation varied widely across the experiment, revealing growth rates specific not just to each condition but also to each cell state across the experiment. Highly proliferative states (clusters 0, 1,4, 6, 7, 8, 9, 10, 11, 12, and 17) differentially express various genes associated with cell growth and the cell cycle, including ribosomal, cytoskeletal, and cyclin-dependent proteins (see Highly Multiplexed Single-Cell RNA-seq for Defining Cell Population and Transcriptional Spaces. Jase Gehring, Jong Hwee Park, Sisi Chen, Matthew Thomson, Lior Pachter bioRxiv 315333; doi: doi.org/10.1101/315333, the content of which is hereby expressly incorporated by reference in its entirety). Conversely, samples deprived of EGF/bFGF exhibited apoptotic phenotypes including low cell counts and expression of stress response genes such as Cryab, Mt1, and Gpx4. We sought to define the cell states produced by the array of experimental conditions, a challenging procedure in scRNA-seq analysis and a potential roadblock to perturbation experiments where the presence of classical marker genes may depend on experimental conditions. Identification of functional cell states was greatly aided by the large number of samples in our experimental perturbation. Various distinct regions of transcriptome space were repeatedly populated by cells originating from multiple samples in localized regions of perturbation space, forming natural groupings of cells that were validated and assigned by clustering (FIG. 9D). The cluster occupancy of each sample revealed the structure of the cell populations produced across the experiment (FIG. 24A). Overall trends, such as high proliferation under low BMP4 conditions and high cluster specificity under high BMP4 conditions, were readily observed. Principal component analysis of the relative cluster abundance X sample matrix revealed relationships between the experimental inputs (FIG. 24B). The cell populations from each scRNA-seq sample associate directly with the experimental perturbations. Absence of EGF/bFGF has a drastic effect, yielding an isolated group of samples in PCA space, while BMP4 concentration has a graded effect and a strong interaction with retinoic acid, producing low BMP4, high BMP4, and BMP4+retinoic acid cell states. This analysis demonstrates that multiplexed scRNA-seq can be used to classify cell populations and interpret the conditions that produced them. In the context of a perturbation experiment, relevant features of the experimental space can be identified, e.g. the strong effect of BMP4 concentration shown here. Of perhaps greater interest would be to extend this proof-of-principle to biomedical diagnostics: by applying Bayes Rule to the relative cluster abundancexsamples matrix, it should be possible to infer disease conditions from high-resolution cell population observations.

Figure 28:
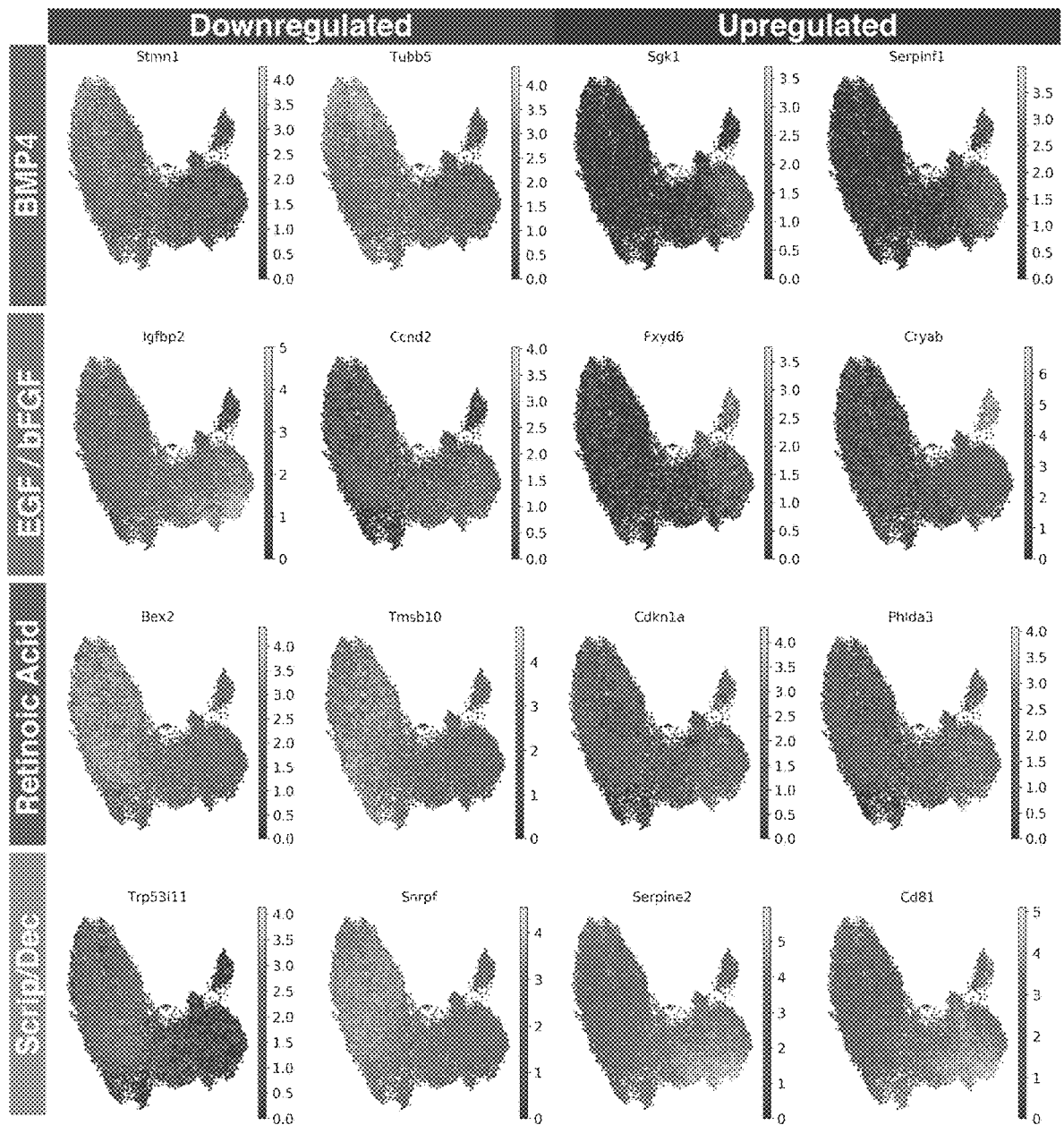
FIG. 28 depicts a linear regression model was used to identify genes associated with individual perturbants. For each chemical, examples of upregulated and downregulated genes are shown.

After evaluating the high-level information that can be gleaned from a large perturbation array, we closely examined two regions of our experimental space to illustrate the depth of analysis afforded by multiplexed scRNA-seq. First, we explored the portion of cell state space occupied by cells treated with intermediate EGF/bFGF concentrations, no BMP4, and moderate to no retinoic acid. Cells from seven samples accounted for practically all of clusters 14 and 15 and little across the rest of cell state space, exhibiting strong condition dependence (FIG. 24C). Differential expression analysis showed that cells in cluster 14 are defined by Hes5 expression and those in cluster 15 by Gadd45g expression. Elsewhere in experimental space, treatment with low BMP4 and high concentrations of retinoic acid generated highly proliferative cell states with complex population architectures (FIG. 24D). In this way, multiplexed scRNA-seq provides a detailed molecular dissection of heterogeneous cell populations produced from complex experimental conditions, addressing a long-standing goal in cell biology. FIG. 27 depicts UMAP embedding showing cells from the 96-sample perturbation experiment colored according to the experimental treatment for each cell. Global trends such as EGF/bFGF dependence, BMP4 response, and retinoic acid-driven proliferation are evident. FIG. 28 depicts a linear regression model was used to identify genes associated with individual perturbants. For each chemical, examples of upregulated and downregulated genes are shown.

It has been hypothesized that cells occupy a relatively limited number of transcriptional states in response to disease or experimental perturbation, and elucidating the connections between various perturbations will help in understanding cellular behavior. Efforts such as the Connectivity Map (CMap) project, while impressive in scope—CMap has been used to profile more than a million perturbation experiments—suffer from batch effects, averaging across cell populations, and difficulty in examining conditions that yield very few cells. ClickTag multiplexing overcomes these obstacles and provides single-cell whole-transcriptome resolution at very low cost. As multiplexing of DNA sequencing libraries has vastly improved the utility and adoption of high-throughput DNA sequencing, solutions for multiplexed scRNA-seq will similarly reduce costs, drive further increases in cell capacity, and extend the scope of scRNA-seq beyond bulk tissue profiling, enabling comparison of complex experimental samples with previously unattainable depth and scale.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of tagging a plurality of samples, comprising, for each sample of a plurality of samples:
   (a) incubating one or more amine-modified sample tags with a first heterobifunctional linker to generate one or more tetrazine-modified sample tags; and
   (b) incubating the one or more tetrazine-modified sample tags of step (a) with (i) a second heterobifunctional linker, and (ii) a sample comprising one or more particles, to generate particles tagged with one or more sample tags;
   wherein the first heterobifunctional linker comprises a first reactive group and a second reactive group, wherein the first reactive group of the first heterobifunctional linker comprises an amine-reactive functional group and wherein the second reactive group of first heterobifunctional linker comprises a tetrazine moiety; and
   wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety,
   wherein the one or more sample tags comprise a barcode sequence.

2. A method of tagging a plurality of samples, comprising, for each sample of a plurality of samples:
   (a) providing one or more tetrazine-modified sample tags; and
   (b) incubating one or more tetrazine-modified sample tags with (i) a second heterobifunctional linker, and (ii) a sample comprising one or more particles, to generate particles tagged with one or more sample tags;
   wherein the second heterobifunctional linker comprises a first reactive group and a second reactive group, wherein the first reactive group of the second heterobifunctional linker comprises an amine-reactive functional group and wherein the second reactive group of the second heterobifunctional linker comprises a tetrazine-reactive moiety,
   wherein the one or more sample tag comprise a barcode sequence.

3. The method of claim 1, wherein the amine-reactive functional group is selected from the group comprising an isothiocyanate, isocyanate, acyl azide, N-hydroxysuccinimide (NHS) ester, sulfonyl chloride, aldehyde, glyoxal, epoxide, carbonate, arylating agent, imidoester, carbodimide, and derivatives thereof.

4. The method of claim 1, wherein the tetrazine-reactive moiety is selected from the group comprising trans-cyclooctene (TCO), dibenzocyclooctyne (DBCO), difluorinated cyclooctyne (DIFO), bicyclononyne (BCN), dibenzocyclooctyne (DICO) and derivatives thereof.

5. The method of claim 2, wherein the amine-reactive functional group is selected from the group comprising an isothiocyanate, isocyanate, acyl azide, N-hydroxysuccinimide (NHS) ester, sulfonyl chloride, aldehyde, glyoxal, epoxide, carbonate, arylating agent, imidoester, carbodimide, and derivatives thereof.

6. The method of claim 2, wherein the tetrazine-reactive moiety is selected from the group comprising trans-cyclooctene (TCO), dibenzocyclooctyne (DBCO), difluorinated cyclooctyne (DIFO), bicyclononyne (BCN), dibenzocyclooctyne (DICO) and derivatives thereof.

7. The method of claim 1, wherein the tetrazine moiety comprises tetrazine, methyltetrazine, or derivatives thereof, and wherein the tetrazine is selected from the group comprising 1,2,3,4-tetrazine, 1,2,3,5-tetrazine, and 1,2,4,5-tetrazine.

8. The method of claim 1, wherein the first heterobifunctional linker is NHS-MTZ.

9. The method of claim 1, wherein the second heterobifunctional linker is NHS-TCO.

10. The method of claim 2, wherein the second heterobifunctional linker is NHS-TCO.

11. The method of claim 1, wherein the one or more amine-modified sample tags comprises an oligonucleotide, wherein the oligonucleotide comprises a 3' amine, a 5' amine, or combination thereof.

12. The method of claim 2, wherein the one or more amine-modified sample tags comprises an oligonucleotide, wherein the oligonucleotide comprises a 3'amine, a 5'amine, or combination thereof.

13. The method of claim 1, wherein the plurality of samples comprises more than 10 samples.

14. The method of claim 2, wherein the plurality of samples comprises more than 10 samples.

15. The method of claim 1, wherein the one or more particles comprise one or more synthetic particles, wherein the one or more synthetic particles comprise beads, synthetic cells, lipid droplets, and any combination thereof.

16. The method of claim 2, wherein the one or more particles comprise one or more synthetic particles, wherein the one or more synthetic particles comprise beads, synthetic cells, lipid droplets, and any combination thereof.

17. The method of claim 1, wherein one or more particles comprise one or more biological particles, wherein the one or more biological particles comprise one or more of prokaryotic cells, eukaryotic cells, viral particles, exosomes, protoplasts, microvesicles, and any combination thereof.

18. The method of claim 2, wherein one or more particles comprise one or more biological particles, wherein the one or more biological particles comprise one or more of prokaryotic cells, eukaryotic cells, viral particles, exosomes, protoplasts, microvesicles, and any combination thereof.

19. The method of claim 1, wherein step (b) comprises in situ generation of amine-reactive sample tags.

20. The method of claim 19, wherein nucleophilic attack of exposed primary amines on the one or more particles by the amine-reactive sample tags generates particles tagged with one or more sample tags.

21. The method of claim 1, wherein the amine-reactive functional group is N-hydroxysuccinimide (NHS) ester.

22. The method of claim 1, wherein the tetrazine moiety is methyltetrazine (MTZ).

\* \* \* \* \*